US011566063B2

(12) United States Patent
Kruse et al.

(10) Patent No.: US 11,566,063 B2
(45) Date of Patent: Jan. 31, 2023

(54) ANTIBODY BASED GENE THERAPY WITH TISSUE-DIRECTED EXPRESSION

(71) Applicant: Baylor College of Medicine, Houston, TX (US)

(72) Inventors: Robert Layne Kruse, Houston, TX (US); Karl-Dimiter Bissig, Houston, TX (US); Stephen M. G. Gottschalk, Houston, TX (US); Thomas C. T. Shum, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 412 days.

(21) Appl. No.: 16/334,706

(22) PCT Filed: Sep. 29, 2017

(86) PCT No.: PCT/US2017/054570
§ 371 (c)(1),
(2) Date: Mar. 19, 2019

(87) PCT Pub. No.: WO2018/064611
PCT Pub. Date: Apr. 5, 2018

(65) Prior Publication Data
US 2019/0225673 A1 Jul. 25, 2019

Related U.S. Application Data

(60) Provisional application No. 62/505,955, filed on May 14, 2017, provisional application No. 62/402,504, filed on Sep. 30, 2016.

(51) Int. Cl.
| *C07K 16/08* | (2006.01) |
| *A61K 48/00* | (2006.01) |
| *A61P 31/20* | (2006.01) |
| *C07K 16/28* | (2006.01) |
| *A61K 39/00* | (2006.01) |

(52) U.S. Cl.
CPC ............ *C07K 16/082* (2013.01); *A61K 48/00* (2013.01); *A61P 31/20* (2018.01); *C07K 16/2809* (2013.01); *A61K 2039/505* (2013.01); *A61K 2039/53* (2013.01); *C07K 2317/31* (2013.01); *C07K 2317/524* (2013.01); *C07K 2317/622* (2013.01); *C12N 2730/10133* (2013.01); *Y02A 50/30* (2018.01)

(58) Field of Classification Search
CPC combination set(s) only.
See application file for complete search history.

(56) References Cited

U.S. PATENT DOCUMENTS

| 5,932,448 | A |  | 8/1999 | Tso et al. |
| 10,059,767 | B2 | * | 8/2018 | Protzer ................. C07K 16/283 |
| 2004/0052773 | A1 |  | 3/2004 | Bogen et al. |
| 2005/0032114 | A1 |  | 2/2005 | Hinton et al. |
| 2014/0072581 | A1 | * | 3/2014 | Dixit ................. A61K 39/39591 435/69.6 |
| 2014/0088295 | A1 | * | 3/2014 | Smith ................. C07K 16/2809 530/387.3 |
| 2015/0030598 | A1 |  | 1/2015 | Croasdale et al. |

FOREIGN PATENT DOCUMENTS

| WO | WO 1997047654 | * 12/1997 |
| WO | 2012/136231 A1 | 10/2012 |

OTHER PUBLICATIONS

Zhou et al (Proc Amer Assoc Cancer Res, vol. 46, 2005, abstract 2262).*
Matar et al (Journal of Biomedical Science, 2009, 16:30, internet pp. 1-18).*
Geng et al (PNAS; Nov. 6, 2012; 109(45): 18471-18476).*
Zhang et al (Am J Physiol Gastrointest Liver Physiol., 2011, 301:G565-G573).*
Guan et al (Molecular Medicine Reports, 2017, 16:6102-6108).*
Invitrogen pcDNA™ 3.1 (+/−), (printed on Nov. 2021).*
Sobiepanek et al (Review and Research on Cancer Treatment, 2020, 6:79-87).*
Li et al (Acta Pharmacologica Sinica, 2010, 31:509-514).*
Roman et al (J of Biotechnology, 2016, 239:57-60).*
Galun et al (Hepatology, 2002, 35:673-679).*
Eren et al (Immunology, 1998, 93:154-161).*
Ji et al., "Targeted delivery of interferon-[alpha] to hepatitis B virus-infected cells using T-cell receptor-like antibodies", Hepatology, vol. 56, No. 6, Jul. 12, 2012 (Jul. 12, 2012), pp. 2027-2038.
Krebs et al: "T cells redirected to IL13R[alpha]2 with IL13 mutein-CARs have antiglioma activity but also recognize IL13R[alpha]I", Cytotherapy, vol. 16, No. 8, Aug. 2014 (Aug. 2014), pp. 1121-1131.
Realdi et al. "Expression of HBsAg on the membrane of hepatocytes in chronic carriers of hepatitis B virus infection" J Clin Immunol, Nov. 1978, vol. 1, No. 3., pp. 201-205.
Eren et al. "Preclinical evaluation of two human anti-hepatitis B virus (HBV) monoclonal antibodies in the HBV-trimera mouse model and in HBV chronic carrier chimpanzees" Hepatology, Sep. 2000, vol. 32, No. 3, pp. 500-590.

* cited by examiner

*Primary Examiner* — Laura B Goddard
(74) *Attorney, Agent, or Firm* — Boulware & Valoir

(57) ABSTRACT

Embodiments of the disclosure include methods and compositions for treatment of a medical condition related to the liver, including at least viral infections and liver cancer, for example. In specific embodiments, immunotherapies are provided for delivering polynucleotides locally to the liver, wherein the polynucleotides encode particular gene products that include bispecific antibodies, including those that target certain liver antigens, for example.

5 Claims, 28 Drawing Sheets
Specification includes a Sequence Listing.

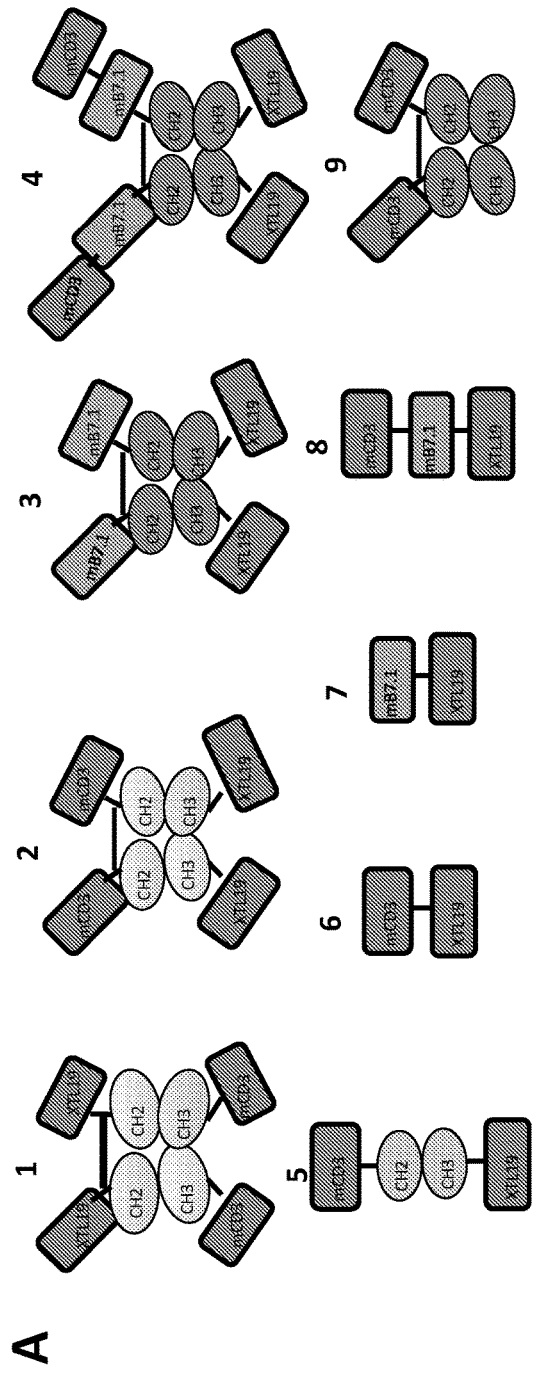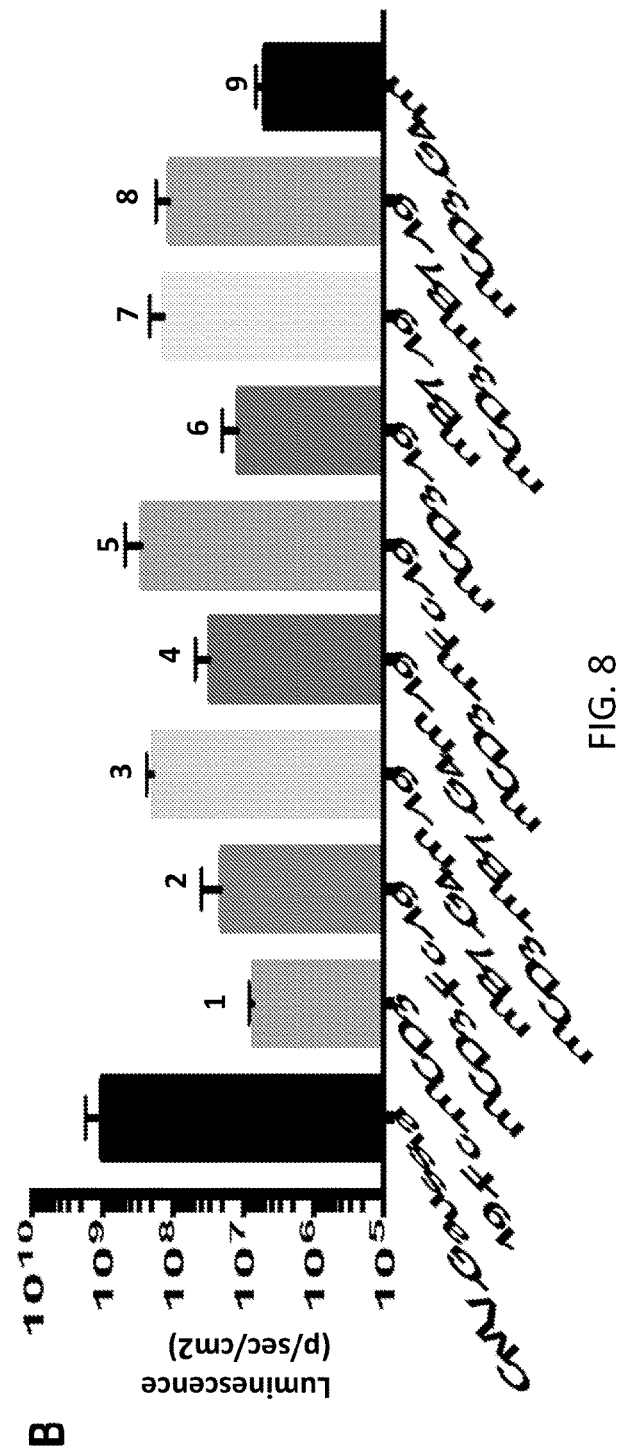
FIG. 8

Core sequence fused to GFP reading frame, to downstream expression of GFP-2A-Luciferase M D I D P Y K E F G A T V E
L L S F L P S D F F P S E R
D P R A S V M V K G P E L
F T G V P I L V E D G D
V N G H K F S V (SEQ ID NO:1)

DNA sequence of Core-GFP fusion, with the transcriptional start site for core mRNA indication indicated in red (same as the canonical pgRNA)

ATT GGT CTG CGC ACC AGC ACC ATG CAA CTT TTT CAC CTC TGC CTA ATC ATC TCT TGT TCA TGT CCT ACT GTT CAA GCC TCC AAG CTG TGC CTT GGG TGG CTT TGG GGC ATG GAC ATC GAC CCT TAT AAA GAA TTT GGA GCT ACT GTG GAG TTA CTC TCG TTT TTG CCT TCT GAC TTC TTT CCT TCA GTA CGA GAT CCC CGG GCG AGC TCG ATG GTG AGC AAG GGC GAG GAG CTG TTC ACC GGG GTG GTG CCC ATC CTG GTC GAG CTG GAC GGC GAC GTA AAC GGC CAC AAG TTC AGC (SEQ ID NO:2)

FIG. 13

A

```
M D I D P Y K E F G
A T V E L L S V F L P
S D F F P S V R D P
R A S S W M V K D E
E L F T G V V P L
E L L D G D M G
V E S S V V N
K F D V H
```

B

```
ATT GGT CTG CGC ACC AGC ACC ATG CAA CTT TTT CAC
CTC TGC CTA ATC ATC TCT TGT TCA TGT CCT ACT GTT
CAA GCC TCC AAG CTG TGC CTT GGG TGG CTT TGG GGC
ATG GAC ATC GAC CCT TAT AAA GAA TTT GGA GCT ACT
GTG GAG TTA CTC TCG TTT TTG CCT TCT GAC TTC TTT
CCT TCA GTA CGA GAT CCC CGG GCG AGC TCG ATG GTG
AGC AAG GGC GAG GAG CTG TTC ACC GGG GTG GTG
CCC ATC CTG GTC GAG CTG GAC GGC GAC GTA AAC GGC
CAC AAG TTC AGC
```

FIG. 28

ANTIBODY BASED GENE THERAPY WITH TISSUE-DIRECTED EXPRESSION

This application is a national phase application under 35 U.S.C. § 371 that claims priority to International Application No. PCT/US2017/054570 filed Sep. 29, 2017, which claims priority to U.S. Provisional Patent Application Ser. No. 62/402,504, filed Sep. 30, 2016, and also to U.S. Provisional Patent Application Ser. No. 62/505,955 filed May 14, 2017, all of which are incorporated herein by reference in their entirety.

TECHNICAL FIELD

The present disclosure concerns at least the fields of immunology, cell biology, molecular biology, and medicine.

BACKGROUND

The field of immunotherapy has promise in treating various infectious diseases and cancers with recent success in clinical trials. Through engineering or activating host immune cells, either artificially in vitro or in vivo, these diseases can potentially be reversed. However, these therapies can hold significant toxicities, lack of persistence, and dosing limitations. New methods that solve these limitations, maximizing the efficacy of treatment while minimizing off-target and off-organ toxicity are needed.

The present disclosure satisfies a long-felt need in the art by providing effective targeted immunotherapies for medical conditions that affect a particular tissue or organ, while lacking systemic side effects and toxicity, in at least certain aspects.

BRIEF SUMMARY

Embodiments of the disclosure concern methods and/or compositions for treatment of a disease in a specific tissue. In some embodiments, the disclosure concerns targeted therapy using compositions that are immunotherapeutic. In specific embodiments, the immunotherapies are useful for one or more liver-associated medical conditions.

Some embodiments of the disclosure concern gene therapy using delivery of a polynucleotide encoding a secretable form of a protein having multiple entities (such as a bipartite or tripartite protein, for example) that can bind substantially at the same time to an antigen specific for an organ or tissue and can also bind to a target that indirectly or directly stimulates an immune response. In particular aspects, the multi-component protein is able to bind a liver disease-specific antigen and to bind a target that facilitates re-direction of the immune system to diseased cells, for example localized in the liver. In specific embodiments, the composition is a bi-specific antibody and may also include a linker to connect operably the different components. In particular embodiments the compositions of the secretable polypeptides are delivered to an individual in need thereof in vivo in nucleic acid or protein form.

In specific embodiments the composition is provided locally and in the form of gene therapy such that constant and high production may occur on site in the desired tissue or organ, including the liver. That is, once the polynucleotide is delivered to a tissue or organ into cells locally, or via systemic injection and organ localization by the delivery vector, or via system injection and selective expression in the organ (all as examples), the local cells in the tissue are transduced and produce and secrete the desired protein. In embodiments wherein cancer is being treated, this may occur within the solid tumor mass and/or within the tumor microenvironment, for example.

Embodiments of the disclosure include methods of directly delivering T cell activation into a specific organ in vivo, thereby modulating the local immune response. This differs from recombinant protein strategies where antigen specificity guides to target organs, or from using cell-based carriers for delivery.

In certain embodiments of bispecific polypeptides, such as bispecific antibodies, the two parts may or may not function independently of each other, and in cases where they function independently of one another they may impart a synergistic effect, although in some cases the effect is additive.

In particular embodiments, a mixture of bispecific antibodies covering two or more different non-overlapping epitopes may be utilized to encompass the large majority of serotypes for a given virus (including global HBV serotypes) or variations within a cancer, thereby compensating for different affinities of the antibodies. In addition, introducing multiple antibody genes at the same time into the liver could generate bi-, tri-, quadra- or more specific antibodies through Fc pairing of heterologous genes, resulting in synergistic binding to multiple epitopes (including multiple HBsAg epitopes, as an example), in at least some cases.

Two different strategies may be utilized for efficient organ (such as hepatic) gene delivery of the bispecific antibodies, although other strategies may be employed. The first strategy may utilize a vector such as an adeno-associated virus (AAV) vector to deliver bispecific antibodies. AAV in specific cases affords a more permanent expression of bispecific antibodies that protects the individual from de novo infection cycles, but results herein suggest induced inflammation would destabilize the AAV genome quickly, leading to a transient, albeit safe therapy, in at least some cases. Furthermore, in specific embodiments the inflammation vaccinates against AAV capsid, preventing re-administration of therapy.

As an alternative approach one could deliver mRNA encoding bispecific antibodies directly into the liver, which would generate expression over time (starting with hours and lasting several days) that is well within therapeutic kinetics established herein, and yield a safe strategy with reliable pharmacokinetics. In such cases, the mRNA may be optimized by one or more means to prevent immune activation, increase stability, reduce any tendency to aggregate, such as over time, and/or to avoid impurities. Such optimization may include the use of modified nucleosides (for example, with 1-methylpseudouridine) in the mRNA and/or may include particular 5' UTRs, 3'UTRs, and/or poly(A) tail for improved intracellular stability and translational efficiency (see, e.g., Stadler et al., 2017, *Nat. Med.*).

The present disclosure provides novel methods of giving individuals an adaptive immune system to fight HBV infection. In certain embodiments, this is achieved through a single bispecific antibody molecule, which provides humoral immunity via the antibody portion, but also the ability to link and activate T cells against infected hepatocytes. Use of such a combination encompasses mechanisms utilizing covalently closed circular DNA (cccDNA) degradation, direct killing of infected cells, viral entry inhibition, innate immune activity, HBsAg secretion inhibition, and vaccine-like immune stimulation in a single therapeutic product, in at least some embodiments.

In one embodiment, there is a composition comprising a polynucleotide encoding a secretable polypeptide that comprises at least one tissue antigen-targeting entity (such as liver antigen or lung antigen, for example) and at least one immunostimulatory entity. The polypeptide may further comprise a linker region operably linking the at least one liver antigen-targeting entity and the at least one immunostimulatory entity. In specific embodiments, the liver antigen comprises an antigen on a liver cell, for example a diseased liver cell, such as a cancer cell. The cancer cell may be a primary liver cancer cell, such as a hepatocellular carcinoma cell or a hepatoblastoma cell. In specific cases, the cancer cell is derived from a cancer that metastasized to the liver. Regarding the liver antigen, it may be an antigen on a pathogen that infects the liver, and the pathogen may be a virus, bacteria, or fungus. In specific cases the virus is a Hepatitis A virus, Hepatitis B virus, Hepatitis C virus, Hepatitis D virus, or Hepatitis E virus. In some cases, the virus is Cytomegalovirus, Epstein-Barr virus, JC virus, BK virus, HSV-1, HSV-2, varicella zoster, HHV-6, HHV-8, Ebola virus, Zika virus, parvovirus, severe acute respiratory syndrome (SARS)-associated coronavirus, papillomavirus, influenza virus, or Yellow fever virus.

In particular cases, the liver antigen is HBV small surface antigen, HBV middle surface antigen (includes PreS2 domain), HBV large surface antigen (includes PreS1 and PreS2 domains), HBV core antigen, HBV e antigen, HCV E1 protein, HCV E2 protein, EBV glycoprotein, CMV glycoprotein, TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-1 1Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, gplOO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1. The liver antigen-targeting entity may comprise a single chain antibody, single chain variable fragment (scFv), peptide, camelid variable domain, shark IgNAR variable domain, single domain antibody, affimer or VHH antibody.

In certain embodiments, the immunostimulatory entity comprises a single chain antibody, single chain variable fragment (scFv), peptide, camelid variable domain, shark IgNAR variable domain, single domain antibody, affimer or VHH antibody against a receptor on an immune cell that provokes stimulation. The immunostimulatory entity may also comprise a cytokine, Fc receptor-binding entity, an ectodomain of an immune cell ligand, or a combination thereof. Specific cytokines include interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), granulocyte colony stimulating factor (G-CSF) and erythropoeitin, tumor necrosis factors (TNF) such as TNFα, lymphokines such as lymphotoxin, interferons such as interferon α, interferon β, and interferon γ, or various chemokines, or a combination thereof. In cases wherein an Fc receptor-binding entity is employed, it may be an IgG constant region, such as one from IgG4, IgG1, IgG3, or IgG2. In specific cases, the Fc receptor-binding entity comprises a monoclonal antibody that binds an Fc receptor. The Fc receptor-binding entity may comprise an scFv or single domain antibody that binds an Fc receptor.

In specific embodiments, the immunostimulatory entity comprises an anti-CD3 scFv, an anti-CD28 scFv, anti-41BB scFv, anti-OX40 scFv, anti-CTLA4 scFv, an anti-CD16 scFv, anti-PD1 scFv, anti-PD-L1 scFv, anti-CD47 scFv, part or all of the ectodomain for a ligand for CD28 (such as part or all of the ectodomain of CD80 and/or CD86), part or all of the ectodomain of 41BB ligand, SIRPalpha, part or all of the ectodomain of the LIGHT protein, ICOS-ligand, CD276 (B7-H3), B7-H4, and B7-H6, CD134L, or CD137L, and/or a combination thereof.

Regarding the linker, the linker may comprise a glycine-serine sequence, an Fc domain, one or more immunoglobulin domains, pairing of heterologous antibody light and heavy chain constant domains, or a combination thereof. In specific cases, the Fc domain comprises the human IgG1, IgG2, IgG3, or IgG4 Fc domains. The Fc domain may comprise one or more mutations that alters a property of the domain. The Fc domain may comprise a mutation that reduces FcRγ receptor binding, reduces the ability of the Fc domain to have complement binding, reduces the ability of the Fc domain to form immune complexes, and/or renders the domain to be monomeric in structure. In specific embodiments, the immunoglobulin domain is configured as a spacer for antigen binding. The immunoglobulin domain may comprise an immunoglobulin domain selected from the group consisting of extracellular regions of human proteins CD80, CD86, CD8, CD22, CD19, CD28, CD79, CD278, CD7, CD2, LILR, KIR, and CD4. In certain cases, the linker comprises one or more CH2 and/or CH3 domain(s) from one or more antibodies, which may containing mutations for monomeric forms in some embodiments. The linker may comprise the FcRn binding domain.

In particular embodiments, the secretable polypeptide comprises the following structure in a N-terminal to C-terminal orientation: liver antigen-targeting entity---linker---immunostimulatory entity; or immunostimulatory entity---linker---liver antigen-targeting entity. The polypeptide may comprise the following structure in a N-terminal to C-terminal orientation: liver antigen-targeting entity---linker---cytokine; or cytokine---linker---liver antigen-targeting entity.

In certain aspects polynucleotides may comprise RNA or DNA, and they may or may not be comprised in or on a vector or delivery vehicle, such as a viral vector (adenoviral vector, an adeno-associated viral vector, a retroviral vector, herpes virus vector, baculovirus vector or a lentiviral vector) or a non-viral vector or delivery vehicle, such as a lipid-based nanoparticle, a polymeric-based nanoparticle, or an exosome. In certain cases, when the polynucleotide is a messenger RNA (mRNA), the mRNA may or may not comprise modified nucleotides. In other cases, when the polynucleotide is a messenger RNA (mRNA), the mRNA comprises unmodified nucleotides. The mRNA may comprise one or more modified nucleotides. The vector or delivery vehicle may comprise an expression cassette that encodes the polypeptide. The expression cassette may comprise one or more regulatory sequences, such as sequences that comprise at least one tissue-specific regulatory sequence, including a liver-specific regulatory sequence. In specific cases, the tissue-specific regulatory sequence comprises a thyroxine binding globulin (TBG) promoter, a regulatory element as described in US 2011/0184049, albumin enhancer/promoter, apoE promoter, alpha1-antitrypsin promoter, or HBV core promoter (as examples). In cases wherein the vector is an adeno-associated viral vector, it may comprise an adeno-associated virus comprising a mutated capsid or is a serotype that transduces human liver. The adeno-associated viral vector may be AAV1, AAV2, AAV3, AAV4, AAV5, AAV6, AAV7, AAV8, AAV9, AAV10, AAV11, AAV12, or an AAV serotype isolated from a non-human primate. In some cases, the vector or delivery vehicle comprises a moiety that directs delivery of the vector or delivery vehicle to the liver.

In specific embodiments, the polynucleotide that encodes the secretable polypeptide also encodes a cytoprotective agent, although in certain cases they are comprised on separate polynucleotides. A cytoprotective agent may be delivered to an individual as a nucleic acid or as a polypeptide. The cytoprotective agent may be an apoptosis inhibitor. In specific embodiments, the cytoprotective agent is Bcl2, Bcl-XL, CED-0, Bfl-1, X-linked inhibitor of apoptosis protein (XIAP), c-IAP1, C-IAP2, NAIP, Livin, Survivin, serpin proteinase inhibitor 9, or SERPINB4, and other gene products that inhibit apoptosis. In specific cases, the cytoprotective agent is an siRNA, shRNA, miRNA, antisense oligonucleotide, or a morpholino that targets Fas receptor, TNFalpha receptor, Bax, Bid, Bak, or Bad and other gene products that otherwise promote apoptosis. In specific cases, the cytoprotective agent is a mRNA that comprises untranslated sequences that are targetable by an miRNA molecule of the individual restricting expression in desired cell types in a target tissue.

In one embodiment, there is a method of treating a medical condition, comprising the step of delivering to an individual with or at risk for the medical condition a therapeutically effective amount of at least one of the compositions encompassed by the disclosure (polynucleotide or polypeptide, for example). In specific embodiments, the medical condition is cancer or an infectious disease, such as Hepatitis B or Hepatitis C infection. The composition may be delivered to the individual more than once, and in such cases the duration between separate deliveries of the composition is within days, weeks, or months of one another. In some cases, a mixture of compositions is provided to the individual. The individual may be receiving, has received, or will receive an additional treatment for the medical condition, such as Paclitaxel, Doxorubicin, 5-fluorouracil, Everolimus, Melphalan, Pamidronate, Anastrozole, Exemestane, Nelarabine, Belinostat, Carmustine, Bleomycin, Bosutinib, Irinotecan, Vandetanib, Bicalutamide, Lomustine, Clofarabine, Cabozantinib, Dactinomycin, Cobimetinib, Cytoxan, Cyclophosphamide, Decitabine, Daunorubicin, Cytarabine, Docetaxel, Hydroxyurea, Decarbazine, Leuprolide, epirubicin, oxaliplatin, Asparaginase, Estramustine, Vismodegib, Amifostine, Flutamide, Toremifene, Panobinostat, Fulvestrant, Letrozole, Degarelix, Fludarabine, Pralatrexate, floxuridine, Gemcitabine, Afatinib, Imatinib Mesylate, Carmustine, Eribulin, Altretamine, Topotecan, Hydrea (Hydroxyurea, Palbociclib, Ponatinib, Idarubicin, Ifosfamide, Ibrutinib, Axitinib, Gefitinib, Romidepsin, Ixabepilone, Ruxolitinib, Cabazitaxel, Carfilzomib, Lenvatinib, Chlorambucil, Sargramostim, Cladribine, Trifluridine and Tipiracil, Leuprolide, Olaparib, Mitotane, Procarbazine, Megestrol, Trametinib, Mesna, Strontium-89 Chloride, Methotrexate, Mechlorethamine, Mitomycin, Vinorelbine, Sorafenib, nilutamide, Pentostatin, Mitoxantrone, Sonidegib, Alitretinoin, Carboplatin, Cisplatin, Pomalidomide, Mercaptopurine, Zoledronic acid, Lenalidomide, Octreotide, Tamoxifen, Dasatinib, Regorafenib, Histrelin, Sunitinib, Omacetaxine, Thioguanine, Dabrafenib, Erlotinib, Bexarotene, Decarbazine, Paclitaxel, Docetaxel, Temozolomide, Thiotepa, Thalidomide, Temsirolimus, Bendamustine hydrochloride, Triptorelin, Arsenic trioxide, lapatinib, Valrubicin, Histrelin, Vinblastine, Bortezomib, Etoposide, Tretinoin, Azacitidine, Vincristine, Pazopanib, Teniposide, Leucovorin, Crizotinib, Capecitabine, Enzalutamide, Trabectedin, Streptozocin, Vemurafenib, Goserelin, Vorinostat, Zoledronic acid, Everolimus, Idelalisib, Ceritinib, Abiraterone, or a combination thereof. One or more HBV antivirals may be provided to the individual. The composition may be delivered locally or systemically. In specific cases, the composition is delivered by injection intravenously, by directed injection using catheters into the portal vein or into hepatic artery, orally administered, subcutaneously injected, intramuscularly injected, or intraperitoneal injected. The delivery may or may not be by constant infusion.

In one embodiment, there is a polypeptide comprising the following components: 1) an antibody or antibody fragment comprising XTL19 scFv, XTL17 scFv, OST577 scFv, 5a19 scFv, or a combination thereof; 2) IgG1 wildtype Fc, IgG4 wildtype Fc, IgG1(AA) Fc, IgG2(AA) Fc, IgG1(AA)-CH2 domain only, IgG2(AA)-CH2 domain only, IgG4m Fc, IgG4m, CD80 ectodomain, CD86 ectodomain, or a combination thereof; and 3) anti-CD3 scFv, wherein in a N-terminal to C-terminal orientation the components of 1), 2), or 3) may be in any order. In certain cases, in a N-terminal to C-terminal orientation the order is 1), 2) and 3). In other cases, in a N-terminal to C-terminal orientation the order is 3), 2), and 1).

In another embodiment there is a method of treating a medical condition, comprising the step of delivering to an individual with or at risk for the medical condition a therapeutically effective amount of two separate polypeptides or one or more polynucleotides encoding the two separate polypeptides, wherein a first of the polypeptides comprises a liver antigen-targeting entity operably linked to a FcRn binding domain and a second of the polypeptides comprises a liver antigen-targeting entity operably linked to anti-CD3 scFv, such that the first polypeptide can inhibit the secretion of antigen particles, while the second polypeptide can not be inhibited by said particles and instead redirects T cells to a pathogenic cell's surface. In specific embodiments, the liver antigen-targeting entity operably linked to FcRn binding domain inhibits the secretion of surface antigen particles and Hepatitis B virions from a liver cell. In specific aspects, the second polypeptide is a bispecific antibody that activates T cells for proliferation, cytotoxicity, and cytokine release in the presence of the liver antigen. In one embodiment, the second polypeptide remains on a liver cell surface without internalization into the liver cell, thereby prolonging engagement with effector cells.

In one embodiment, provided herein is a method of generating monospecific and bispecific antibodies in situ in tissue (liver or lung, as examples) of an individual, comprising the step of providing to the individual two or more polynucleotides that each encode non-identical monospecific antibody polypeptides, wherein the antibodies produced from the polynucleotides in situ in tissue of the individual dimerize to each other, thereby generating a mixture of monospecific antibodies and bispecific antibodies within the tissue of the individual. The antibody may comprise one or more antigen binding domains that comprise a single chain antibody, single chain variable fragment (scFv), peptide, camelid variable domain, shark IgNAR variable domain, single domain antibody, affimer or VHH antibody. In some cases, the antigen-binding domains dimerize in their respective Fc regions, and in some cases the antigen-binding domains dimerize with a separate protein domain (such as one that comprises leucine zipper motifs, hinge and CH2 domain from immunoglobulin G, helix-loop-helix dimerization domain, or protein domain forming disulfide bonds). In some embodiments, at least one of the polynucleotides encodes a monospecific antibody for a disease antigen and at least one of the polynucleotides encodes a monospecific antibody for an immunostimulatory agent or serves an immunostimulatory agent domain. The immunostimulatory agent may be an anti-CD3 scFv, an anti-CD28 scFv, anti-41BB scFv, anti-OX40 scFv, anti-CTLA4 scFv, an anti-CD16 scFv, anti-PD1 scFv, anti-PD-L1 scFv, anti-CD47 scFv, part or all of the ectodomain for a ligand for CD28, part or all of the ectodomain of 41BB ligand, SIRPalpha, part or all of the ectodomain of the LIGHT protein, ICOS-ligand, CD276 (B7-H3), B7-H4, and B7-H6, CD134L, or CD137L, and/or a combination thereof. In some cases, part or all of the ectodomain for a ligand for CD28 is further defined as part or all of the ectodomain of CD80 and/or CD86.

In certain embodiments, there are methods of generating bispecific, trispecific and quadraspecific antibodies in situ in tissue (for example, liver or lung) of an individual, comprising the step of providing to the individual two or more polynucleotides that each encode non-identical bispecific antibody polypeptides, wherein the antibodies produced from the polynucleotides in situ in the tissue of the individual dimerize to each other, thereby generating a mixture of bispecific, trispecific and quadraspecific antibodies within the tissue of the individual. The antibody may comprise one or more antigen binding domains that comprise a single chain antibody, single chain variable fragment (scFv), peptide, camelid variable domain, shark IgNAR variable domain, single domain antibody, affimer or VHH antibody. The antibodies may dimerize in their respective Fc regions. The antigen-binding domains may dimerize with a separate protein domain, such as leucine zipper motifs, hinge and CH2 domain from immunoglobulin G, helix-loop-helix dimerization domain, or protein domain forming disulfide bonds. In specific embodiments, at least one of the polynucleotides encodes an antibody for a disease antigen and at least one of the polynucleotides encodes a monospecific antibody for an immunostimulatory agent or serves an immunostimulatory agent domain. In certain cases, the immunostimulatory agent is an anti-CD3 scFv, an anti-CD28 scFv, anti-41BB scFv, anti-OX40 scFv, anti-CTLA4 scFv, an anti-CD16 scFv, anti-PD1 scFv, anti-PD-L1 scFv, anti-CD47 scFv, part or all of the ectodomain for a ligand for CD28, part or all of the ectodomain of 41BB ligand, SIRPalpha, part or all of the ectodomain of the LIGHT protein, ICOS-ligand, CD276 (B7-H3), B7-H4, and B7-H6, CD134L, or CD137L, and/or a combination thereof. Part or all of an ectodomain for a ligand for CD28 may be further defined as part or all of the ectodomain of CD80 and/or CD86.

In some embodiments, there are compositions that when the secretable polypeptide is expressed at suitable levels in a tissue in vivo, the polypeptide elicits antigen-independent properties of immunostimulation in addition to antigen-dependent immunostimulation toward the antigen.

In some embodiments, there is a composition comprising an immunostimulatory monospecific antibody without an antigen-targeting domain that comprises activity of signaling and activating immune cells when expressed in tissue in vivo, but that lacks the same activity in vitro.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. The scope of the present application is not intended to be limited to the particular embodiments of the process, machine, manufacture, composition of matter, means, methods and steps described in the specification.

BRIEF DESCRIPTION OF THE DRAWINGS

For a more complete understanding of the present invention, reference is now made to the following descriptions taken in conjunction with the accompanying drawings, in which:

FIGS. 8A-8B. Bispecific antibody formats were screened for efficacy in vivo. (8A) Various bispecific antibody formats depicted were cloned into pCAGGS vectors, with the immune versus HBsAg binding components appended to different ends with different linker domains inserted. (8B) 15 ug of bispecific antibody vector was co-injected with 5 ug HBV-Luc, and luminescence measured at Day 4 post injection (n=3) (unpaired t-test, *=p<0.05). Definitions: mCD3=scFv against murine CD3epsilon derived from 2c11 hamster clone; mB7.1=ectodomain of mouse B7.1 protein; CH2,CH3=components of antibody Fc domain, gray=human IgG1, brown=human IgG4 with mutations to prevent Fc receptor binding, orange=human IgG1 with mutations to prevent dimerization and Fc receptor binding; XTL19=scFv derived from antibody clone 19.79.5;

FIG. 13. Sequence Information for the HBV-Luc plasmid (SEQ ID NO:1 and SEQ ID NO:2). A reported system for monitoring the immune response against HBV in real-time using bioluminescence was developed. The plasmid pSP65-HBVayw1.3 (gift of Stefan Wieland) was adapted for use. The endogenous HBV core promoter was utilized, in order to accurately assess the effects of cytokines on HBV gene expression. To utilize native elements, GFP was introduced as a fusion protein shortly after core protein translation, simplifying construction. Luciferase generated had no foreign sequences, being separated by 2A peptide cleavage;

FIGS. 28A-28B. Sequence information for pHBV-ffLuc. (28A) (SEQ ID NO:1) Core protein sequence (blue) fused to GFP reading frame (green) to enable downstream expression of GFP-2A-ffLuc. (28B) (SEQ ID NO:2) DNA sequence of core-GFP fusion, with the transcriptional start site for core mRNA indicated in red (same as the canonical pregenomic pgRNA), the start codon for the core protein is indicated in blue, and the start codon of GFP is indicated in green.

DETAILED DESCRIPTION

Figure 1:
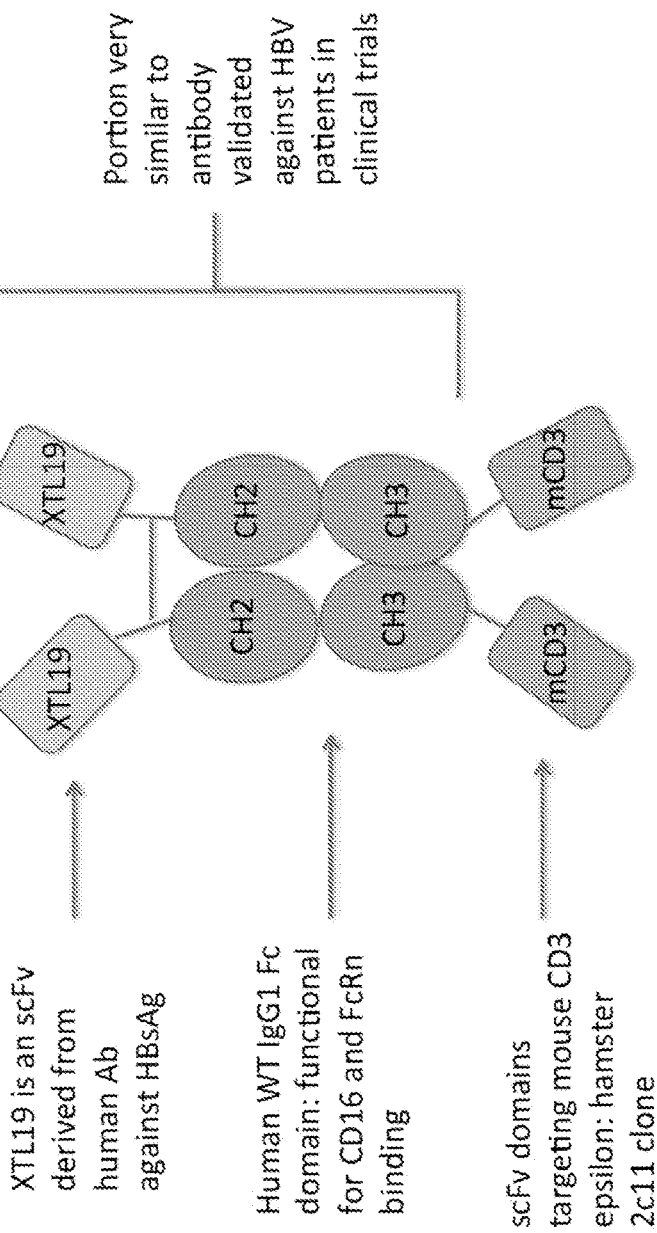
FIG. 1 illustrates an example of a bispecific antibody of the disclosure.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

In particular cases, the present disclosure concerns a strategy of targeting viral infections and cancers of the liver using, for example, bispecific antibodies that re-direct the immune system toward the diseased cells. Previously in the art, such molecules have been developed as recombinant proteins administered to an individual in need thereof. In clinical trials targeting various tumors, the efficacy of this strategy has been poor and limited to only a few successes requiring constant infusion (for example, blinatumomab targeting CD19+ cells). In the present disclosure, polynucleotides encoding these proteins may be delivered directly to the affected organ, such that they will be highly concentrated and reach the diseased cells readily, as opposed to systemic therapies. Furthermore, this reduces the dose-limited toxicities noted in the previous trials for this class of molecule.

The present disclosure particularly concerns applications targeting the liver tissue, which is the host of various infectious diseases and cancer disorders (both primary and metastatic). Toward targeting the liver, gene therapy embodiments can utilize adeno-associated virus, or lipid-nanoparticle (LNP) mRNA delivery, for example, both of which have already been validated for efficacy in humans and chimpanzees respectively. Specifically, encompassed herein are bispecific antibodies against Hepatitis B virus that have resulted in a 100-fold decrease in viral genomes within 4 days of treatment compared to an untreated group in immunocompetent mice, and there is clearance of the virus by 8 days, compared to viral genomes being unaffected at that point in untreated mice. Similar efficacy has been observed in monospecific constructs targeting T cell activation alone. Considering that current therapies cannot target the viral genome, this is a significant advance in the art. Encompassed herein are examples of different antibody sequences and bispecific designs that yield efficacy in mice at least. Also encompassed herein are unique linker compositions that can maintain proper geometry for efficacy and T cell activation, for example. The present disclosure demonstrates the ability to target an autologous antigen in the liver, as an example of a specific organ, and the clearance of signal in those cells, which may be extrapolated for application into a number of autologous tumor antigen targets, for example.

I. Examples of Compositions

The present disclosure provides novel compositions for use in the treatment or prevention of one or more symptoms of a medical condition, such as one that affects a specific organ, such as the liver, which will be utilized as an example hereafter. In specific embodiments, the compositions comprise one or more components that are able to bind a liver disease antigen, which includes an antigen on a cell that is located in the liver or an antigen on a cell outside the liver but that is also found on a cell that is located in the liver. In certain embodiments the compositions comprise one or more components that are able to stimulate and/or activate the immune system, including stimulate and/or activate the immune system to focus on the liver, including diseased cells in the liver. The composition(s) may also comprise at least one linker that operably links two or more components of the molecule. The two or more components may work in conjunction with one another or may work separately from one another. The two or more components of the composition(s) may have similar or separate functions and/or they may each be able to bind different targets. Upon binding of their respective targets, they may directly or indirectly result in downstream action(s) that may or may not be separate downstream actions.

A. Liver Disease Antigen-Targeting Entity

Embodiments of the disclosure include compositions that comprise at least one liver disease antigen-targeting entity. The entity may comprise 1, 2, 3, 4, or more liver antigen-targeting entities. When multiple liver disease antigen-targeting entities are present on one molecule of the composition, the different entities may abut one another, or there may be sequence in between them on the molecule that is not of a liver antigen-targeting entity. In cases wherein there is sequence between two liver disease antigen-targeting entities, the liver antigen-targeting entities are still configured such that they may function properly, including acting in conjunction, in at least certain cases. The different liver disease antigen-targeting entities may or may not have the same liver antigen to target, and certain embodiments encompass a cocktail of liver disease antigen-targeting entities, towards one more antigens, being administered to an individual at the same time.

In particular embodiments, the liver antigen-targeting entity targets an antigen on the surface of a cell in the liver. That cell may be a normal liver cell or a diseased liver cell. In specific embodiments, the liver antigen-targeting entity is able to directly or indirectly bind at least one antigen on a cell in the liver. In cases wherein the cell in the liver is a diseased cell, the cell may infected with a pathogen, such as a virus or bacteria or parasite. In cases wherein the pathogen is a parasite, the targeted antigen may be from *Plasmodium falciparum*, the causative agent of malaria. Other parasites infecting the liver that could be targeted include *Plasmo-* dium vivax, Plasmodium ovale, Plasmodium malariae, Plasmodium knowlesi, Toxoplasmosis gondii, Trypanosoma cruzi, Echinococcosis, Fasciola hepatica, Clonorchis sinensis, Schistosoma japonicum, Schistosoma mansoni, Schistosoma intercalatum, Ascaris lumbricoides, Baylisascaris procyonis, Toxocara canis, or Toxocara cati. In cases wherein the pathogen is a virus, the liver antigen-targeting entity may target a cell that expresses an antigen from any type of Hepatitis virus, such as Hepatitis A, Hepatitis B, Hepatitis C, Hepatitis D, or Hepatitis E virus, or another type of virus, such as Cytomegalovirus, Epstein-Barr virus, JC virus, BK virus, HSV-1, HSV-2, varicella zoster, Ebola virus, Zika virus, parvovirus, severe acute respiratory syndrome (SARS)-associated coronavirus, papillomavirus, influenza virus, or Yellow fever virus. In other cases, the liver disease antigen-targeting entity targets an antigen on a cancer cell that is in the liver (such as hepatocellular carcinoma or hepatoblastoma), including a primary cancer cell, a cancer cell that originates from a cancer that has metastasized to the liver, a refractory cancer cell, and so forth.

The liver antigen-targeting entity may be of any kind, so long as it is able to bind directly or indirectly to the liver antigen. The liver antigen-targeting entity may be a protein or peptide, including that encoded by a particular polynucleotide that may be provided to an individual in need thereof (although in alternative embodiments the composition provided to the individual is a peptide or a polypeptide and not a polynucleotide). In particular embodiments, the liver antigen-targeting entity comprises an antibody or functional fragment thereof, including a single chain antibody, a single chain variable fragment, a single domain antibody, a camelid antibody, or a llama antibody, for example. Other examples include affimers. Specific examples of liver antigen-targeting entities includes those that target at least HBV small surface antigen, HBV middle surface antigen (includes PreS2 domain), HBV large surface antigen (includes PreS1 and PreS2 domains), HBV core antigen, HBV e antigen, HCV E1 protein, HCV E2 protein, EBV glycoprotein, CMV glycoprotein, and so forth. For cancers within the liver including metastases, specific examples of antigens that could be targeted include TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-1Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gpl00, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1, for example.

In certain cases, the liver antigen-targeting entity comprises one or more antibodies or antibody fragments, such as an scFv. Particular scFvs may include those that directly bind at least one Hepatitis viral antigen, such as scFvs derived from monoclonal antibodies 17.1.41, 19.79.5, OST577, scFv A5, VHH-S4, VHH-S5, HzKR127, KR359, 2B6, 2D9, 2E7, 2G3, ADRI-2F3, E6F6, HB-C7A, 5alpha19, and 1C9, for example.

In certain cases, the liver antigen-targeting entity comprises one or more peptides or peptide fragments. Particular peptides may include those that directly bind at least one Hepatitis viral antigen. Particular peptides may include those that directly bind at least one Hepatitis viral antigen, such as Peptide A5, Peptide ETGAKPH, Peptide P7, Peptide pC, Peptide p2, Peptide p5, Peptide p18, Peptide 4B10, or Peptide SRLLYGW, for example.

In certain cases, the liver antigen-targeting entity comprises two scFvs, such as tandem scFvs. In particular, the tandem scFvs bind different liver antigen-targeting entities, although in some cases the liver antigen-targeting comprises tandem scFvs that bind the same antigen, for example at the same or different site on the antigen; they may or may not bind different epitopes on the same antigen.

In specific embodiments, a liver antigen-targeting entity is operably linked, such as on a fusion protein, to a component that binds one or more immunoglobulin receptors, such as an Fc receptor. The liver antigen-targeting entity may be linked to an FcRn binding domain, for example. Compositions wherein the liver antigen-targeting entity is linked to one or more FcRn binding domains provides activity of inhibition of secretion of surface antigen particles and HBV virions (as an example) from a liver cell. The Fc domain may comprise a mutation that reduces FcRγ receptor binding and cytotoxicity, reduces the ability of the Fc domain to inhibit complement binding, reduces the ability of the Fc domain to form immune complexes, and/or renders the domain to be monomeric in structure.

In another case, the linker region between the liver disease antigen-targeting entity and a CD3 binding domain will lack FcRn binding, such as via mutations in an Fc domain linking the two moieties, preventing the hepatocyte from endocytosis of the antibody therapeutic. Mutations at residues Ile253Ala, Ser254Ala, His435Ala and Tyr436Ala encompassing residues at CH2-CH3 interface of human IgG Fc domains serve to abrogate FcRn binding and can be used in this embodiment. Such a feature may be desirable in order to maximize the ability of immune cells to target liver disease antigens on the cell surface via retaining appropriate efficacious geometries in treating various diseases, while also optimizing more of the bispecific molecule on the surface of the target cell as opposed to intracellular trafficking.

Single chain antibody sequences that may be utilized in specific embodiments are as follows:

XTL19 (targets HB sAg)
(SEQ ID NO: 3)
QVQLVESGGG VVQPGGSLRL SCAPSGFVFR SYGMHWVRQT PGKGLEWVSL

IWHDGSNRFY ADSVKGRFTI SRDNSKNTLY LQMNSLRAED TAMYFCAR

-continued

ERLIAAPAAF DLWGQGTLVT VSSGGGGSGG GGSGGGGSSY VLTQPPSVSV

APGKTARISC GGNNIGTKNV HWYQQKPGQA PVLVVYADSD RPSGIPERFS

GSNSGNTATL TISRVEVGDE ADYYCQVWDS VSYHVVFGGG TTLTVLG

XTL17 (targets HBsAg)
(SEQ ID NO: 4)
QVQLVESGGG VVRPGRSLRL SCAASGFAFS DYSINWVRQA PGKGLEWVAI

ISYDGRITYY RDSVKGRFTI SRDDSKNTLY LQMNSLRTED TAVYYCARQY

YDFWSGSSVG RNYDGMDVWG LGTTVTVSSG GGGSGGGGSG GGGSDIVMTQ

SPLSLSVTPG EPASISCRSS QSLLHRSGNN YLDWYLQKPG HSPQLLIYVG

SNRASGVPDR FSGSGSGTEY TLRISTVEAE DVGVYYCMQA LQTPRTFGQG TKLEIKR

OST577 (targets HBsAg)
(SEQ ID NO: 5)
QVQLVESGGG VVQPGRSLRL SCAASGFTFS RYGMHWVR QAPGKGLEWV

AVISYDGSNK WYADSVKGRF TISRDNSKNT LFLQMHSL RAADTGVYYC

AKDQLYFGSQ SPGHYWVQGT LVTVSSGGGG SGGGGSGGGG SQSQLTQPPS

VSVAPGQTAR ITCGGDNIGS KSVNWFQQKP GQAPVLVVYD DNERPSGISE

RFSGSNSGNT ATLTISRVEA GDEADYYCQV WDSSSDHVVF GGGTKLTVL

Hu12F6 (targets human CD3 epsilon)
(SEQ ID NO: 25)
DIQMTQSPSS LSASVGDRVT MTCRASSDSV SYMHWYQQTP GKAPKPWIYA

TSNLASGVPS RFSGSGSGTD YTLTISSLQP EDIATYYCQQ WSSNPPTFGQ

GTKLQITRGG GGSGGGGSGG GGSQVQLVQS GGGVVQPGRS LRLSCKASGY

TFTSYAMYWV RQAPGKGLEW VAIINPSSGY TKNQKFDRFT ISADKSKSTA

FLQMDSLRPE DTGVYFCARD GDYDVYFSAS CFGPDYWGQG TPVTVSS

Humanized UCHT1 (targets human CD3 epsilon)
(SEQ ID NO: 26)
DIQMTQSPSS LSASVGDRVT ITCRASQDIR NYLNWYQQKP GKAPKLLIYY

TSRLESGVPS RFSGSGSGTD YTLTISSLQP EDFATYYCQQ GNTLPWTFGQ

GTKVEIKRTG GGGSGGGGSG GGGSEVGQLV ESGGGLVQPG GSLRLSCAAS

GYSFTGYTMN WVRQAPGKGL EWVALINPYK GVTTYADSVK GRFTISVDKS

KNTAYLQMNS LRAEDTAVYY CARSGYYGDS DWYFDVWGQG TLVTVSS

HuM291 (targets human CD3 epsilon)
(SEQ ID NO: 27)
QVQLVQSGAE VKKPGASVKV SCKASGYTFI SYTMHWVRQA PGQGLEWMGY

INPRSGYTHY NQKLKDKATL TADKSASTAY MELSSLRSED TAVYYCARSA

YYDYDGFAYW GQGTLVTVSS GGGGSGGGGS GGGGSDIQMT QSPSSLSASV

GDRVTITCSA SSSVSYMNWY QQKPGKAPKR LIYDTSKLAS GVPSRFSGSG

SGTDFTLTIS SLQPEDFATY YCQQWSSNPP TFGGGTKVEI K gOKT3-5 (targets human CD3 epsilon)
(SEQ ID NO: 28)
QVQLVQSGGG VVQPGRSLRL SCKASGYTFT RYTMHWVRQA PGKGLEWIGY

INPSRGYTNY NQKVKDRFTI STDKSKSTAF LQMDSLRPED TAVYYCARYY

DDHYCLDYWG QGTPVTVSSG GGSGGGGSG GGGSDIQMTQ SPSSLSASVG

DRVTITCSAS SSVSYMNWYQ QTPGKAPKRW IYDTSKLASG VPSRFSGSGS

GTDYTFTISS LQPEDIATYY CQQWSSNPFT FGQGTKLQIT R gOKT3-7 (targets human CD3 epsilon)
(SEQ ID NO: 29)
QVQLVQSGGG VVQPGRSLRL SCKASGYTFT RYTMHWVRQA PGKGLEWIGY

INPSRGYTNY NQKVKDRFTI SRDNSKNTAF LQMDSLRPED TGVYFCARYY

DDHYCLDYWG QGTPVTVSSG GGGSGGGGSG GGGSDIQMTQ SPSSLSASVG

DRVTITCSAS SSVSYMNWYQ QTPGKAPKRW IYDTSKLASG VPSRFSGSGS

GTDYTFTISS LQPEDIATYY CQQWSSNPFT FGQGTKLQIT R

TGN1412 (targets human CD28)
(SEQ ID NO: 30)
QVQLVQSGAE VKKPGASVKV SCKASGYTFT SYYIHWVRQA PGQGLEWIGC

IYPGNVNTNY NEKFKDRATL TVDTSISTAY MELSRLRSDD TAVYFCTRSH

YGLDWNFDVW GQGTTVTVSS GGGGSGGGGS GGGGSDIQMT QSPSSLSASV

GDRVTITCHA SQNIYVWLNW YQQKPGKAPK LLIYKASNLH TGVPSRFSGS

GSGTDFTLTI SSLQPEDFAT YYCQQGQTYP YTFGGGTKVE IK

Additional single chain variable fragments that can be employed in tissue-directed bispecific antibody expression are provided below:

scFv A5 (against HBsAg, Reference PMID: 14597165)
VHH-S4 (against HBsAg, Reference PMID: 19085971)
VHH-S5 (against HBsAg, Reference PMID: 19085971)
HzKR127 (against PreS1, Reference PMID: 18176536)
KR359 (against PreS1, Reference PMID: 10772975)
2B6 (against PreS1, Reference PMID: 26888694)
2D9 (against PreS1, Reference PMID: 26888694)
2E7 (against PreS1, Reference PMID: 26888694)
2G3 (against PreS1, Reference PMID: 26888694)
ADRI-2F3 (against HBsAg, Reference PMID: 25923526)
E6F6 (against HBsAg, Reference PMID: 26423112)
HB-C7A (against HBsAg, Reference PMID: 18479762)
5a19 (against PreS1, Reference PMID: 11749974)
scFv 1C9 (against HBV core protein, PMID: 10385671

Peptides can also be used as the targeting ligand toward HBsAg, alone or in conjunction with other moieties. In some embodiments, the peptides will form a dual binding agent, wherein a peptide and scFv against different HBsAg epitopes or proteins are joined in tandem to result in bivalent binding to target antigen. Particular embodiments would utilize a PreS1 binding peptide in conjunction with an antibody that binds to the small HBsAg protein. Regardless of the embodiment, some contemplated peptides targeting HBV envelope for use in chimeric antigen receptors may utilize the sequence listed below:

Peptide A5
(targets PreS1, Reference PMID: 24966187):
(SEQ ID NO: 6)
SGSGLKKKWST Peptide ETGAKPH
(targets HBsAg, Reference PMID: 16087122):
(SEQ ID NO: 7)
CETGAKPHC Peptide P7
(targets PreS1, Reference PMID: 21856287):
(SEQ ID NO: 8)
KHMHWHPPALNT -continued Peptide pC
(targets PreS1, Reference PMID: 17192308):
(SEQ ID NO: 9)
SGSGWTNWWST Peptide p2
(targets PreS1, Reference PMID: 17192308):
(SEQ ID NO: 10)
NNWWYWWDTLVN Peptide p5
(targets PreS1, Reference PMID: 17192308):
(SEQ ID NO: 11)
GLWRFWFGDFLT Peptide p18
(targets PreS1, Reference PMID: 17192308):
(SEQ ID NO: 12)
WTDMFTAWWSTP Peptide 4B10
(targets PreS1, Reference PMID: 27384014):
(SEQ ID NO: 13)
LRNIRLRNIRLRNIRLRNIR Peptide SRLLYGW
(targets PreS1, Reference PMID: 15996026):
(SEQ ID NO: 14)
CSRLLYGWC Examples of scFvs that may be employed to target a cancer antigen are as follows:

scFv 4H5 (against human EphA2, PMID: 17241664)

scFv 3E11 or 2G9 or 4G5 or 3D8 or 2E10 (against human glypican-3, PMID: 22564378)

scFv hu1G8 (against human prostate stem cell antigen, PMID: 19010866)

scFv HMFG2 (against human MUC1, PMID: 18354214)

scFv 139 (against human EGFRvIII, PMID: 22780919)

scFv P4 (against human mesothelin, WO2013063419 A2)

scFv C2-45 (against human carcinoembryonic antigen, PMID: 20683006)

scFv C4 (against human folate receptor-alpha, PMID: 26101914)

B. Immunostimulatory Entity

Embodiments of the disclosure include compositions that comprise one or more immunostimulatory entities. The composition may comprise 1, 2, 3, 4, or more immunostimulatory entities. When multiple immunostimulatory entities are present on a molecule of the composition, the different entities may abut one another, or there may be sequence in between them on the molecule that is not of an immunostimulatory entity. In cases wherein there is sequence on the molecule between two immunostimulatory entities, the immunostimulatory entities are still configured such that they may function properly, including acting in conjunction, in at least certain cases.

In particular embodiments, one or more immunostimulatory entities in the composition directs the immune system of an individual to which the composition is provided toward certain cells in the body, including diseased liver cells in the body. The composition(s) elicit T cell activation and cytokine secretion, in at least some embodiments. In particular embodiments, the immunostimulatory domain(s) activate T cells, NK cells, NK T cells, macrophages, monocytes, basophils, neutrophils, eosinophils, mast cells, Kupffer cells, or B cells at the liver and indirectly or directly cause activation of signaling pathways in immune effector cells. The composition(s) may facilitate recruitment of T cells to the surface of cells in the liver, including diseased cells in the liver, such as cancer cells or pathogen-infected cells in the liver. In some embodiments, the protein secreted will just contain one or more immunostimulatory domains with or without linkers, and lack a liver disease antigen targeting domain. This serves to stimulate the immune response within the organ, without any particular redirection of immune cells towards a diseased cell. The mechanism may include aggregation of secreted protein made in tissue to provide stimulation to surrounding cells.

The immunostimulatory entity may comprise a polypeptide or a peptide, or a polynucleotide encoding a polypeptide or peptide. In specific cases, the immunostimulatory domain comprises an antibody or functional antibody fragment, including an scFv. Particular examples include an anti-CD3 scFv, an anti-CD28 scFv, anti-41BB scFv, anti-OX40 scFv, anti-CTLA4 scFv, an anti-CD16 scFv, anti-PD1 scFv, anti-PD-L1 scFv, anti-CD47 scFv, part or all of the ectodomain for a ligand for CD28 (such as part or all of the ectodomain of CD80 and/or CD86), part or all of the ectodomain of 41BB ligand, SIRPalpha, part or all of the ectodomain of the LIGHT protein, ICOS-ligand, CD276 (B7-H3), B7-H4, and B7-H6, CD134L, CD137L, a cytokine, or a combination thereof, for example. Examples of cytokines include interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), granulocyte colony stimulating factor (G-CSF) and erythropoeitin, tumor necrosis factors (TNF) such as TNFα, lymphokines such as lymphotoxin, interferons such as interferon α, interferon β, and interferon γ, and chemokines, and a combination thereof.

In some embodiments, the polynucleotide delivered will encode an immune stimulating protein without any antigen-binding component. For these embodiments, localization to the target organ may be achieved by the specificity of tissue delivery alone. Furthermore, the entity will only activate immune cells and not form synapses between the diseased cell and immune cells. This offers the ability to stimulate immune cells alone, or in certain cases, provide therapy for diseases that do not express disease specific-antigen targets on the cell surface. The activation of immune cells may be achieved by latent aggregation via expression of polypeptides from the target tissue cells, an example being in the specific embodiment of the liver, facilitating activation of target immune receptors in the absence of a target disease antigen to facilitate signaling.

C. Linker

In particular embodiments of the disclosure, there is a linker that connects at least one liver antigen-targeting entity with at least one immunostimulatory entity, for example on the same molecule. The linker is configured to maintain proper geometry for efficacy and T cell activation, in particular embodiments.

In some cases, the linker comprises sequence that is rich in glycine and/or serine. In specific cases, the linker comprises sequence that is at least 50, 55, 60, 65, 70, 75, 80, 81, 82, 83, 84, 85, 86, 87, 88, 89, 90, 91, 92, 93, 94, 95, 96, 97, 98, or 99% glycine and/or serine. In specific cases the linker also comprises one or more threonines. The linker may comprise 2, 3, 4, 5, 6, 7, 8, 9, 10, or more repeats of a series of glycine and/or serine residues (for example, GGSG and/or GGGS). In specific embodiments, the linker is of a certain length, such as at least 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, or 150 amino acids in length. In other cases, the linker is no more than 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, or 150 amino acids in length.

In some cases, one or more Fc domains are used in the linker, including an Fc domain from IgG1, IgG2, IgG3, or IgG4, for example. Specific embodiments employ CH2 and CH3 domains from IgG, singly or in combination. In some cases, the Fc domain employed in the linker is modified, and there may be one or more modifications. In particular embodiments, the modification(s) alters one or more of the following properties of the Fc domain: 1) to have reduced FcR (CD64, CD32, CD16, CD23, CD89) γ receptor binding; 2) to make them monomeric in structure; 3) to remove complement activation 4) to remove FcRn binding; and/or 5) to have increased FcRγ receptor binding.

In certain embodiments, one or more immunoglobulin domains are employed in the linker. The immunoglobulin domain(s) may come from any member of the Ig superfamily, in some embodiments. In specific embodiments, one or more domains from CD86 and/or CD80, CD4 and/or CD8, are utilized. The domain may be an Ig variable-like (IgV) domain, an Ig constant-like (IgC) domains, and/or an intracellular domain, for example. In specific embodiments, when an Fc domain is utilized the CH2 and/or CH3 domain may be replaced with an immunoglobulin domain, such as a domain from CD80, CD86, CD4 and/or CD8, for example.

In specific aspects, the IgG Fc region comprises a) one or more mutations to disrupt FcR binding, b) a deletion of the CH2 domain, and/or c) replacement of the CH2 domain, for example with another immunoglobulin domain from a different human protein (such as an immunoglobulin from an alternative human protein selected from human CD4 domains D2 through D4). Mutations that disrupt FcR binding may be located in the hinge region and/or glycosylation site of IgG Fc domain (including IgG1 Fc domain, IgG2 Fc domain, or IgG4 Fc domain, for example.

Linker domain sequences that may be utilized in specific embodiments are as follows:

IgG1(AA) Fc (linker domain or region, hinge-CH2-CH3, mutated FcR binding)
(SEQ ID NO: 31)
EPKSCDKTHT CPPCPAPEAA GGPSVFLFPP KPKDTLMISR TPEVTCVVVD

VSHEDPEVKF NWYVDGVEVH NAKTKPREEQ YNSTYRVVSV LTVLHQDWLN

GKEYKCKVSN KALPAPIEKT ISKAKGQPRE PQVYTLPPSR DELTKNQVSL

TCLVKGFYPS DIAVEWESNG QPENNYKTTP PVLDSDGSFF LYSKLTVDKS

RWQQGNVFSC SVMHEALHNH YTQKSLSLSP GK

IgG2(AA) Fc (linker domain or region, hinge-CH2-CH3, mutated FcR binding)
(SEQ ID NO: 32)
ERKCCVECPP CPAPPAAAPS VFLFPPKPKD TLMISRTPEV TCVVVDVSHE

DPEVQFNWYV DGVEVHNAKT KPREEQFNST FRVVSVLTVV HQDWLNGKEY

KCKVSNKGLP APIEKTISKT KGQPREPQVY TLPPSREEMT KNQVSLTCLV

KGFYPSDISV EWESNGQPEN NYKTTPPMLD SDGSFFLYSK LTVDKSRWQQ

GNVFSCSVMH EALHNHYTQK SLSLSPGK

IgG4m Fc (linker domain or region, hinge-CH2-CH3, mutated FcR binding)
(SEQ ID NO: 33)
ESKYGPPCPS CPAPPVAGPS VFLFPPKPKD TLMISRTPEV TCVVVDVSQE

DPEVQFNWYV DGVEVHNAKT KPREEQFQST YRVVSVLTVL HQDWLNGKEY

KCKVSNKGLP SSIEKTISK KGQPREPQVY TLPPSQEEMT KNQVSLTCLV

KGFYPSDIAV EWESNGQPEN NYKTTPPVLD SDGSFFLYSR LTVDKSRWQE

GNVFSCSVMH EALHNHYTQK SLSLSLGK

IgG1(AA) CH2 domain only (mutated cysteines in hinge domain to abrogate dimerization, and mutated hinge domain to abrogate FcR binding)
(SEQ ID NO: 34)
EPKSSDKTHTSPPSPAPEAAGGPSVFLFPPKPKDTLMISRTPEVTCVVVDVS

HEDPEVKFNWYVDGVEVHNAKTKPREEQYNSTYRVVSVLTVLHQDWLNGKEYKCKV

SNKALPAPIEKTISKAKGQPRE

IgG2(AA) CH2 domain only (mutated cysteines in hinge domain to abrogate dimerization, and mutated hinge domain to abrogate FcR binding).
(SEQ ID NO: 35)
ERKCCVECPPCPAPPAAAPSVFLFPPKPKDTLMISRTPEVTCVVVD

VSHEDPEVQFNWYVDGVEVHNAKTKPREEQFNSTFRVVSVLTVVHQDWLNGKEYKCK

VSNKGLPAPIEKTISKTKGQPRE

IgG1 wildtype sequence
(SEQ ID NO: 36)
EP KSCDKTHTCP PCPAPELLGG PSVFLFPPKP KDTLMISRTP

EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

IgG4 wildtype sequence
(SEQ ID NO: 37)
ESKYGPPCPSCP APEFLGGPSV FLFPPKPKDT LMISRTPEVT

CVVVDVSQED

PEVQFNWYVD GVEVHNAKTK PREEQFNSTY RVVSVLTVLH QDWLNGKEYK

```
CKVSNKGLPS SIEKTISKAK GQPREPQVYT LPPSQEEMTK NQVSLTCLVK

GFYPSDIAVE WESNGQPENN YKTTPPVLDS DGSFFLYSRL TVDKSRWQEG

NVFSCSVMHE ALHNHYTQKS LSLSLGK
```

D. Composition Molecules and Vectors

Embodiments of the disclosure encompass compositions that comprise at least one molecule that comprises at least one liver antigen-targeting entity. Embodiments of the disclosure also encompass compositions that comprise at least one molecule that comprises at least one immunostimulatory entity. Embodiments of the disclosure encompass compositions that comprise at least one molecule that comprises both of at least one liver antigen-targeting entity and at least one immunostimulatory entity. In specific embodiments the molecule also comprises a linker that connects at least one liver antigen-targeting entity and at least one immunostimulatory entity. In cases wherein more than one entity of any kind are comprised on the same molecule, they are operably linked such that the more than one entity is capable of performing their respective functions, for example in conjunction with one another.

In some cases, the molecule comprising the one or more liver antigen-targeting entities and/or the one or more immunostimulatory entities is a polynucleotide, including DNA or RNA. When two or more entities are on a polynucleotide molecule, the regulation of expression of the two or more entities may be coordinated, such as being the same element(s), for example, or they may utilize different regulatory elements for regulation of expression. A "regulatory element" as used herein refers to one or more transcriptional control elements, such as non-coding cis-acting transcriptional control elements, capable of regulating and/or controlling transcription of an RNA from a coding region, in particular tissue-specific transcription. Regulatory elements may comprise at least one transcription factor binding site, more in particular at least one binding site for a tissue-specific transcription factor, most particularly at least one binding site for a liver-specific transcription factor. Regulatory elements may comprise enhancer sequences. Regulatory elements may be situated either upstream (e.g. in the promoter region) or downstream (e.g. in the 3' UTR) of the sequence they regulate in vivo, and may be located in the immediate vicinity of the gene or further away. In specific aspects, one or more regulatory elements on the polynucleotide are tissue-specific, such as liver-specific regulatory sequences, for example. Examples of liver tissue-specific regulatory elements include at least 1) thyroxine binding globulin (TBG) promoter; and/or 2) a regulatory element as described in US 2011/0184049, 3) albumin enhancer/promoter, 4) apoE promoter, 5) alpha1-antitrypsin promoter, 6) HBV core promoter; and 7) combinations thereof.

In particular embodiments, a polynucleotide that expresses two or more entities of any kind is configured such that the two or more entities are expressed as a fusion protein.

In specific examples, the polynucleotide encodes a sequence that allows the expressed polypeptide to be secretable from a cell, such as a leader sequence. The leader sequence is configured on the fusion protein appropriately so that any cell in which the polynucleotide resides may express the polypeptide and allow the polypeptide to become secreted so that it may act upon other cells, for example. In specific embodiments, the leader sequence is about 5-30 amino acids long and is present at the N-terminus of the fusion protein. In at least some cases, a core of the leader sequence (which may also be referred to as a signal peptide) contains a long stretch of hydrophobic amino acids that has a tendency to form a single alpha-helix. Examples in amino acid format include but are not limited to the following:

```
                                        (SEQ ID NO: 22)
            MDWIWRILFLVGAATGAHS, (SEQ ID NO: 23)
            MALPVTALLLPLALLLHAARP,
or
                                        (SEQ ID NO: 24)
            MEFGLSWLFLVAILKGVQCSR.
```

In some cases, a polynucleotide comprises at least one liver antigen-targeting entity and/or at least one immunostimulatory entity and in a 5' to 3' direction on the polynucleotide each of the entities (and more entities, where applicable) may be in any order so long as they are capable of performing their respective function. In specific cases, in a 5' to 3' direction on the polynucleotide, the order on the molecule may be as follows, for example:

a) liver antigen-targeting entity---immunostimulatory entity;

b) liver antigen-targeting entity---linker---immunostimulatory entity;

c) immunostimulatory entity---liver antigen-targeting entity; or d) immunostimulatory entity---linker---liver antigen-targeting entity.

e) immunostimulatory entity---linker f) immunostimulatory entity

In specific cases, when the molecule encodes a bispecific antibody, the order on the molecule in a 5' to 3' direction may be as follows, for example:

a) scFv (liver antigen-targeting entity)---scFv (immunostimulatory entity);

b) scFv (liver antigen-targeting entity)---linker---scFv (immunostimulatory entity);

c) scFv (immunostimulatory entity)---scFv (liver antigen-targeting entity); or d) scFv (immunostimulatory entity)---linker---scFv (liver antigen-targeting entity)

In specific cases, when the molecule comprises a cytokine, the order on the molecule in a 5' to 3' direction may be as follows, for example:

a) scFv (liver antigen-targeting entity)---cytokine;

b) scFv (liver antigen-targeting entity)---linker---cytokine;

c) cytokine---scFv (liver antigen-targeting entity); or d) cytokine---linker---scFv (liver antigen-targeting entity)

In specific embodiments, the molecule comprising the one or more liver antigen-targeting entities and/or the one or more immunostimulatory entities is a polypeptide. In particular embodiments, the polypeptide is secretable.

In particular embodiments, the polynucleotides and/or polypeptides encompassed by the disclosure are provided to an individual in naked form. However, in other embodiments the polynucleotides and/or polypeptides encompassed by the disclosure are configured in and/or on a vector. The vector may of any kind and in at least some cases acts to protect the polynucleotide and/or polypeptide of which it contains, or is attached to, from one or more deleterious events and/or environments (such as nucleases or proteases, respectively), for example. Any viral or non-viral vector may be used in vivo or ex vivo to deliver the polynucleotides into target cells, including liver cells, such as liver diseased cells that includes pathogen-infected cells and tumor cells and/or cells within the tumor microenvironment. This includes, but is not limited to, adenovirus (replication competent, replication incompetent, helper dependent), adeno associated virus (AAV) (see, for example, US 2002/0151509, which is incorporated by reference herein in its entirety), Herpes simplex virus 1 (HSV1), myxoma virus, reovirus, poliovirus, vesicular stomatitis virus (VSV), measles virus (MV), Newcastle disease virus (NDV), retroviruses, nanoparticles, cationic lipids, cationic polymers, lipid nanoparticles, liposomes and/or lipid polymers, for example. The polynucleotide may be generated as part of the same molecule as a vector, the polynucleotide may be encompassed within a vector, and/or the polynucleotide may be attached to a vector, as examples.

Thus, the vector may be viral or non-viral, in certain cases. A non-viral vector may comprise a plasmid, liposomes, nanoparticles, microbubble plus ultrasound, dendrimers, cationic magnetic nanoparticles, lipoplexes (lipid-based); inorganic molecules, etc. A viral vector may be of any kind, but in specific embodiments the viral vector is an adenoviral vector, an adeno-associated viral vector, a retroviral vector, or a lentiviral vector. In specific cases, a viral vector may comprise one or more modifications that change a property of the viral vector. In cases wherein the viral vector is an adeno-associated viral vector, the adeno-associated virus may comprise one or more modifications that change a property of the adeno-associated virus, such as a capsid mutation, for example, that renders it to preferentially transduce a target tissue or organ, such as a liver. An adeno-associated viral vector may be utilized in some cases because it preferentially transduces a certain target tissue or organ, such as a liver. In specific embodiments, the adeno-associated viral vector is of the serotype AAV1, AAV2, AAV3, AAV4, AAV5, AAV6, AAV7, AAV8, AAV9, AAV10, AAV11, AAV12, or an AAV serotype isolated from a non-human primate.

In specific cases, when the polynucleotide is RNA, such as mRNA, the vector may comprise a lipid-based nanoparticle. In certain cases wherein the polynucleotide is an mRNA, it may or may not comprise one or more modified nucleotides (i.e., with additional chemical groups behind canonical ribonucleotides, with pseudouridine and 5-methylcytosine being examples) that increase translation and/or inhibit the innate immune response in an individual being provided the mRNA. In preferred embodiments, the mRNA molecule contains one or more of, or all of, a 5' guanosine cap, a 5' UTR, the open reading frame, a 3' UTR, and a polyA tail. The sequence of the 3' UTR may be manipulated to add sequences targeted by host miRNA's, thereby offered a level of expression control to either diseased cells or to normal cells.

In specific embodiments, a vector comprises at least one expression construct that encodes a molecule that comprises at least one liver antigen-targeting entity and at least one immunostimulatory entity. An expression construct may comprise coding regions that encode the at least one liver antigen-targeting entity and the at least one immunostimulatory entity, and in some cases the entities are regulated in the expression construct by one or more regulatory regions. Although in certain cases they share at least one regulatory region, such as by being expressed as a fusion protein, in alternative cases they utilize different regulatory regions. In any case, a regulatory region in the expression cassette may be tissue-specific, including liver-specific.

The non-natural polynucleotide and/or polypeptide compositions encompassed by the disclosure may be manufactured by any suitable means. In specific embodiments, they are generated using standard recombination means in the art. Basic procedures for constructing recombinant DNA and RNA molecules in accordance with the present disclosure are disclosed in numerous publications, including Sambrook et al., In: Molecular Cloning: A Laboratory Manual, Second Edition, Cold Spring Harbor Press, Cold Spring Harbor, N.Y. (1989), which is herein incorporated by reference. In particular cases, the compositions are stored under suitable conditions and provided to an individual (including through a medical practitioner) at a time of need.

E. Specific Examples of Compositions

Particular examples of compositions having specific scFvs and linkers are as follows:

```
19-Fc-CD3:  Leader-scFv XTL19-IgG1 Fc domain-OKT3 scFv binding
human CD3
                                                          (SEQ ID NO: 15)
MDWIWRILFL  VGAATGAHSQ  VQLVESGGGV  VQPGGSLRLS  CAPSGFVFRS

YGMHWVRQTP  GKGLEWVSLI  WHDGSNRFYA  DSVKGRFTIS  RDNSKNTLYL

QMNSLRAEDT  AMYFCARERL  IAAPAAFDLW  GQGTLVTVSS  GGGGSGGGGS

GGGGSSYVLT  QPPSVSVAPG  KTARISCGGN  NIGTKNVHWY  QQKPGQAPVL

VVYADSDRPS  GIPERFSGSN  SGNTATLTIS  RVEVGDEADY  YCQVWDSVSY

HVVFGGGTTL  TVLGSGGGGS  DKTHTCPPCP  APELLGGPSV  FLFPPKPKDT

LMISRTPEVT  CVVVDVSHED  PEVKFNWYVD  GVEVHNAKTK  PREEQYNSTY

RVVSVLTVLH  QDWLNGKEYK  CKVSNKALPA  PIEKTISKAK  GQPREPQVYT

LPPSRDELTK  NQVSLTCLVK  GFYPSDIAVE  WESNGQPENN  YKTTPPVLDS

DGSFFLYSKL  TVDKSRWQQG  NVFSCSVMHE  ALHNHYTQKS  LSLSPGKSSD
```

-continued

```
IKLQQSGAEL ARPGASVKMS CKTSGYTFTR YTMHWVKQRP GQGLEWIGYI

NPSRGYTNYN QKFKDKATLT TDKSSSTAYM QLSSLTSEDS AVYYCARYYD

DHYCLDYWGQ GTTLTVSSGG GGSGGGGSGG GGSDIQLTQS PAIMSASPGE

KVTMTCRASS SVSYMNWYQQ KSGTSPKRWI YDTSKVASGV PYRFSGSGSG

TSYSLTISSM EAEDAATYYC
```

19-mFc-CD3: Leader-scFv XTL19-human IgG1 Fc domain with mutations
for monomeric form and for abrogated Fc receptor binding-OKT3 scFv
binding human CD3
                                                          (SEQ ID NO: 16)

```
MDWIWRILFL VGAATGAHSQ VQLVESGGGV VQPGGSLRLS CAPSGFVFRS

YGMHWVRQTP GKGLEWVSLI WHDGSNRFYA DSVKGRFTIS RDNSKNTLYL

QMNSLRAEDT AMYFCARERL IAAPAAFDLW GQGTLVTVSS GGGGSGGGGS

GGGGSSYVLT QPPSVSVAPG KTARISCGGN NIGTKNVHWY QQKPGQAPVL

VVYADSDRPS GIPERFSGSN SGNTATLTIS RVEVGDEADY YCQVWDSVSY

HVVFGGGTTL TVLGSGGGGS GAPPVAGPSV FLFPPKPKDT LMISRTPEVT

CVVVGVSHED PEVKFNWYVD GVEVHNAKTK PREEQYQSTY RVVSVLTVLH

QDWLNGKEYK CAVSNKQLPS SIEKTISKAK GQPREPQVYT KPPSRDELTK

NQVSLSCLVK GFYPSDIAVE WESNGQPENN YKTTVPVLDS DGSFRLASYL

TVDKSRWQQG NVFSCSVMHE ALHNHYTQKS LSLSPGKGSG GGGSDIKLQQ

SGAELARPGA SVKMSCKTSG YTFTRYTMHW VKQRPGQGLE WIGYINPSRG

YTNYNQKFKD KATLTTDKSS STAYMQLSL TSEDSAVYYC ARYYDDHYCL

DYWGQGTTLT VSSGGGGSGG GGSGGGGSDI QLTQSPAIMS ASPGEKVTMT

CRASSSVSYM NWYQQKSGTS PKRWIYDTSK VASGVPYRFS GSGSGTSYSL

TISSMEAEDA ATYYCQQWSS
```

19-G4m-CD3: Leader-scFv XTL19-human IgG4 Fc domain with
abrogated Fc receptor binding-OKT3 scFv binding human CD3
                                                          (SEQ ID NO: 17)

```
MDWIWRILFL VGAATGAHSQ VQLVESGGGV VQPGGSLRLS CAPSGFVFRS

YGMHWVRQ TPGKGLEWVS LIWHDGSNRF YADSVKGRFT ISRDNSKNTL

YLQMNSLR AEDTAMYF CARERLIAAP AAFDLWGQGT LVTVSSGGGG

SGGGGSGGGG SSYVLTQPPS VSVAPGKTAR ISCGGNNIGT KNVHWYQQKP

GQAPVLVVYA DSDRPSGIPE RFSGSNSGNT ATLTISRVEV GDEADYYCQV

WDSVSYHVVF GGGTTLTVLGS GGGGSESKY GPPCPSCPAP PVAGPSVFLF

PPKPKDTLM ISRTPEVTC VVVDVSQEDP EVQFNWYVDG VEVHNAKTKP

REEQFQSTYR VVSVLTVLHQ DWLNGKEYKC KVSNKGLPSS IEKTISKAKG

QPREPQVYTL PPSQEEMT KNQVSLTCLV KGFYPSDIAV EWESNGQPEN

NYKTTPPVLD SDGSFFLYSR LTVDKSRWQE GNVFSCSVM HEALHNHYT

QKSLSLSPGK GSGGGGSDIK LQQSGAELAR PGASVKMSCK TSGYTFTRYT

MHWVKQRPGQ GLEWIGYINP SRGYTNYNQK FKDKATLTTD KSSSTAYMQL
```

19-CD3: Leader-scFv XTL19-short glycine serine linker-OKT3 scFv
binding human CD3
                                                          (SEQ ID NO: 18)

```
MDWIWRILFL VGAATGAHSQ VQLVESGGGV VQPGGSLRLS CAPSGFVFRS

YGMHWVRQTP GKGLEWVSLI WHDGSNRFYA DSVKGRFTIS RDNSKNTLYL

QMNSLRAEDT AMYFCARERL IAAPAAFDLW GQGTLVTVSS GGGGSGGGGS
```

-continued

GGGGSSYVLT QPPSVSVAPG KTARISCGGN NIGTKNVHWY QQKPGQAPVL

VVYADSDRPS GIPERFSGSN SGNTATLTIS RVEVGDEADY YCQVWDSVSY

HVVFGGGTTL TVLGSGGGGS DIKLQQSGAE LARPGASVKM SCKTSGYTFT

RYTMHWVKQR PGQGLEWIGY INPSRGYTNY NQKFKDKATL TTDKSSSTAY

MQLSSLTSED SAVYYCARYY DDHYCLDYWG QGTTLTVSSG GGGSGGGGSG

GGGSDIQLTQ SPAIMSASPG EKVTMTCRAS SSVSYMNWYQ QKSGTSPKRW

IYDTSKVASG VPYRFSGSGS GTSYSLTISS MEAEDAATYY CQQWSSNPLT

FGAGTKLELK S

CD3-Fc-19: Leader-OKT3 scFv binding human CD3-IgG1 Fc domain-
scFv XTL19
(SEQ ID NO: 19)
MDWIWRILFL VGAATGAHSD IKLQQSGAEL ARPGASVKMS CKTSGYTFTR

YTMHWVKQRP GQGLEWIGYI NPSRGYTNYN QKFKDKATLT TDKSSSTAYM

QLSSLTSEDS AVYYCARYYD HYCLDYWGQ GTTLTVSSGG GGSGGGGSGG

GGSDIQLTQS PAIMSASPGE KVTMTCRASS SVSYMNWYQQ KSGTSPKRWI

YDTSKVASGV PYRFSGSGSG TSYSLTISSM EAEDAATYYC QQWSSNPLTF

GAGTKLELKS SGGGGSDKTH TCPPCPAPEL LGGPSVFLFP PKPKDTLMIS

RTPEVTCVVV DVSHEDPEVK FNWYVDGVEV HNAKTKPREE QYNSTYRVVS

VLTVLHQDWL NGKEYKCKVS NKALPAPIEK TISKAKGQPR EPQVYTLPPS

RDELTKNQVS LTCLVKGFYP SDIAVEWESN GQPENNYKTT PPVLDSDGSF

FLYSKLTVDK SRWQQGNVFS CSVMHEALHN HYTQKSLSLS PGKSSDIQVQ

LVESGGGVVQ PGGSLRLSCA PSGFVFRSYG MHWVRQTPGK GLEWVSLIWH

DGSNRFYADS VKGRFTISRD NSKNTLYLQM NSLRAEDTAM YFCARERLIA

APAAFDLWGQ GTLVTVSSGG GGSGGGGSGG GGSSYVLTQP PSVSVAPGKT

ARISCGGNNI GTKNVHWYQQ KPGQAPVLVV YADSDRPSGI PERFSGSNSG

NTATLTISRV EVGDEADYYC

CD3-B7.1-19: Leader-OKT3 scFv binding human CD3-human CD80
ectodomain-scFv XTL19
(SEQ ID NO: 20)
MDWIWRILFL VGAATGAHSD IKLQQSGAEL ARPGASVKMS CKTSGYTFTR

YTMHWVKQRP GQGLEWIGYI NPSRGYTNYN QKFKDKATLT TDKSSSTAYM

QLSSLTSEDS AVYYCARYYD HYCLDYWGQ GTTLTVSSGG GGSGGGGSGG

GGSDIQLTQS PAIMSASPGE KVTMTCRASS SVSYMNWYQQ KSGTSPKRWI

YDTSKVASGV PYRFSGSGSG TSYSLTISSM EAEDAATYYC QQWSSNPLTF

GAGTKLELKS SGGGGSPYLN FFQLLVLAGL SHFCSGVIHV TKEVKEVATL

SCGHNVSVEE LAQTRIYWQK EKKMVLTMMS GDMNIWPEYK NRTIFDITNN

LSIVILALRP SDEGTYECVV LKYEKDAFKR EHLAEVTLSV KADFPTPSIS DFEIPTSNIR

RIICSTSGGF PEPHLSWLEN GEELNAINTT VSQDPETELY AVSSKLDFNM

TTNHSFMCLI KYGHLRVNQT FNSSDIQVQL VESGGGVVQP GGSLRLSCAP

SGFVFRSYGM HWVRQTPGKG LEWVSLIWHD GSNRFYADSV KGRFTISRDN

SKNTLYLQMN SLRAEDTAMY FCARERLIAA PAAFDLWGQG TLVTVSSGGG

GSGGGGSGGG GSSYVLTQPP SVSVAPGKTA RISCGGNNIG TKNVHWYQQK

PGQAPVLVVY ADSDRPSGIP ERFSGSNSGN TATLTISRVE VGDEADYYCQ

VWDSVSYHVV

-continued

CD3-B7.1-G4m-19: Leader-OKT3 scFv binding human CD3-human
CD80 ectodomain-human IgG4 Fc domain with abrogated Fc receptor
binding-scFv XTL19

(SEQ ID NO: 21)

MDWIWRILFL VGAATGAHSD IKLQQSGAEL ARPGASVKMS CKTSGYTFTR

YTMHWVKQRP GQGLEWIGYI NPSRGYTNYN QKFKDKATLT TDKSSSTAYM

QLSSLTSEDS AVYYCARYYD DHYCLDYWGQ GTTLTVSSGG GGSGGGGSGG

GGSDIQLTQS PAIMSASPGE KVTMTCRASS SVSYMNWYQQ KSGTSPKRWI

YDTSKVASGV PYRFSGSGSGT SYSLTISSM EAEDAATYYC QQWSSNPLTF

GAGTKLELKS SGGGGSPYLN FFQLLVLAGL SHFCSGVIHV TKEVKEVATL

SCGHNVSVEE LAQTRIYWQK EKKMVLTMMS GDMNIWPEYK NRTIFDITNN

LSIVILALRP SDEGTYECVV LKYEKDAFKR EHLAEVTLSV KADFPTPSIS DFEIPTSNIR

RIICSTSGGF PEPHLSWLEN GEELNAINTT VSQDPETELY AVSSKLDFNM

TTNHSFMCLI KYGHLRVNQT FNSGGGSESK YGPPCPSCPA PPVAGPSVFL

FPPKPKDTLM ISRTPEVTCV VVDVSQEDPE VQFNWYVDGV EVHNAKTKPR

EEQFQSTYRV VSVLTVLHQD WLNGKEYKCK VSNKGLPSSI EKTISKAKGQ

PREPQVYTLP PSQEEMTKNQ VSLTCLVKGF YPSDIAVEWE SNGQPENNYK

TTPPVLDSDG SFFLYSRLTV DKSRWQEGNV FSCSVMHEAL HNHYTQKSLS

LSPGKSSDIQ VQLVESGGGV VQPGGSLRLS CAPSGFVFRS YGMHWVRQTP

GKGLEWVSLI WHDGSNRFYA DSVKGRFTIS RDNSKNTLYL QMNSLRAEDT

AMYFCARERL IAAPAAFDLW GQGTLVTVSS GGGGSGGGGS GGGGSSYVLT

QPPSVSVAPG KTARISCGGN NIGTKNVHWY QQKPGQAPVL VVYADSDRPS

GIPERFSGSN SGNTATLTIS RVEVGDEADY YCQVWDSVSY HVVFGGGTTL

Leader-19-mFc-hCD3 = 19.45.9 or XTL-19 scFv-IgG1m CH2-CH3
domain with Fc mutation-humanized OKT3 (gOKT3-7)

(SEQ ID NO: 38)

MDWIWRILFL VGAATGAHSQ VQLVESGGGV VQPGGSLRLS CAPSGFVFRS

YGMHWVRQTP GKGLEWVSLI WHDGSNRFYA DSVKGRFTIS RDNSKNTLYL

QMNSLRAEDT AMYFCARERL IAAPAAFDLW GQGTLVTVSS GGGGSGGGGS

GGGGSSYVLT QPPSVSVAPG KTARISCGGN NIGTKNVHWY QQKPGQAPVL

VVYADSDRPS GIPERFSGSN SGNTATLTIS RVEVGDEADY YCQVWDSVSY

HVVFGGGTTL TVLGEPKSCD KTHTCPPCPA PEAAGGPSVF LFPPKPKDTL

MISRTPEVTC VVVDVSHEDP EVKFNWYVDG VEVHNAKTKP REEQYQSTYR

VVSVLTVLHQ DWLNGKEYKC KVSNKALPAP IEKTISKAKG QPREPQVYTL

PPSRDELTKN QVSLTCLVKG FYPSDIAVEW ESNGQPENNY KTTPPVLDSD

GSFFLYSKLT VDKSRWQQGN VFSCSVMHEA LHNHYTQKSL SLSPGKSGSG

SQVQLVQSGG GVVQPGRSLR LSCKASGYTF TRYTMHWVRQ APGKGLEWIG

YINPSRGYTN YNQKVKDRFT ISRDNSKNTA FLQMDSLRPE DTGVYFCARY

YDDHYCLDYW GQGTPVTVSS GGGGSGGGGS GGGGSDIQMT QSPSSLSASV

GDRVTITCSA SSSVSYMNWY QQTPGKAPKR WIYDTSKLAS GVPSRFSGSG

SGTDYTFTIS SLQPEDIATY YCQQWSSNPF TFGQGTKLQI TR

-continued

Leader-19-mFc = 19.45.9 or XTL-19 scFv-IgG1m CH2-CH3 domain
with Fc mutation
(SEQ ID NO: 39)

MDWIWRILFL VGAATGAHSQ VQLVESGGGV VQPGGSLRLS

CAPSGFVFRS YGMHWVRQTP GKGLEWVSLI WHDGSNRFYA DSVKGRFTIS

RDNSKNTLYL QMNSLRAEDT AMYFCARERL IAAPAAFDLW GQGTLVTVSS

GGGGSGGGGS GGGGSSYVLT QPPSVSVAPG KTARISCGGN NIGTKNVHWY

QQKPGQAPVL VVYADSDRPS GIPERFSGSN SGNTATLTIS RVEVGDEADY

YCQVWDSVSY HVVFGGGTTL TVLGEPKSCD KTHTCPPCPA PEAAGGPSVF

LFPPKPKDTL MISRTPEVTC VVVDVSHEDP EVKFNWYVDG VEVHNAKTKP

REEQYQSTYR VVSVLTVLHQ DWLNGKEYKC KVSNKALPAP IEKTISKAKG

QPREPQVYTL P SRDELTKN QVSLTCLVKG FYPSDIAVEW ESNGQPENNY

KTTPPVLDSD GSFFLYSKLT VDKSRWQQGN VFSCSVMHEA LHNHYTQKSL SLSPGK
496

Leader-19-hCD3 = 19.79.5 or XTL-19 scFv-humanized OKT3
(gOKT3-7)
(SEQ ID NO: 40)

MDWIWRILFL VGAATGAHSQ VQLVESGGGV VQPGGSLRLS

CAPSGFVFRS YGMHWVRQTP GKGLEWVSLI WHDGSNRFYA DSVKGRFTIS

RDNSKNTLYL QMNSLRAEDT AMYFCARERL IAAPAAFDLW GQGTLVTVSS

GGGGSGGGGS GGGGSSYVLT QPPSVSVAPG KTARISCGGN NIGTKNVHWY

QQKPGQAPVL VVYADSDRPS GIPERFSGSN SGNTATLTIS RVEVGDEADY

YCQVWDSVSY HVVFGGGTTL TVLGSGGGGS VQLVQSGGGV VQPGRSLRLS

CKASGYTFTR YTMHWVRQAP GKGLEWIGYI NPSRGYTNYN QKVKDRFTIS

RDNSKNTAFL QMDSLRPEDT GVYFCARYYD DHYCLDYWGQ GTPVTVSSGG

GGSGGGGSGG GGSDIQMTQS PSSLSASVGD RVTITCSASS SVSYMNWYQQ

TPGKAPKRWI YDTSKLASGV PSRFSGSGSG TDYTFTISSL QPEDIATYYC

QQWSSNPFTF GQGTKLQITR

Leader-17-mFc-hCD3 = 17.1.41 or XTL-17 scFv-IgG1m CH2-CH3
domain with Fc mutation-humanized OKT3 (gOKT3-7)
(SEQ ID NO: 41)

MDWIWRILFL VGAATGAHSQ VQLVESGGGV VRPGRSLRLS

CAASGFAFSD YSINWVRQAP GKGLEWVAII SYDGRITYYR DSVKGRFTIS

RDDSKNTLYL QMNSLRTEDT AVYYCARQYY DFWSGSSVGR NYDGMDVWGL

GTTVTVSSGG GGSGGGGSGG GGSDIVMTQS PLSLSVTPGE PASISCRSSQ

SLLHRSGNNY LDWYLQKPGH SPQLLIYVGS NRASGVPDRF SGSGSGTEYT

LRISTVEAED VGVYYCMQAL QTPRTFGQGT KLEIKREPKS CDKTHTCPPC

PAPEAAGGPS VFLFPPKPKD TLMISRTPEV TCVVVDVSHE DPEVKFNWYV

DGVEVHNAKT KPREEQYQST YRVVSVLTVL HQDWLNGKEY KCKVSNKALP

APIEKTISKA KGQPREPQVY TLPPSRDELT KNQVSLTCLV KGFYPSDIAV

EWESNGQPEN NYKTTPPVLD SDGSFFLYSK LTVDKSRWQQ GNVFSCSVMH

EALHNHYTQK SLSLSPGKSG SGSQVQLVQS GGGVVQPGRS LRLSCKASGY

TFTRYTMHWV RQAPGKGLEW IGYINPSRGY TNYNQKVKDR FTISRDNSKN

TAFLQMDSLR PEDTGVYFCA RYYDDHYCLD YWGQGTPVTV SSGGGGSGGG

GSGGGGSDIQ MTQSPSSLSA SVGDRVTITC SASSSVSYMN WYQQTPGKAP

-continued

KRWIYDTSKL ASGVPSRFSG SGSGTDYTFT ISSLQPEDIA TYYCQQWSSN

PFTFGQGTKL QITR

Leader-17-mFc = 17.1.41 or XTL-17 scFv-IgG1m CH2-CH3 domain
with Fc mutation
(SEQ ID NO: 42)

MDWIWRILFL VGAATGAHSQ VQLVESGGGV VRPGRSLRLS

CAASGFAFSD YSINWVRQAP GKGLEWVAII SYDGRITYYR DSVKGRFTIS

RDDSKNTLYL QMNSLRTEDT AVYYCARQYY DFWSGSSVGR NYDGMDVWGL

GTTVTVSSGG GGSGGGGSGG GGSDIVMTQS PLSLSVTPGE PASISCRSSQ

SLLHRSGNNY LDWYLQKPGH SPQLLIYVGS NRASGVPDRF SGSGSGTEYT

LRISTVEAED VGVYYCMQAL QTPRTFGQGT KLEIKREPKS CDKTHTCPPC

PAPEAAGGPS VFLFPPKPKD TLMISRTPEV TCVVVDVSHE DPEVKFNWYV

DGVEVHNAKT KPREEQYQST YRVVSVLTVL HQDWLNGKEY KCKVSNKALP

APIEKTISKA KGQPREPQVY TLPPSRDELT KNQVSLTCLV KGFYPSDIAV

EWESNGQPEN NYKTTPPVLD SDGSFFLYSK LTVDKSRWQQ GNVFSCSVMH

EALHNHYTQK SLSLSPGK

Leader-17-hCD3 = 17.1.41 or XTL-17 scFv-humanized OKT3
(gOKT3-7)
(SEQ ID NO: 43)

MDWIWRILFL VGAATGAHSQ VQLVESGGGV VRPGRSLRLS

CAASGFAFSD YSINWVRQAP GKGLEWVAII SYDGRITYYR DSVKGRFTIS

RDDSKNTLYL QMNSLRTEDT AVYYCARQYY DFWSGSSVGR NYDGMDVWGL

GTTVTVSSGG GGSGGGGSGG GGSDIVMTQ SPLSLSVTPGE PASISCRSSQ

SLLHRSGNNY LDWYLQKPGH SPQLLIYVGS NRASGVPDRF SGSGSGTEYT

LRISTVEAED VGVYYCMQAL QTPRTFGQGT KLEIKRSGGG GSQVQLVQSG

GGVVQPGRSL RLSCKASGYT FTRYTMHWVR QAPGKGLEWI GYINPSRGYT

NYNQKVKDRF TISRDNSKNT AFLQMDSLRP EDTGVYFCAR YYDDHYCLDY

WGQGTPVTVS SGGGGSGGGG SGGGGSDIQM TQSPSSLSAS VGDRVTITCS

ASSSVSYMNW YQQTPGKAPK RWIYDTSKLA SGVPSRFSGS GSGTDYTFTI

SSLQPEDIAT YYCQQWSSNP FTFGQGTKLQ ITR

Leader-hCD3-mFc = leader-humanized OKT3 (gOKT3-7)-mFc
(mutations in Fc domain against Fc receptor proteins)
(SEQ ID NO: 44)

MDWIWRILFL VGAATGAHSQ VQLVQSGGGV VQPGRSLRLS

CKASGYTFTR YTMHWVRQAP GKGLEWIGYI NPSRGYTNYN QKVKDRFTIS

RDNSKNTAFL QMDSLRPEDT GVYFCARYYD DHYCLDYWGQ GTPVTVSSGG

GGSGGGGSGG GGSDIQMTQS PSSLSASVGD RVTITCSASS SVSYMNWYQQ

TPGKAPKRWI YDTSKLASGV PSRFSGSGSG TDYTFTISSL QPEDIATYYC

QQWSSNPFTF GQGTKLQITR EPKSCDKTHT CPPCPAPEAA GGPSVFLFPP

KPKDTLMISR TPEVTCVVVD VSHEDPEVKF NWYVDGVEVH NAKTKPREEQ

YQSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP GK

-continued

Leader-hCD3 = leader-humanized OKT3 (gOKT3-7)

(SEQ ID NO: 45)

MDWIWRILFL VGAATGAHSQ VQLVQSGGGV VQPGRSLRLS

CKASGYTFTR YTMHWVRQAP GKGLEWIGYI NPSRGYTNYN QKVKDRFTIS

RDNSKNTAFL QMDSLRPEDT GVYFCARYYD DHYCLDYWGQ GTPVTVSSGG

GGSGGGGSGG GGSDIQMTQS PSSLSASVGD RVTITCSASS SVSYMNWYQQ

TPGKAPKRWI YDTSKLASGV PSRFSGSGSG TDYTFTISSL QPEDIATYYC

QQWSSNPFTF GQGTKLQITR

In particular embodiments, provided herein are specific examples of polynucleotide compositions that encode at least one liver antigen-targeting entity and/or immunostimulatory entity, and/or the polypeptides themselves. In certain compositions, the liver antigen-targeting entity consists of or comprises a single chain antibody, a single chain variable fragment, a camelid antibody, or a peptide. An immunostimulatory domain may comprise an anti-CD3 scFv, an anti-CD28 scFv, anti-41BB scFv, anti-OX40 scFv, anti-CTLA4 scFv, an anti-CD16 scFv, anti-PD1 scFv, anti-PD-L1 scFv, anti-CD47 scFv, part or all of the ectodomain for a ligand for CD28 (such as part or all of the ectodomain of CD80 and/or CD86), part or all of the ectodomain of 41BB ligand, part or all of the ectodomain of the LIGHT protein, ICOS-ligand, CD276 (B7-H3), B7-H4, and B7-H6, CD134L, CD137L, or a cytokine (IL-2, IL-15, etc.).

Any of such specific compositions, or others, may reside in a vector or as part of a vector or attached thereto, for example, and in specific cases the vector is an adeno-associated virus, wherein the virus has a cassette that encodes a tissue specific promoter, in order to target expression to a specific organ. When the vector comprises messenger RNA, the mRNA may be delivered in a lipid-based nanoparticle, and any mRNA encompassed by the disclosure may have modified nucleotides to increase translation and inhibit the innate immune response.

In certain vector embodiments, there is an adeno-associated virus with a mutated capsid or serotype that preferably transduced human liver. An example is an AAV with serotype preferably AAV8 or AAV9. Some vectors may utilize the TBG promoter, for example for targeting expression of bispecific antibodies to the liver after delivery by AAV.

Bispecific antibodies that target a cell surface antigen on a diseased cell are encompassed herein, including those that at least target HBV small surface antigen, HBV middle surface antigen, HBV large surface antigen, HCV E1 protein, HCV E2 protein, EBV glycoprotein, CMV glycoprotein, EphA2, glypican-3, HER2, PSCA, TEM8, CD19, EGFRvIII, etc. In specific embodiments, there is a bispecific antibody construct that comprises on a molecule the orientation: scFv (target)-linker-scFv (immune) or scFv (immune)-linker-scFv (target). In other embodiments, there is an immunocytokine construct comprising the orientation: cytokine-linker-scFv (target) or scFv (target)-linker-cytokine.

In alternative embodiments, the composition provided to an individual comprises an immunostimulatory protein alone (i.e., anti-CD3-Fc, anti-CD3 scFv alone, anti-CD28-Fc, anti-CD28 scFv alone, or B7-Fc alone, or anti-PD1 alone) in the absence of a liver antigen-targeting entity, particularly absent on the same molecule, for example. Normally, these molecules would not be activating, but the in situ tissue expression described in this invention results in unexpected aggregation and activation properties. In other alternative embodiments, the composition comprises a protein that comprises an antigen-targeting domain alone (or a polynucleotide encoding same), and in specific embodiments the composition with the antigen-targeting domain may be used in combination with an immunostimulatory ligand.

In alternative embodiments, the composition provided to an individual comprises an additional cell protective polynucleotide sequence in addition to the disease antigen targeting and/or immune stimulatory components. The cell protective polynucleotide sequence will serve to inhibit the targeted tissue from suffering cytotoxic death amidst the induced inflammation, preventing loss of normal cells and tissue while preserving therapeutic efficacy against the pathogen or cancer. Examples of a cytoprotective agent may include an mRNA encoding the Bcl2, Bcl-XL, Mcl-1, CED-0, Bfl-1, X-linked inhibitor of apoptosis protein (XIAP), c-IAP1, C-IAP2, NAIP, Livin, Survivin, serpin proteinase inhibitor 9, or SERPINB4. Other examples include an siRNA, antisense oligonucleotide, or a morpholino targeting the knockdown of Fas receptor, TNFalpha receptor, Bax, Bid, Bak, or Bad, genes that otherwise induce apoptosis. A cytoprotective agent may be an apoptosis inhibitor, in specific cases. In some cases the secretable polypeptide and the cytoprotective agent are encoded on the same nucleic acid molecule, for example if they were regulated by separate promoters, or separated by an IRES or 2A element. In cases wherein the secretable polypeptide and cytoprotective agent are on separate nucleic acids, they can be delivered separately on two separate molecules, but packaged together in the same composition, such as a nanoparticle.

II. Methods of Use

Embodiments of the disclosure include methods of treating at least one medical condition that affects a targeted tissue, such as the liver, of a mammal, including humans, dogs, cats, horses, cows, pigs, sheep, etc. In specific embodiments, the disease is caused by a pathogen, although alternatively or additionally at least in part it may be environmental and/or genetic in nature. In specific embodiments, the method is employed for treating cancer or an infectious disease in a targeted tissue, including the liver. In specific embodiments, methods of the disclosure comprise administering RNA or DNA that encodes proteins via viral or non-viral vectors, although in alternative embodiments polypeptides are administered.

Any disease in a specific tissue that can be treated with targeted therapy may be treated with methods of the disclosure. However, in specific embodiments a liver disease is treated, including any liver disease. Viral liver diseases may be treated using targeted therapies of the disclosure, as well as cancers of the liver may be treated, including both primary and metastatic lesions. Specific liver diseases include but are not limited to Hepatitis B infection, Hepatitis A infection, Hepatitis C infection, Hepatoblastoma, Hepatocellular Carcinoma, and metastatic cancer of the breast, prostate, pancreas, colon, rectum, esophagus, stomach, lungs, kidney, or skin, as examples.

Polynucleotides of the disclosure encode fusion proteins that bind a targeted antigen and that stimulate an immune function, and the fusion protein(s) may be generated for and/or in an individual in any manner. In some cases, the polynucleotide is delivered to the individual locally such that upon delivery of the polynucleotide composition to the targeted tissue or organ in vivo, the polynucleotide is taken up by the tissue or organ, and the fusion protein is produced in those cells. Following production of the fusion protein in the cells, the cells secrete the fusion protein such that it is soluble and can bind its target(s) on other cells, including at least non-transduced cells, such as diseased cells including pathogen-infected or cancer cells.

Delivery of a composition encompassed by the disclosure may be of any kind, route, duration, recurrence, and so forth. In particular embodiments delivery of the compositions is local in nature, although in alternative embodiments the delivery is systemic. In some cases the same composition is delivered to an individual in need thereof, although in other cases different compositions are provided to an individual in need thereof, whether it occurs at the same or different times. In specific embodiments, delivery of one or more compositions to an individual in need thereof is in the absence of systemic delivery, such as in the absence of constant infusion, for example.

In some methods of the disclosure, more than one composition comprising at least one liver antigen-targeting entity and/or at least one immunostimulatory entity are provided to an individual, and in some cases the compositions are non-identical. They may be targeting different liver antigens, they may be providing immunostimulation through different targets, or both, for example. In such cases, the two or more different compositions may be provided to the individual at the same time and/or at different times. In some aspects, different compositions are provided at different times over the course of suitable durations in the span of time of delivery, including on the order of 1-60 minutes, 1-24 hours, 1-7 days, 1-4 weeks, 1-12 months, or 1 or more years. In specific cases, a non-identical composition is provided to the individual under certain treatment outcomes, such as when a particular therapy becomes refractory (for example, with primary liver or metastatic cancer). The administration of the composition(s) of the disclosure is useful for all stages and types of cancer that affects the liver (as an example), including for minimal residual disease, early cancer, advanced cancer, metastatic cancer and/or refractory cancer, for example.

Particular embodiments of methods of use include delivery of bispecific antibodies to the liver using viral DNA or non-viral RNA vectors, for example, as a platform for their expression. In specific embodiments, one can employ an off-the-shelf immunotherapy, including that having a higher safety and efficacy index than infusion of recombinant bispecific antibody therapy, for example.

By way of illustration, diseased individuals or individuals suspected of having disease or at risk therefore may be treated as described herein. The polynucleotides and/or polypeptides as described herein may be administered to the individual and retained for extended periods of time. The individual may receive one or more administrations of the polynucleotides. In some embodiments, polynucleotides are encapsulated to inhibit immune recognition and placed at the site of the tissue or organ (or tumor, for cancer embodiments).

In various embodiments the expression constructs, nucleic acid sequences, vectors, host cells and/or pharmaceutical compositions comprising the same are used for the prevention, treatment or amelioration of a liver disease. In particular embodiments, the pharmaceutical composition of the present disclosure may be particularly useful in preventing, ameliorating and/or treating disease related to the liver, including viral infection or liver cancer having solid tumors, for example.

As used herein "treatment" or "treating," includes any beneficial or desirable effect on the symptoms or pathology of a disease or pathological condition, and may include even minimal reductions in one or more measurable markers of the disease or condition being treated, e.g., pathogen infection or cancer. Treatment can involve either the reduction or amelioration of symptoms of the disease or condition and/or the delaying of the progression of the disease or condition. "Treatment" does not necessarily indicate complete eradication or cure of the disease or condition, or associated symptoms thereof.

In particular embodiments, the present disclosure contemplates, in part, polypeptides, nucleic acid molecules and/or vectors that can be administered either alone or in any combination with another therapy, and in at least some aspects, together with a pharmaceutically acceptable carrier or excipient. In certain embodiments, nucleic acid molecules or vectors may be stably integrated into the genome of the targeted cells. In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying the above identified diseases.

Furthermore, the disclosure relates to a method for the treatment or amelioration of a liver disease comprising the step of administering to a subject in need thereof an effective amount of polynucleotides, cells, and/or vector(s), as contemplated herein and/or produced by a process as contemplated herein.

In one embodiment, there is a method of making functional bi-, tri- or quadraspecific antibodies comprising administering two or more coding sequences targeting different antigens or immunostimulatory domains into an individual, wherein the proteins generated may dimerize at random generating a substantial fraction of antibodies with heterotypic partners, thereby generating antibodies with dual target specificity and/or dual immune stimulatory properties. More specifically, antibodies with Fc domains will naturally form dimers at the Fc-Fc interface. Expressing two or more antibodies in the same cell will result in random pairing of Fc domains, resulting in multiple antigen targeting within the same protein. Such proteins may be of use for higher affinity targeting of cancer or pathogen cells via targeted two antigens at one time. Similarly, one molecule targeting two immune molecules can lead to higher activation and potency. The expression of two coding sequences delivered into a specific tissue such as the liver, where one antibody targets a disease antigen and one antibody targets an immunostimatory molecule, can also more simply make bispecific antibodies in situ in the liver in addition to the monospecific antibodies from another embodiment. This is an advantageous way to make multiple different types of antibodies within a specific tissue, including bispecific antibodies that can redirect immune cells. In some embodiments, the Fc domains may have mutations to bias the pairing of two different proteins, in order to have more heterologous Fc pairing.

In one embodiment, these multiple epitope targeting antibodies can be generated in vivo in the liver tissue. Multiple different sequences are infused at substantially the same time targeting multiple different epitopes into the liver, leading a fraction of their Fc domains to bind to each other. As applied to the treatment of Hepatitis B virus, for example, scFv's targeting a conformation and/or linear epitopes on small surface antigen and/or epitopes in the PreS1 domain of surface antigen, could be combined into a single protein of two polypeptide chains and two specificities, and thus greater affinity. Alternatively, an antibody targeting HBV surface antigen and an antibody targeting CD3 can be expressed in the liver, generating Fc dimerization and generation of a mixture anti-HBsAg antibody, anti-CD3 antibody, and bispecific anti-HBsAg/CD3-Fc antibodies. Mutations in the Fc domains (ex: knob-in-hole designs) can facilitate more heterologous Fc chain pairing.

The disclosure further encompasses co-administration protocols with other compounds, e.g. bispecific antibody constructs, targeted toxins or other compounds, which act via immune cells, although in specific cases the additional therapy does not act via immune cells. The clinical regimen for co-administration of the inventive compound(s) may encompass co-administration at the same time, before and/or after the administration of the other component. Particular combination therapies include reverse transcriptase inhibitors targeting HBV (example: lamivudine, adefovir, dipivoxil, telbivudine, tenofovir alafenamide, tenofovir, and entecavir); Interferon alfa-2b, pegylated interferon, chemotherapy, radiation, surgery, hormone therapy, arterial embolization, or other types of immunotherapy. In certain embodiments, compositions of the disclosure are utilized in liver transplant, for example with administration to the liver graft prior to transplantation, in the cadaveric donor, perfused into the excised organ, and/or given to the liver recipient.

Embodiments relate to a kit comprising one or more polynucleotides as described herein, one or more polypeptides as described herein, and/or a vector as described herein. It is also contemplated that the kit of this disclosure comprises a pharmaceutical composition as described herein, either alone or in combination with further medicaments to be administered to an individual in need of medical treatment or intervention.

The polynucleotide introduction need not result in integration in most cases. In many situations, transient maintenance of the polynucleotide introduced may be sufficient. In this way, one could have a short term effect, where gene vector could be introduced into the host at a local site or organ and after introduction, then turned off, for example, after inflammation has been induced at a particular site. In the case of mRNA modality for protein expression, the natural half-life of the molecule limits expression to 48-72 hours at most, in some embodiments.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient each patient would be monitored for the proper dosage for the individual, and such practices of monitoring a patient are routine in the art. Furthermore, monitoring of tissue damage and toxicities is also envisioned, such as alanine aminotransferase (ALT) and aspartate aminotransferase (AST) measurements for liver toxicity, and are routine clinical measurements well known in the art.

III. Pharmaceutical Compositions

In accordance with this disclosure, the term "pharmaceutical composition" relates to a composition for administration to an individual. In specific aspects of the disclosure, the pharmaceutical composition comprises a polynucleotide that encodes a polypeptide that comprises at least one immunostimulatory entity and/or at least one liver antigen-targeting entity and/or the encoded polypeptide thereof. In a particular embodiment, the pharmaceutical composition comprises a composition for parenteral, transdermal, intraluminal, intraarterial, intrathecal or intravenous administration or for direct injection into a cancer. It is in particular envisaged that the pharmaceutical composition is administered to the individual via infusion or injection. Administration of the suitable compositions may be effected by different ways, e.g., by intravenous, subcutaneous, intraperitoneal, intramuscular, topical or intradermal administration, and in alternative embodiments it occurs by infusion (such as catheter-based infusion), such as hepatic artery or portal vein infusion. In specific embodiments for hepatic artery infusion, the infusion is not constant; the infusion may occur 1, 2, 3, 4, 5, 6, 7, 8, 9, 10, 11, 12, or more times, in specific embodiments, including within a specific and suitable time frame.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The compositions of the disclosure may be administered locally, although in alternative embodiments it is administered systemically, so long as it does not elicit harmful side effects. Administration may generally be parenteral, e.g., intravenous; DNA may also be administered directly to the target site, e.g., by biolistic delivery to an internal or external target site or by catheter to a site in an artery. In one embodiment, the pharmaceutical composition is administered subcutaneously and in another embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the constructs or nucleic acid molecules or vectors encoding the same (as described in this disclosure), further biologically active agents, depending on the intended use of the pharmaceutical composition.

The dosing amounts may follow closely with previously established clinical parameters in humans and primates for achieving high transduction of hepatocytes. An example of AAV gene therapy vector dosing may be 1 to $9 \times 10^{12}$ vector genomes/kg intravenous infusion for targeting to the liver. For mRNA delivery by lipid nanoparticle to the liver, an example of a dose of 0.025 mg/kg to 0.250 mg/kg mRNA per injection can be infused intravenously in nanoparticles for efficient delivery to the majority of hepatocytes. Multiple dosing cycles are envisioned as necessary to fulfill therapeutic efficacy.

IV. Lipid Formulations

In particular embodiments of the disclosure, one or more compositions are formulated in a lipid formulation. In specific embodiments, a lipid-based nanoparticle is employed for one or more compositions. In particular cases, a vector comprising nucleic acid that encodes a composition of interest, such as the nucleic acid being messenger RNA, may be delivered in a lipid-based nanoparticle.

In some embodiments, according to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of or greater than about 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contain a mixture of desired lipids including one or more cationic lipids, one or more helper lipids (e.g. non cationic lipids and/or cholesterol lipids) and one or more PEGylated lipids.

A. Cationic Lipids

As used herein, the phrase "cationic lipids" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference.

In some embodiments, cationic lipids suitable for the compositions and methods of the invention include a cationic lipid described in WO 2015/184256 A2 entitled "Biodegradable lipids for delivery of nucleic acids" which is incorporated by reference herein such as 3-(4-(bis(2-hydroxydodecyl)amino)butyl)-6-(4-((2-hydroxydodecyl)(2-hydroxyundecyl)amino)butyl)-1,4-dioxane-2, 5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2, 5-dione (Target 24).

In some embodiments, cationic lipids suitable for the compositions and methods of the invention include a cationic lipid described in WO 2013/063468 and in U.S. provisional application entitled "Lipid Formulations for Delivery of Messenger RNA", both of which are incorporated by reference herein. In some embodiments, a cationic lipid comprises a compound of formula I c1-a:

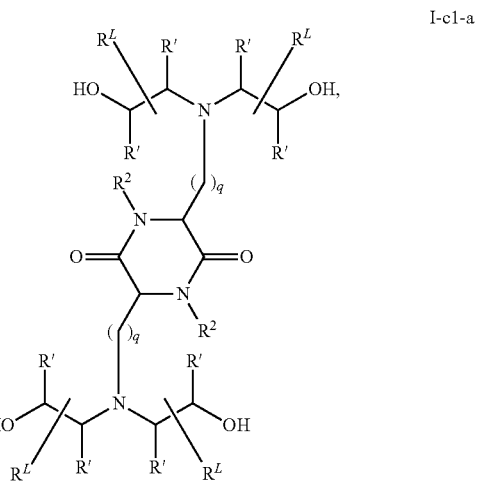

or a pharmaceutically acceptable salt thereof, wherein:

each R2 independently is hydrogen or C1 3 alkyl;

each q independently is 2 to 6;

each R' independently is hydrogen or C1 3 alkyl;

and each RL independently is C8 12 alkyl.

In some embodiments, each R2 independently is hydrogen, methyl or ethyl. In some embodiments, each R2 independently is hydrogen or methyl. In some embodiments, each R2 is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each RL independently is C8 12 alkyl. In some embodiments, each RL independently is n-C8 12 alkyl. In some embodiments, each RL independently is C9 11 alkyl. In some embodiments, each RL independently is n-C9 11 alkyl. In some embodiments, each RL independently is C10 alkyl. In some embodiments, each RL independently is n-C10 alkyl.

In some embodiments, each R2 independently is hydrogen or methyl; each q independently is 3 to 5; each R' independently is hydrogen or methyl; and each RL independently is C8 12 alkyl.

In some embodiments, each R2 is hydrogen; each q independently is 3 to 5; each R' is hydrogen; and each RL independently is C8 12 alkyl.

In some embodiments, each R2 is hydrogen; each q is 4; each R' is hydrogen; and each RL independently is C8 12 alkyl.

In some embodiments, a cationic lipid comprises a compound of formula I g:

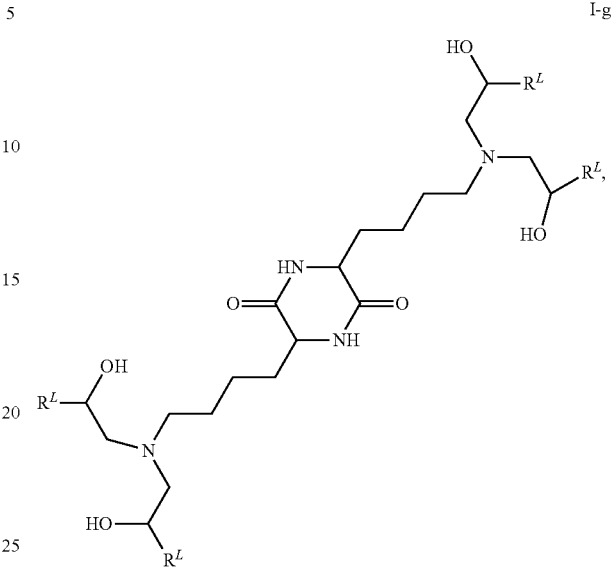

I-g or a pharmaceutically acceptable salt thereof, wherein each RL independently is C8 12 alkyl. In some embodiments, each RL independently is n-C8 12 alkyl. In some embodiments, each RL independently is C9 11 alkyl. In some embodiments, each RL independently is n-C9 11 alkyl. In some embodiments, each RL independently is C10 alkyl. In some embodiments, each RL is n-C10 alkyl.

In particular embodiments, a suitable cationic lipid is cKK-E12, or (3,6-bis(4-(bis(2-hydroxydodecyl)amino)butyl)piperazine-2,5-dione). Structure of cKK-E12 is shown below:

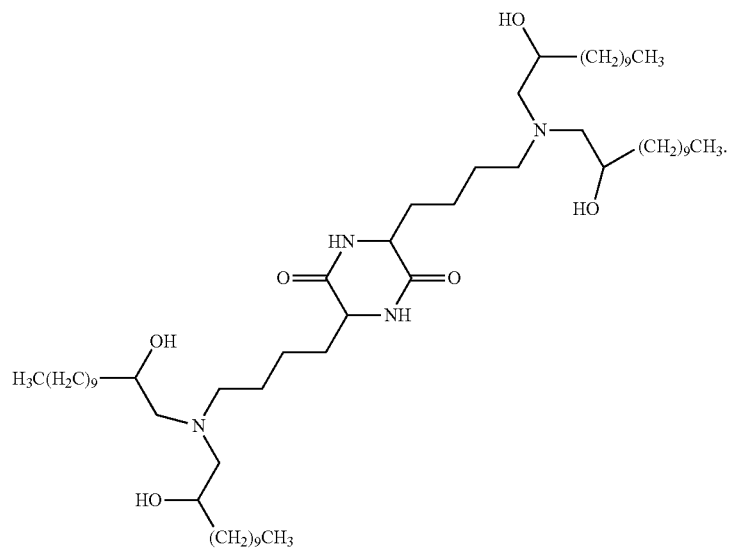

Additional exemplary cationic lipids include those of formula I:

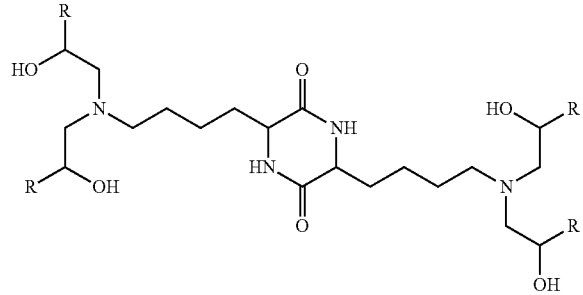

and pharmaceutically acceptable salts thereof, wherein,

R is

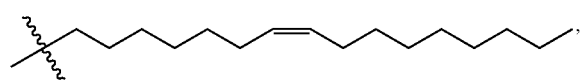 ("OF-00")

R is

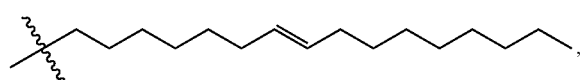 ("OF-01")

R is or

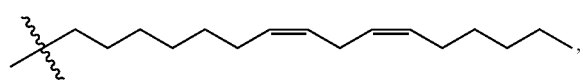 ("OF-02")

R is

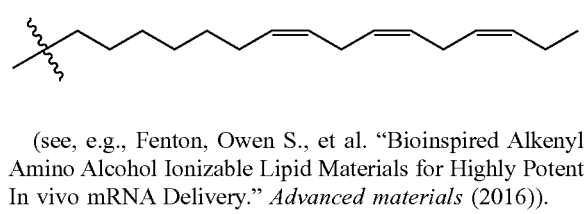 ("OF-03")

(see, e.g., Fenton, Owen S., et al. "Bioinspired Alkenyl Amino Alcohol Ionizable Lipid Materials for Highly Potent In vivo mRNA Delivery." *Advanced materials* (2016)).

In some embodiments, one or more cationic lipids suitable for the present invention may be N-[1-(2,3-dioleyloxy) propyl]-N,N,N-trimethylammonium chloride or "DOTMA". (Feigner et al. (Proc. Nat'l Acad. Sci. 84, 7413 (1987); U.S. Pat. No. 4,897,355). Other suitable cationic lipids include, for example, 5-carboxyspermylglycinedioctadecylamide or "DOGS," 2,3-dioleyloxy-N-[2(sperminecarboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis, cis-9,12-octadecadienoxy)propane or "CLinDMA", 2-[5'-(cholest-5-en-3-beta-oxy)-3 '-oxapentoxy)-3-dimethy 1-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin--DMA", 2,2-dilinoleyl-4-dimethylaminoethyl[1,3]-dioxolane or "DLin-K-XTC2-DMA", and 2-(2,2-di((9Z,12Z)-octadeca-9,1 2-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, one or more cationic lipids may be chosen from XTC (2,2-Dilinoley 1-4-dimethylaminoethy 1-[1,3]-dioxolane), MC3 ((6Z,9Z,28Z,3 1Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7, 10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

B. Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), di stearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 30-50% (e.g., about 30-45%, about 30-40%, about 35-50%, about 35-45%, or about 35-40%) of the total lipids in a suitable lipid solution by weight or by molar.

C. Cholesterol-Based Lipids

In some embodiments, a suitable lipid solution includes one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

D. PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 5 kDa in length covalently attached to a lipid with alkyl chain(s) of C6-C20 length. In some embodiments, a PEG-modified or PEGylated lipid is PEGylated cholesterol or PEG-2K. In some embodiments, particularly useful exchangeable lipids are PEG-ceramides having shorter acyl chains (e.g., C14 or C18).

PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid(s) constitute(s) about 30-50% (e.g., about 30-45%, about 30-40%, about 35-50%, about 35-45%, or about 35-40%) of the total lipids in a suitable lipid solution by weight or by molar.

Exemplary combinations of cationic lipids, non-cationic lipids, cholesterol-based lipids, and PEG-modified lipids are described in the Examples section. For example, a suitable lipid solution may contain cKK-E12, DOPE, chol, and DMG-PEG2K; C12-200, DOPE, cholesterol, and DMG-PEG2K; HGT5000, DOPE, chol, and DMG-PEG2K; HGT5001, DOPE, chol, and DMG-PEG2K; cKK-E12, DPPC, chol, and DMG-PEG2K; C12-200, DPPC, cholesterol, and DMG-PEG2K; HGT5000, DPPC, chol, and DMG-PEG2K; or HGT5001, DPPC, chol, and DMG-PEG2K. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

V. Kits of the Disclosure

Any of the compositions described herein, or components thereof, may be comprised in a kit. In a non-limiting example, polynucleotides, cells or any reagents to manipulate or generate certain polynucleotides, proteins, peptides and/or cells may be comprised in a kit. Such a kit may or may not have one or more reagents for manipulation of molecules. Such reagents may include small molecules, proteins, nucleic acids, antibodies, buffers, primers, nucleotides, salts, and/or a combination thereof, for example. In particular embodiments, a polynucleotide that encodes a polypeptide that comprises a liver antigen-targeting entity and/or an immunostimulatory entity, or each component separately, or primers suitable for amplifying either entity, may be provided in a kit. In some cases, cells for harboring such a polynucleotide(s) may be provided in a kit, and/or an apparatus to obtain cells from an individual may be provided in the kit. The kit may have one or more reagents tailored to a particular one or more liver antigens and/or one or more immunostimulatory entities.

In particular aspects, the kit comprises the polynucleotide and/or polypeptide therapy of the disclosure and also another therapy. In some cases, the kit, in addition to the polynucleotide and/or polypeptide therapy embodiments and wherein the individual has cancer, also includes a second cancer therapy, such as chemotherapy, hormone therapy, and/or immunotherapy, for example. The kit(s) may be tailored to a particular cancer for an individual and comprise respective second cancer therapies for the individual.

The kits may comprise suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are presented in order to more fully illustrate the preferred embodiments of the disclosure. They should in no way, however, be construed as limiting the broad scope of the disclosure.

Example 1

Figure 2:
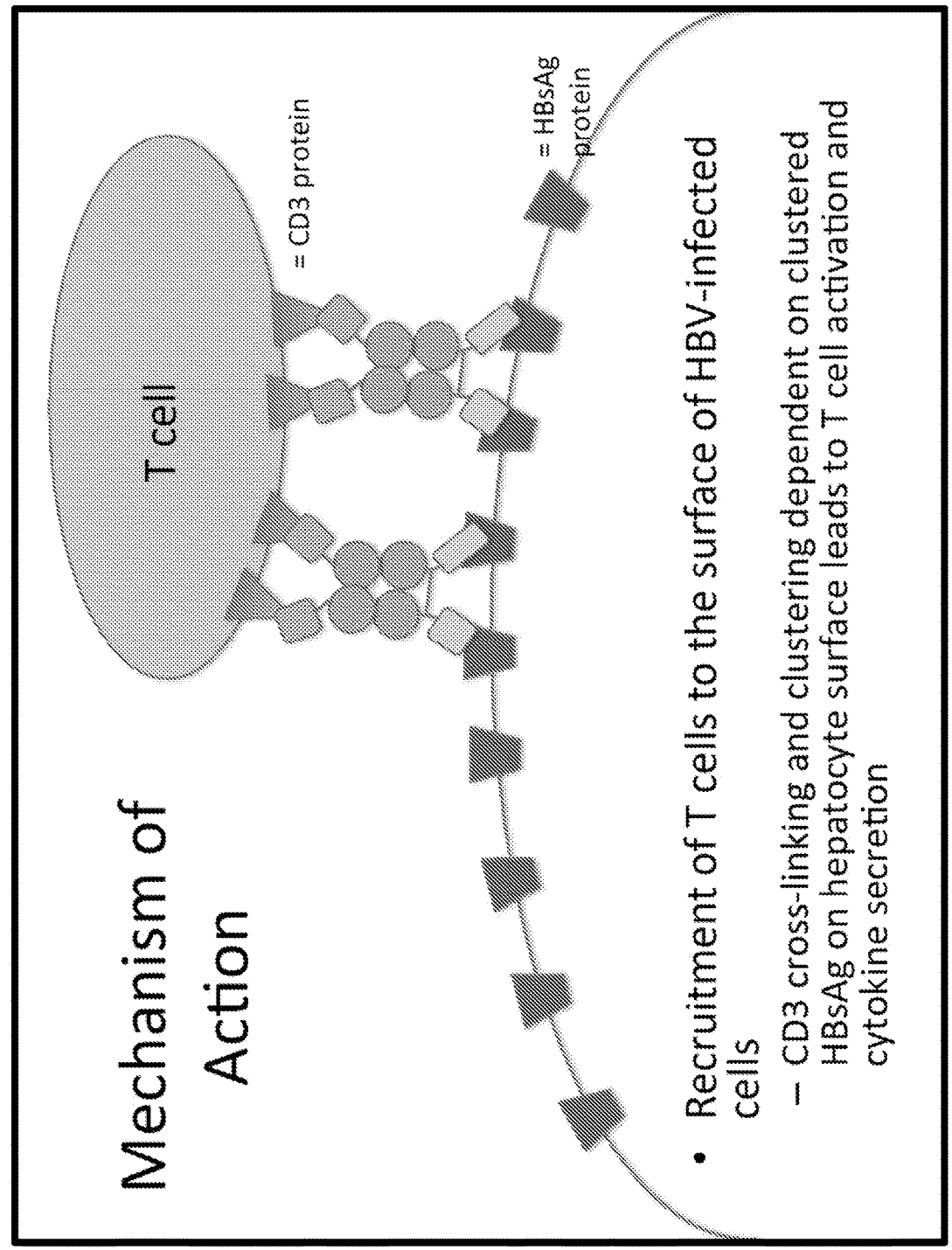
FIG. 2 illustrates an example of a mechanism of action for a particular bispecific antibody of the disclosure, without being bound by theory.
Figure 3:
FIG. 3 exemplifies a particular plasmid for use in a model for Hepatitis B infection.

A cartoon schematic of a single bispecific antibody design is illustrated in FIG. 1. In this example, the n-terminal end possesses an scFv XTL19 or 19 targeting HBsAg, the linker region is an Fc domain derived from human IgG1, and the c-terminal domain harbors an scFv against mouse CD3, in order to facilitate testing in mouse models. The recombinant protein would then be delivered for expression by gene therapy into the liver. An example of a mechanism for how such bispecific molecules function is shown in FIG. 2, wherein the molecules connect an antigen target (here HBsAg on cell surface) to T cells via CD3 binding (could be other cell types in other embodiments) leading to the clustering of CD3 molecules together resulting in T cell signaling and activation. In the testing system in mouse models, the inventors employed co-delivery of plasmid encoding target (HBV) plus luciferase reporter (see FIG. 3 for an example) and a plasmid encoding the bispecific antibody therapy under a CAG promoter are provided that simulates gene therapy into a human patient into the liver organ and limited expression in other tissues. The target antigen is only expressed in the liver along with the bispecific molecule, and luciferase mediated luminescence provides a convenient real-time readout for immune reaction inside the liver.

Figure 4:
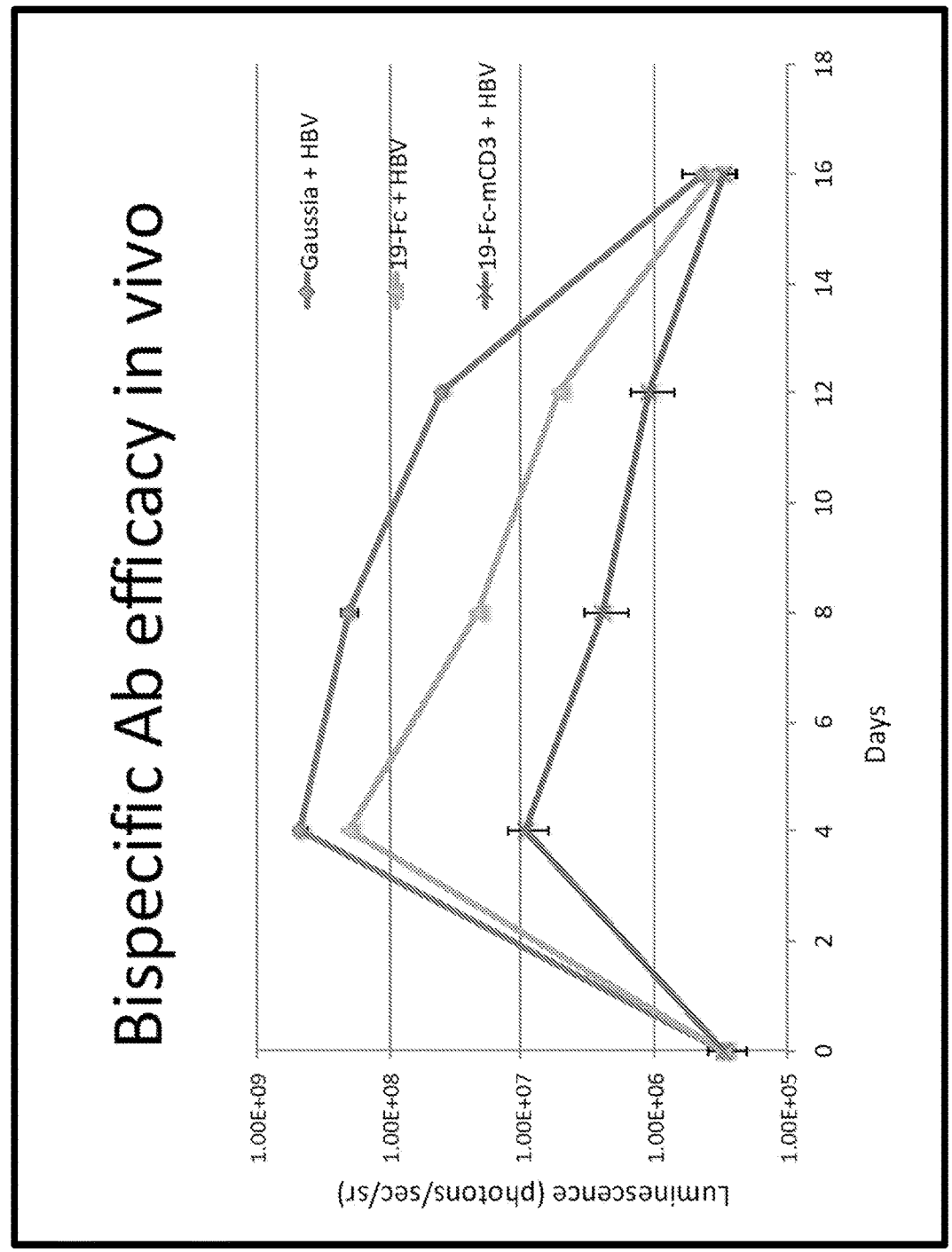
FIG. 4 demonstrates in vivo efficacy of one particular bispecific antibody encompassed by the disclosure.
Figure 5:
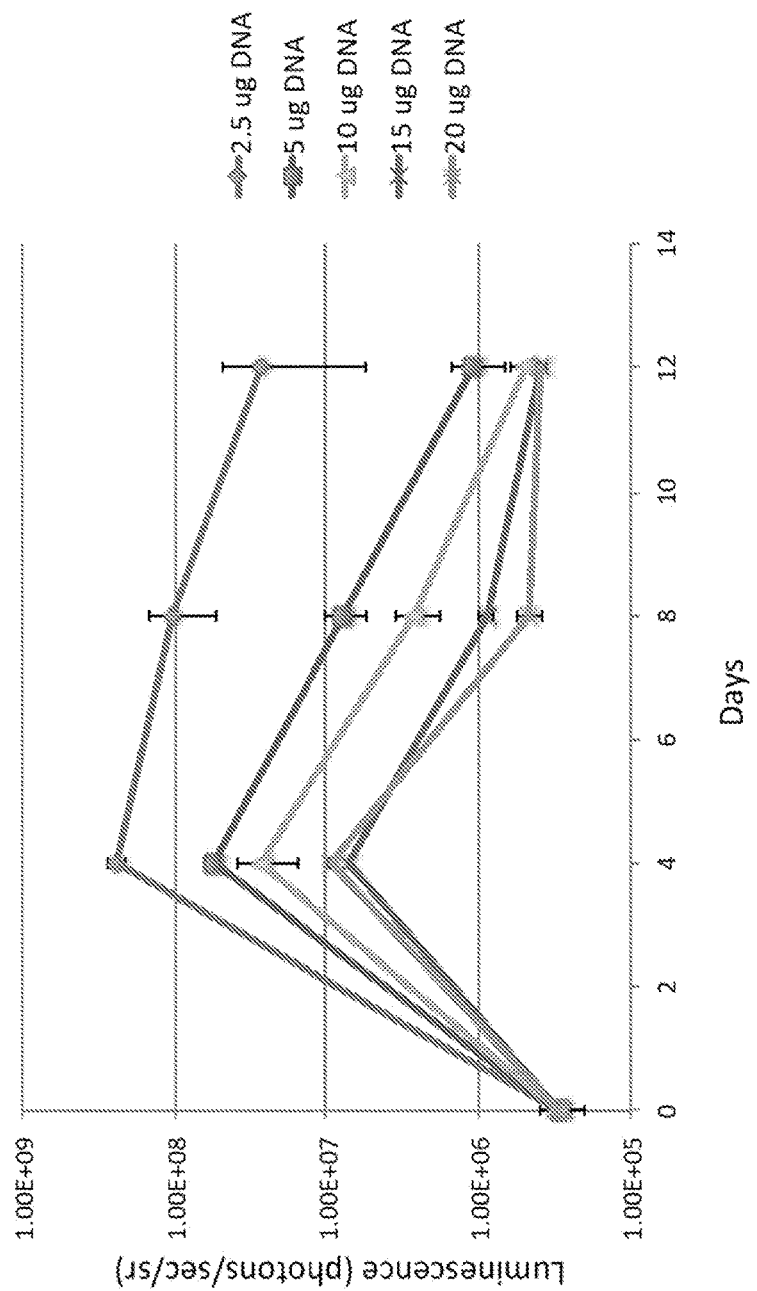
FIG. 5 shows examples of in vivo dosing for one particular bispecific antibody encompassed by the disclosure.

In an acute model of HBV infection, the artificial T cell response against HBV removed to roughly 100-fold the genome levels, compared to those of an early time point where no immune response against virus has started (day 4 and day 8) (FIG. 4). Improvement was also noted over the efficacy of antibody targeting antigen alone (19-Fc). This early setting simulates the human patient having no immune response to the virus at baseline. Current therapies do not target viral genomes, and genome decline (HBV covalently closed circular DNA) is marginal (2-fold) with RT inhibitors. There was observed a dose response to the efficacy of knockdown, indicating the centrality of T cell activation in the suppression and removal of HBV. More gene delivered to the liver resulted in a saturating dose at 15 µg and 20 µg levels (FIG. 5).

Figure 6:
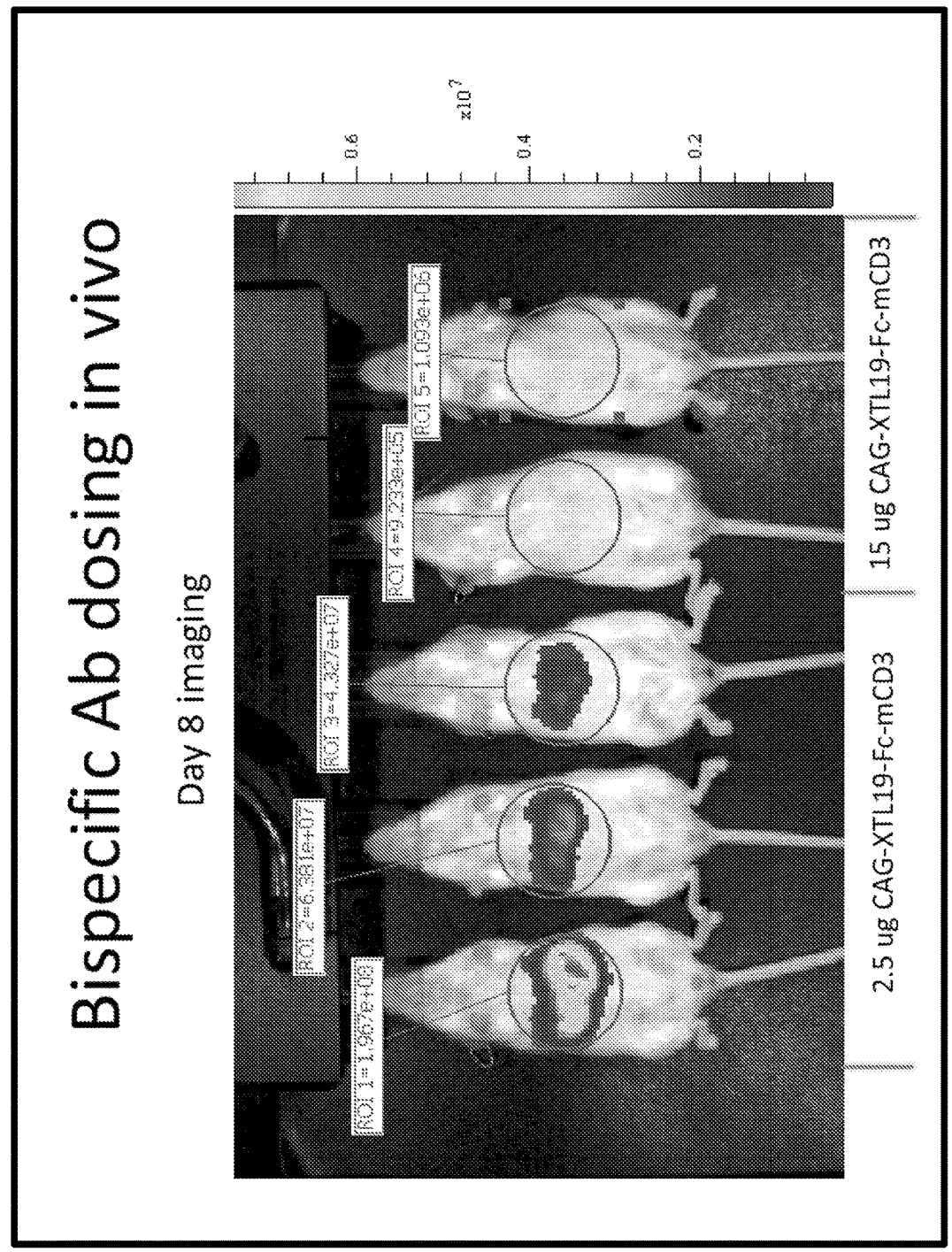
FIG. 6 demonstrates in vivo efficacy utilizing two examples of doses in a mouse model.

FIG. 6 demonstrates the visualization of the quantitative data. Similar experiments in tumor models are the gold standard for measuring responses. The drastic reduction in an immunocompetent animal model relying on recruitment of local T cells in the liver indicates that the approach is directly applicable to human therapy. Results represent complete viral clearance in a week, while current therapies in patients do not clear the viral genomes, but merely suppress serum markers.

Example 2

Hepatic Gene Therapy Expressing Bispecific Antibodies Redirects T Cells to Mediate Potent Antiviral Responses Against Hepatitis B Virus Novel therapies against hepatitis B virus (HBV) are needed to cure virus from patients, which cannot currently be achieved by drugs today. T cell responses clear HBV in acute infection, and adoptive transfer of antiviral T cells can lead to significant reductions in vivo. Seeking more scalable methods to harness T cells against HBV, the inventors developed a novel method of activating host T cells in situ in the liver for HBV therapy. Genes for bispecific antibodies binding to HBsAg and CD3 epsilon were delivered directly into the liver by hydrodynamic tail vein injection, where after they found murine T cells mediated multi-log reduction in HBsAg and reporter gene expression within 1 day. In situ expressed bispecific antibodies were prone to antigen-independent T cell activation in the liver microenvironment, affording resistance to potential viral mutation escape. This was a novel an unexpected finding, because traditionally bispecific antibodies do not activate immune cells in the absence of target antigen. In addition, in situ bispecific antibody production was not cytotoxic to hepatocytes, and the antiviral effect was largely noncytopathic. Finally, bispecific antibodies potently activated host anti-HBsAg antibody production after their expression, suggesting additional potential as an in situ vaccine. Overall, this strategy is useful for a clinical therapy for chronic HBV infection.

Introduction: Hepatitis B virus (HBV) currently chronically infects over 300 million people today. There is currently no cure for these individuals who are chronically infected. While current drugs can suppress serum HBV DNA levels, there is no effect on covalently closed circular DNA (cccDNA), the viral genome of HBV. In particular, the hepatitis B surface antigen (HBsAg) production is not curtailed, a key molecule that is thought to suppress the immune response, possibly through inhibiting plasmacytoid dendritic cells (Xu, et al., 2009) and innate immune signaling (Liu, et al., 2015). Newer proposed therapies degrade HBV RNA's using siRNA (Wooddell, et al., 2013) and antisense modalities (Billioud, et al., 2016), effectively knocking down HBsAg expression. However, HBV cccDNA remains untouched. It is hypothesized that HBV could be cured through re-activating the immune system to clear cccDNA by relieving the HBsAg-mediated suppression (Durantel & Zoulim, 2016), but this remains to be realized in human trials since preclinical animals models can't adequately test it.

More direct approaches of activating the immune system against HBV could prove to be an effective therapy toward cure. The CD8 T cell response is crucial toward clearing HBV in the liver (Thimme, et al., 2003). Furthermore, clearance is largely noncytopathic, relying primarily on secreted cytokines, INF-γ and TNF-α (Xia, et al., 2016). However, in HBV patients, the frequency of HBV-specific T cells is low (Boni, et al., 2007) and their functionality is impaired (Park, et al., 2016). Vaccine strategies depend on activating T cells that might not be present, and HBV knockdown strategies relying on a potentially dysfunctional immune system might prove to be fruitless.

T cells were previously redirected to attack HBV infected hepatocytes using chimeric antigen receptors (CAR) targeting HBsAg (Bohne, et al., 2008). While primarily secreted, there is a residual amount of HBsAg detected on the surface of infected hepatocytes that is recognizable by CAR-T cells. Redirected T cells were shown to reduce cccDNA from infected primary hepatocytes in vitro, and mediate transient viral reduction in an HBV transgenic mouse model (Krebs, et al., 2013).

While CAR-T cells represent a potential tool against HBV, the large number of HBV patients worldwide demand a more readily available off the shelf strategy. Toward this goal, the use of bispecific antibodies against HBV was investigated, which could give an adaptive immune response back to HBV through providing both humoral and cellular immunity. In particular, in an effort to directly activate host T cells toward given HBV-infected cells, bispecific antibodies can be constructed that targets both HBsAg on the surface of hepatocytes and CD3 epsilon (CD3) on the surface of T cells. Bispecific antibodies targeting CD3 were originally reported over 30 years ago (Staerz, et al., 1985; Staerz, et al., 1986) and have been seen in numerous applications since then, including most recently the FDA approved blinatumomab targeting the CD19 antigen (Przepiorka, et al., 2015). These molecules work by binding a target antigen on the cell surface, where after binding that antigen causes clustering of CD3 proteins on the T cell surface, triggering activation similar to the TCR complex. The advantage of this strategy is MHC independent T cell activation, facilitating the opportunity for general off the shelf strategies for all patients.

Current bispecific antibody approaches are challenged by complicated manufacturing process, complex pharmacokinetics requiring constant infusion, and potential toxicity issues through systemic T cell activation. All of these hurdles could be addressed through in situ expression of bispecific antibodies from DNA or RNA templates in patient tissues directly, but such attempts to express these genes directly in tissues have not been reported in the literature, but rather focused on secretion by cell vehicles (Compte, et al., 2013). Herein, there is a bispecific antibody against HBV, that when delivered to the liver tissue, mediates rapid reduction of the virus in an immunocompetent mouse model.

Examples of Results:

A gene therapy strategy was selected toward delivering the bispecific antibodies into the patient for multiple reasons: 1) soluble HBsAg in the serum will readily neutralize a majority of the infused therapeutic; 2) risk that T cells are systemically activated via cross-linking of CD3 induced by soluble surface antigen particles; 3) in clinical trials with HBV antibodies, it has been noted that a quick metabolism of antibodies takes place through the aforementioned endocytosis into the liver, such that decrease only last hours (Neumann, et al., 2010); 4) in clinical trials for bispecific T cell therapies, a continuous infusion of antibodies is often needed in order to measure a therapeutic effect (Ribera, et al., 2015), likely due to the logistics of the needed to simultaneously engage two different cells via a single molecule; and 5) reports of immune-complex disorders have occurred when anti-HBsAg antibodies have been infused into HBV patients (van Nunen, et al., 2001). Through a gene therapy strategy then, HBV immunity could be given to patients directly at the site of the liver and activate T cells in a specific and safe manner.

Given the novel focus on designing bispecific antibody therapies to be expressed in patient tissue, it was considered that optimizing artificial tissue culture conditions with varying amounts of T cells, producer cells, and target cells would not be informative for the in vivo context. The liver represents a complex microenvironment and architecture of different cells and components. T cells in circulation must reach through gaps in endothelial cells forming the space of Disse to even reach the hepatocyte membrane (Guidotti, et al., 2015), making it unclear if secreted molecules to effectively bridge these two targets. For all these reasons, direct tests in preclinical mouse model systems were selected.

It was desired to assess the treatment modality in a setting close to human infection and to use an immunocompetent mouse model, to allow for the recruitment of host T cells to HBV infected hepatocytes in vivo. This would include within their natural environment a more authentic ratio of T cells to hepatocytes that one might expect in the human patient, along with containing all the other important cell players such as Kupffer cells and natural killer cells, that could play additional roles in this therapy. Furthermore, one could follow subsequent adaptive immune responses in the mouse to the intervention.

In order to deliver both HBV and antibody genes into murine liver, hydrodynamic tail vein injection was employed (Liu, et al., 1999). The hydrodynamic model of HBV infection has previously been demonstrated to be convenient model of HBV via direct delivery of HBV plasmids, normally resulting in acute infection in most strains (Yang, et al., 2002; Chen, et al., 2012). Furthermore, this method can also be used to introduce therapeutics genes at into the liver (Viecelli, et al., 2014)' Alino, et al., 2003), which in this case will be co-injected bispecific antibody genes.

Antibody Production by Hepatocytes and HBV Luminescence Model Validation

Figure 7:
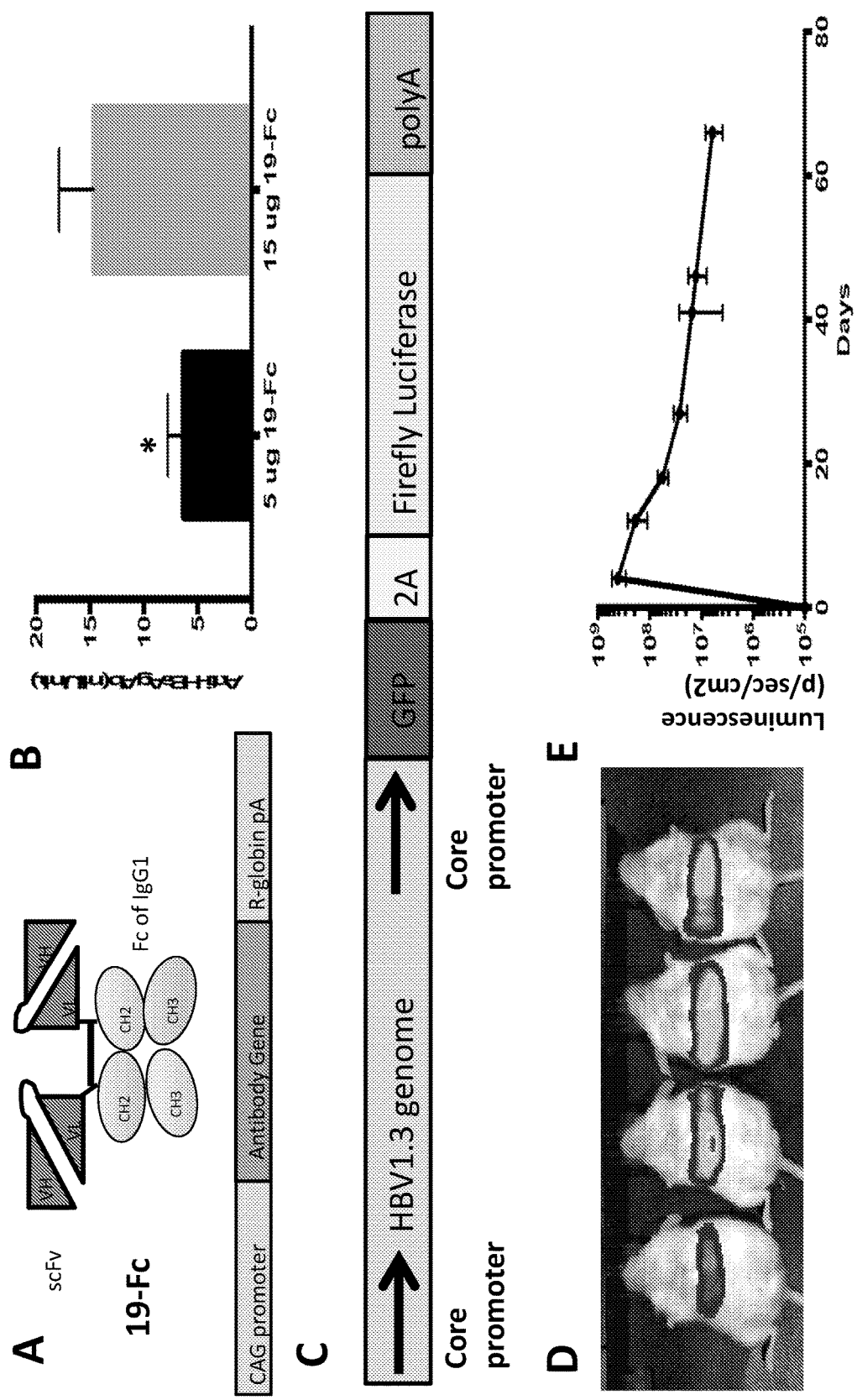
FIGS. 7A-7E. Antibody production was validated in vivo and a viral bioluminescence system for immune readout was established. (7A) The 19-Fc antibody was developed consisting of an scFv-Fc fusion protein derived from the 19.79.5 human antibody clone with specificity to the "a" determinant of HBsAg. The Fc domain was derived from the human IgG1 protein. Antibody was cloned into a pCAGGS vector for expression in vivo. (7B) Upon hydrodynamic injection, serum collected four days post injection and measured for functional 19-Fc protein that could bind HBsAg (n=4). (7C) A luminesce model was developed for HBV, combining delivering a wildtype HBV overlength genome with using the HBV core promoter to drive GFP and firefly luciferase expression. (7D) IVIS imaging revealed efficient and specific luminescence specific to the liver after injection of 5 ug of plasmid. (7E) Luminescence was monitored overtime in NSG mice, revealing a gradual decline in expression over 2.5 months (n=4, unpaired t-test, *=p<0.05)

It was desired first to establish the ability to delivery antibody proteins into the mouse liver for their expression in situ, resulting in their correct expression and secretion, while retaining their affinity for HBsAg. For these studies, the inventors chose to focus on a human antibody, mAb19.79.5 of XTL Pharma (known as XTL19 or 19 herein), previously validated in preclinical models (Eren, et al., 2000) and in clinical trials (Galun, et al., 2002) and effectively neutralizes HBV virions. The antibody targets a linear epitope on the "a" determinant of the small HBsAg with nanomolar affinity (Eren, et al., 1998). Hydrodynamic tail vein injection was carried out at 2 different doses (5 ug, 15 ug plasmid) of the hybrid antibody 19-Fc, consisting of the single chain variable fragment (scFv) of the XTL19 antibody clone appended to the Fc domain of the human IgG1 protein (FIG. 7A). Antibody expression was driven under the CMV early enhancer/chicken β actin (CAG) hybrid promoter that has been previously noted for high expression potency and resistance to silencing in the murine liver (Nguyen, et al., 2008), as opposed to CMV driven constructs (Kay, et al., 1992). The two different doses achieved serum anti-HBsAg antibody levels of 8 and 16 mIU/mL at day 4 post injection, with the 15 ug dose yielding antibody levels sufficient to protect a human patient from HBV infection (McMahon, et al., 2009) (FIG. 7B). It is likely that the effective antibody concentration within the liver microenvironment is much higher than the overall concentration in the serum, increasing potential potency.

With the ability to produce antibodies in hepatocytes verified, the inventors next sought to establish a system for monitoring therapeutic efficacy against virus in vivo in real-time, with a focus on the viral genomic stability given that targeting cccDNA is an important aspect for a sterilizing cure. Rather than focusing on serum markers, which may fluctuate but not inform on the levels of actual plasmid genome inside the cells, a bioluminescence system using firefly luciferase was used. A plasmid, HBV-Luc, was constructed harboring the HBV 1.3 overlength genome with the second HBV core promoter driving a fusion protein of GFP-2A-luciferase (FIG. 7C). The sequence of this construct is given in FIG. 13. Luciferase expression can be monitored in vivo as a readout of the immune response, as previously demonstrated in similar systems for HBV (Liang, et al., 2013) and malaria (Rai, et al., 2012). Furthermore, the HBV study found luminescence is a directly correlated to serum HBsAg and HBV DNA levels (Liang, et al., 2013). On a direct level, plasmid levels and HBV core promoter activity in the liver are tied to luminescence. The 5 ug HBV-Luc plasmid could successfully express luciferase after hydrodynamic injection (FIG. 7D), and could be expressed long-term in NOD SCID−/− γ−/− (NSG) mice in the absence of an adaptive immune response (FIG. 7E). This validates its use going forward in testing HBV therapeutic interventions.

In Vivo Screening for Bispecific Antibody Format Efficacy

There are multiple bispecific antibody formats with different geometries and valencies in the literature (Weidle, et al., 2012; Spiess, et al., 2015), and the inventors wanted to carry out a screening approach to ascertain the most potent protein in the context of hepatocyte-mediated production. Since the goal is to activate T cells in mice, an scFv was selected encoding the hamster 145-2C11 antibody clone binding to the mouse CD3 epsilon (mCD3) (Leo, et al., 1987), since engagement of this protein can activate murine T cells selectively. Furthermore, the scFv has been utilized in previous studies in order to construct bispecific antibodies to redirect murine T cells (Jost, et al., 1996). It was also tested whether adding costimulation with murine CD80 or B7.1 ectodomain could help engage CD28 receptors, as an alternative activation domain (Haile, et al., 2013). The inventors also tested one format with these activation moieties directly linked to the XTL19 scFv similar to the bispecific T cell engager (BiTE) format, along with a format including all of mCD3, mB7.1, and XTL19.

It is known that HBV antibodies have the ability to both neutralize infection and mediate faster clearance of particles, but to also enter the endosomes of hepatocytes and block the secretion of HBsAg particles (Schilin, et al., 2013). This function could help an inherent challenge in bispecific targeting, wherein the soluble HBsAg particles distract antibodies away from the target cell surface. For one approach, it was considered that engineering the normal IgG antibody format for T cell engagement could solve both of these challenges. By connecting an scFv against HBV via an the IgG Fc to another scFv directed against CD3 epsilon, one could both effectively neutralize HBV, block HBsAg, and recruit T cells to the surface of infected hepatocytes.

It was also considered whether or not to keep Fc receptor binding in these antibodies, which could add additional potency but also toxicities. The inventors desired to keep the function of neonatal Fc receptor (FcRn) binding, which is crucial for the inhibition of HBsAg secretion as demonstrated in previous studies (Schilling, et al., 2003). Towards safety, the other effector functions might cause potential toxicities. In a clinical trial, antibody-complex toxicities were noted in patients treated with anti-HBsAg antibodies (van Nunen, et al., 2001). Furthermore, in clinical trials with the bispecific catumaxomab and wildtype Fc domain, toxicity was noted during intravenous injection, via binding and cross-linking with FcR's causing systemic T cell activation (Mau-Sorensen, et al., 2015). In order to resolve this issue, it was decided to use IgG4 Fc domain with mutations in the linker region and in the CH2 domain that abrogate Fc receptor binding (Hudecek, et al., 2015). Another bispecific version had additional mutations to make the Fc domain monomeric in structure (Ying, et al., 2012). Furthermore, it was considered that some toxicity could be avoided with localized delivery of antibody to tissue site, and reduced CD3 affinity with scFv localization at c-terminus (Kuo, et al., 2012).

The inventors thus tested both IgG1 Fc domains that could bind to Fc receptors, and an IgG4 Fc domain with mutations to abrogate Fc receptor binding (Hudecek, et al., 2015). There was testing of appendage of the mCD3 scFv onto either the n-terminus or c-terminus of the Fc domain, with the XTL19 scFv occupying the other site. mB7.1 was added to the n-terminus in another format to provide costimulation signals to T-cells. A summary of the antibodies tested can be found in FIG. 8A. These various formats were systematically tested by co-injecting 15 ug Antibody with 5 ug HBV-Luc. As a control, 15 ug CMV-*Gaussia* was co-injected, being also a secreted protein but having no activating effect on the immune system. A positive control was also included of mCD3 antibody with inert Fc known to partially activate T cells (Smith, et al., 1997). At day 4, the peak of luciferase expression in the control group, luminescence levels were decreased. Of note, all antibody formats demonstrated efficacy against HBV, demonstrating the usefulness of the different permutations in antibody design and immunostimulatory domains that might be used in the current disclosure when delivered as a gene therapy into the liver. 19-Fc-mCD3 and mCD3-19 exhibited the lowest decreases in luminescence, and continued pursuing those in further studies (FIG. 8B).

Treating Acute HBV Infection with Bispecific Antibodies

The inventors focused first on the 19-Fc-mCD3 bispecific, because this format could leverage the additional Fc functionality and have more potential in therapeutic use, in at least certain aspects. This antibody was tested in an acute HBV model in immunocompetent mice, where hydrodynamic injection of HBV leads to viral clearance within weeks. The resolution is characterized by the development of anti-HBsAg antibodies and the infiltration of HBV-specific T cells into the liver (Yang, et al., 2002). It was considered that the bispecific will cause early reduction in HBV levels facilitating faster clearance in mice versus control groups. A dosing study was undertaken in vivo with bispecific antibodies comparing to the injection with HBV alone, to find out the highest dose response for therapy in this system. There was increasing inhibition of luciferase expression up to 15 ug CAG-19-Fc-mCD3, with 15 and 20 ug being relatively the same (FIG. 3A). Therefore, the 15 ug plasmid dose were used going forward.

Figure 9:
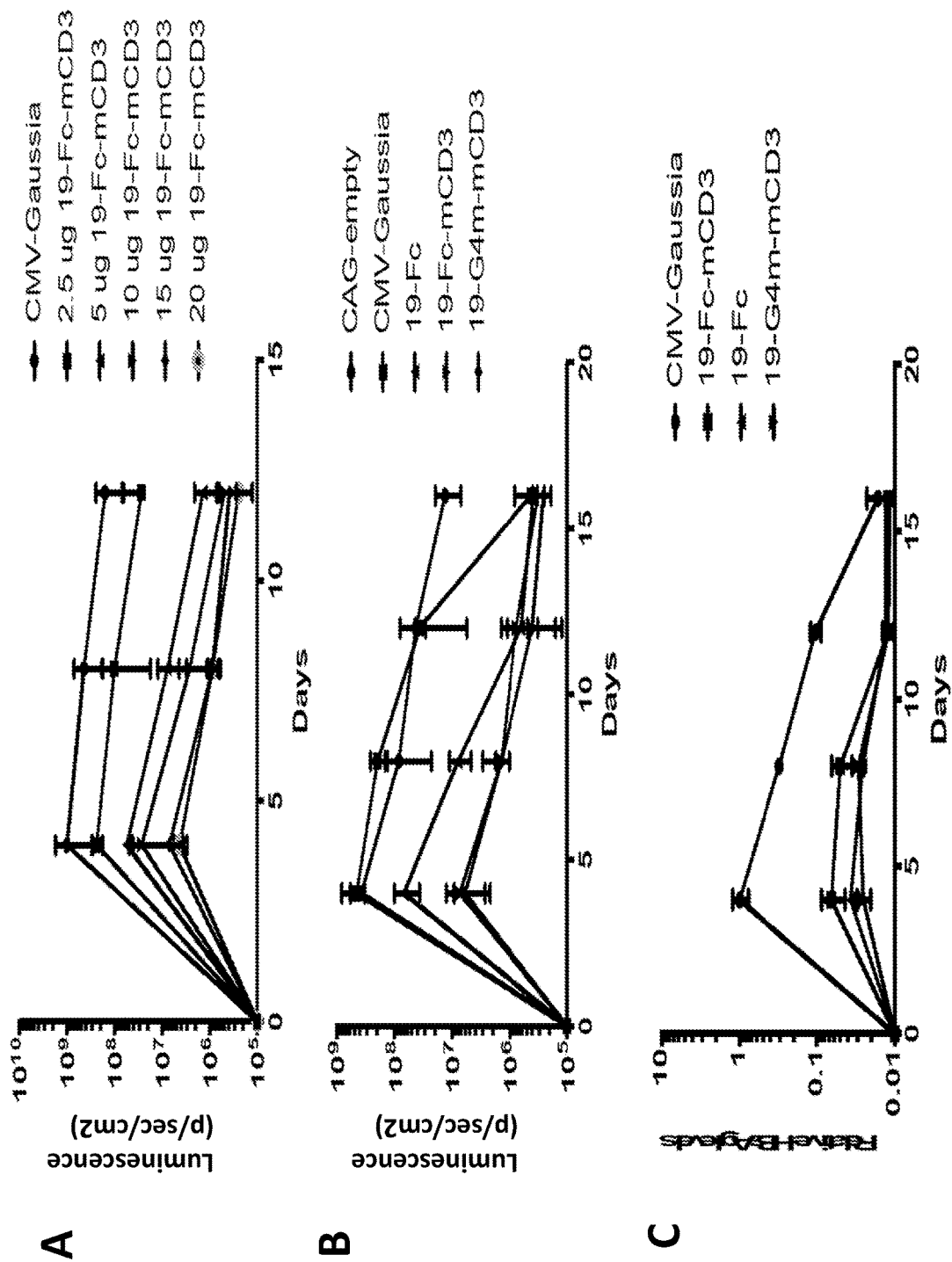
FIGS. 9A-9C. Bispecific antibodies reduce virus in an acute HBV mouse model. (9A) A dosing series was undertaken in order to find the plasmid level yielding the highest decrease in luminescence compared to *Gaussia* control at Day 4 post hydrodynamic injection with 5 ug HBV-Luc (n=4, unpaired t-test, *=p<0.05). (9B) Using the 15 ug dose, 19-Fc-mCD3 was compared to 19-Fc lacking mCD3 binding, as well as version containing G4m lacking Fc receptor binding. Co-injection of *Gaussia* and Empty pCAGGS served as controls (n=4, unpaired t-test, *=p<0.05). Background luminescence in the assay was $5 \times 10^5$ p/sec/cm². (9C) T the decrease in luminescence was correlated by monitoring serum HBsAg levels in the experiment, which normalized to the Day 4 HBsAg level of the HBV-Luc+ *Gaussia* condition (n=4, unpaired t-test, *=p<0.05)

The potency of 19-Fc-mCD3 and its mechanism of action was tested. There was a 1.79 log luminescence knockdown that occurred with 19-Fc-mCD3 targeted HBV at day 4 post injection (FIG. 9B). Notably, including the mCD3 scFv at the c-terminus resulted in significantly more luminescence decrease versus the 19-Fc antibody alone (0.82 log reduction, $p<0.05$). Furthermore, the Fc receptor function was not necessary for 19-Fc-mCD3 function as a 19-G4m-mCD3 version had similar potency. Final clearance may in part be driven by the presence of foreign protein, because *Gaussia* inclusion facilitated faster clearance versus including an empty plasmid construct at day 16. There was a 1.3-1.7 log decrease in HBsAg levels at day 4 with the 19-Fc and bispecific constructs, verifying similar trends in luminescence data with a virological marker (FIG. 9C).

Figure 10:
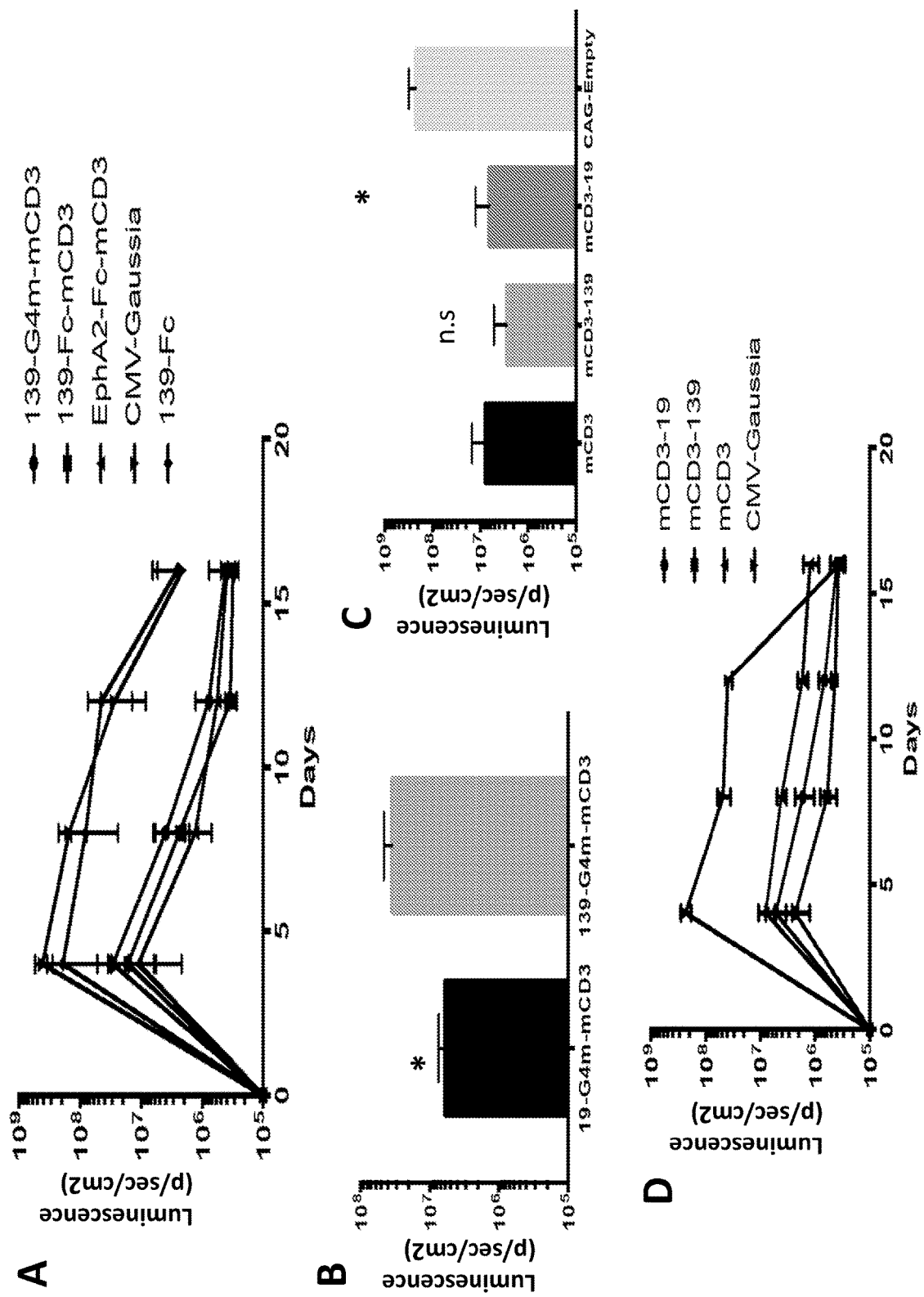
FIG. 10A-10D. Bispecific antibodies binding CD3 yield target antigen independent T cell activation. (10A) The XTL19 specificity was replaced with 139 scFv specificity to EGFRvIII and scFv against human EphA2, with similar groups to the previous test (15 ug Ab+5 ug HBV-Luc) (n=4, unpaired t-test, *=p<0.05). (10B) 19-G4m-mCD3 has significantly more luminescence reduction than 139-G4m-mCD3 at day 4 post injection, revealing a role for antigen targeting. (n=4, unpaired t-test). (10C) Bispecific antibodies were constructed to lack an Fc domain similar to the BiTE format, along with mCD3 scFv alone (n=4, unpaired t-test, *=p<0.05). (10D) The kinetics of treatment response for the BiTE formats was followed over 16 days.

Antigen Independent T Cell Activation by Bispecific Antibodies in Liver Microenvironment With efficacy validated using bispecific constructs containing scFv 19 and mCD3 binding, the specificity of the process was verified. A series of parallel antibodies were constructed with the XTL19 scFv domain replaced with the EGFRvIII-specific 139 scFv. This antibody targets an epitope expressed in certain cancers, but not in normal murine tissue (Morgan, et al., 2012). A version was constructed with an scFv targeting EphA2 as another control (Iwahori, et al., 2015). Repeating the same experiment, the mCD3 containing 139-Fc-mCD3, 13-G4m-mCD3, EphA2-Fc-mCD3 could all decrease luciferase levels, indicative of T cell activation (all $p<0.05$ vs CMV-*Gaussia* control) (FIG. 10A). By comparison, the 139-Fc had no activity in decreasing luminescence versus control, as expected ($p=0.87$). Similar antigen independent background activation had been previously reported with this same bispecific design, albeit significantly less than the on target activation (Kuo, et al., 2012). The inventors also sought to compare two similar versions side by side with G4m domain linker, in order to remove the confounding role of Fc receptors in facilitating antibody-T cell cross-linking. Looking at luminescence levels at Day 4, the 19-G4m-mCD3 construct decreased luminescence significantly more than the 139-G4m-mCD3, suggesting that the 19 scFv might help trigger increased bispecific antibody clustering and T cell activation in an antigen-dependent manner, as would be anticipated (FIG. 10B).

Because the Fc-containing antibodies inherently are dimeric, the two mCD3 binding portions alone might help facilitate some level of T cell activation. It was considered whether monomeric bispecific molecules would have decreased or no antigen-independent T cell activation. A series of bispecific antibodies were constructed similar to the BiTE format found in blinatumomab, which does not activate T cells in the absence of target antigen (Brischwein, et al., 2007). The inventors appended the mCD3 binding portion to the n-terminus of the BiTE since that has been reported to provide better efficacy in mouse models (Schlereth, et al., 2006). An scFv alone construct was also designed that would bind mCD3 and lack any other binding component. Unexpectedly, the mCD3-139 and mCD3 alone vectors also stimulated T cell activation and luminescence decrease to similar levels as mCD3-19 ($p<0.05$ vs CAG-empty) (FIG. 10C). This suggests that the liver might readily produce aggregates of antibody proteins in over-expression conditions that could cause CD3 clustering, a common phenomenon during the industrial recombinant protein production resolved in downstream processing (Paul, et al., 2014), but cannot otherwise be removed in this setting. Antigen-independent activation by bispecific antibodies secreted from cell lines in vitro has previously been reported with this study similar to that phenomenon (Compte, et al., 2014). The time course of BiTE dependent activation was similar to the Fc containing constructs previously studied, indicating no additional benefit in decreasing luminescence (FIG. 10D).

Mechanism of Action for Bispecific Antibodies in Clearing HBV

Figure 11:
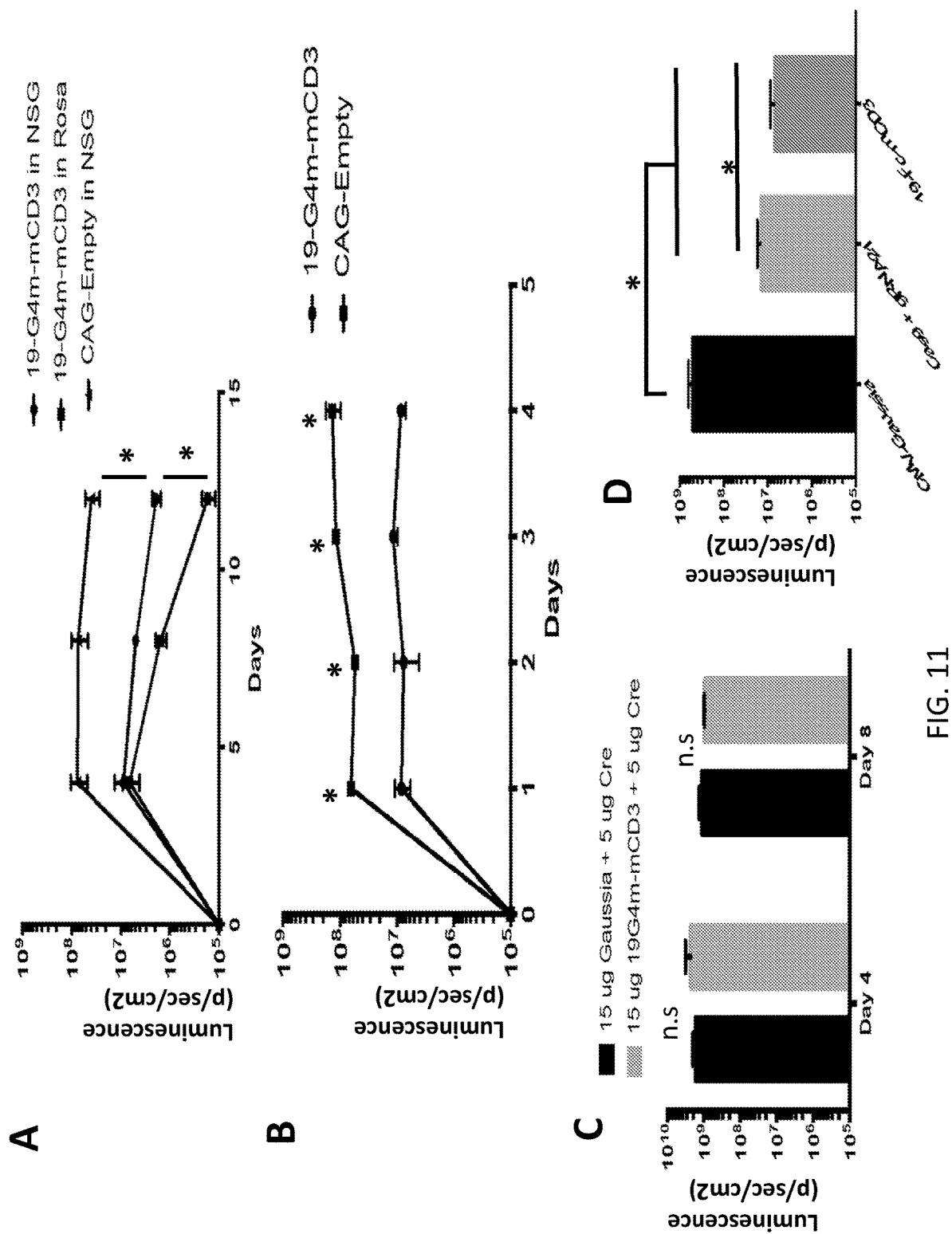
FIGS. 11A-11D. Expression length, safety, and clearance mechanism was evaluated for bispecific antibody therapy. (11A) Contribution of adaptive immunity in the context of bispecific antibody therapy was assessed by comparing 19-G4m-mCD3 therapy in NSG versus immunocompetent mice, showing reduction stopped in NSG mice after initial bispecific mediated reduction. (11B) The time course of initial bispecific antibody activation was followed over the first 4 days, with significant decrease in luminescence occurring at Day 1, and not increasing thereafter (unpaired t-test). (11C) Toxicity of bispecific antibody expression was assessed co-injected Cre plasmid with 19-G4m-mCD3 versus *Gaussia* into Rosa-Luc mice. Differences in luminescence were not significant, indicating hepatocyte survival (n=4, unpaired t-test, *=p<0.05). (11D) CRISPR-Cas9 therapy was compared against 19-Fc-mCD3 in the same system, with similar significant reductions in luminescence, albeit with different mechanisms of action (n=4, unpaired t-test, *=p<0.05)

The mechanism of action of the bispecific antibodies was further considered. So far, antibody expression was driven with a CAG promoter, which after introduction could in certain embodiments lead to continuous production of antibody until all HBV is eliminated. On the other hand, the previous figures suggest that the effect might be only peak at day 4, with the final elimination happening by plasmid inactivation or host immune response. To clarify, an experiment comparing bispecific activity in NSG and WT mice was performed. Bispecific antibodies in NSG mice should be able to activate residual immature T cell progenitors (Falk, et al., 1996), and indeed the day 4 point between NSG and WT mice was similar (FIG. 11A). After, however, the NSG mouse saw continued persistence of luminescence signal, while the WT mouse completely cleared, indicating that antibody is not continuously made through the experiment and that host adaptive immunity is key for the later stages of elimination on the curve. With the finding that bispecific antibody action happens early, the inventors wanted to find out how early. Similar experiments as FIG. 9 were repeated, except the luminescence signal was measured every day for the first 4 days. A 1.03 log difference between control and antibody treated already occurs at day 1 post injection (FIG. 11B), with the similar difference largely maintained subsequently. This suggests the first secreted bispecific molecules must activate T cells on day 1, producing cytokines that ultimately help silence the plasmid CAG-antibody expression vector, in addition to helping clear HBV.

It was desired to check if the expression of the antibodies themselves by hepatocytes was toxic, which otherwise might produce the therapeutic effects observed so far. The same experiments were repeated, but replaced the HBV-Luc vector with a CMV-NLS-Cre plasmid. Plasmids were co-injected into a ROSA-LoxP-STOP-LoxP Luciferase (Rosa-Luc) mouse strain, activate luciferase expression in the liver. The luminescence levels were not significantly different between bispecific antibody injected and *Gaussia* injected mice at day 4 or day 8 (FIG. 11C), suggesting that the bispecific antibody production is not toxic to hepatocytes, whose death would have reduced signal.

The CRISPR-Cas9 system has the ability to specifically target and cut DNA sequences of choice, and has been proposed as a therapy to target the HBV DNA genome in numerous studies (Dong, et al., 2015; Seeger & Sohn, et al., 2014; Karimova, et al., 2015). On the other hand, it has been reported recently that the mammalian immune systems have their own ability to up-regulate endogenous effects to degrade HBV cccDNA (Lucifora, et al., 2014). It was desired to compare the two approaches with different mechanisms of action head to head in the same system, in order to assess their merits. The inventors co-injected Cas9 with gRNA-21, previously found to be highly potent (Ramanan, et al., 2015), with HBV-Luc. CRISPR and the bispecific antibodies had similar knockdown at Day 4 (FIG. 11D), suggesting that inducing inflammation alone would be an alternative to designer nuclease strategies.

Bispecific Antibody Treatment of a cccDNA Mouse Model In Vivo

Figure 12:
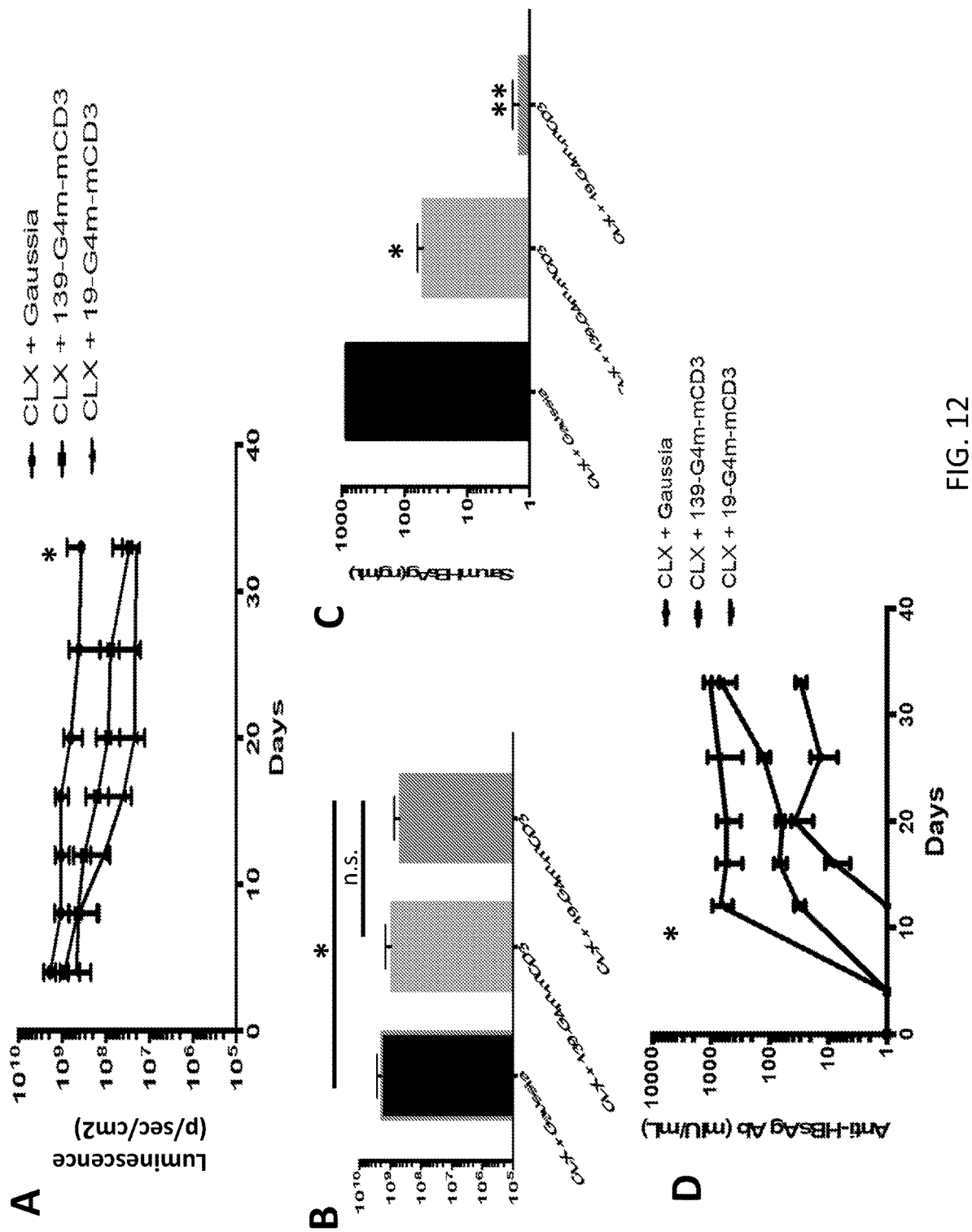
FIGS. 12A-12D. Bispecific antibodies can promotes HBV cccDNA clearance and host immune response in a novel mouse model of HBV. (12A) A Cre/LoxP-HBV (CLX) plasmid was used to generate cccDNA in vivo, while also marking infected hepatocytes with luciferase expression in Rosa-Luc mice. 5 ug CLX plasmid was co-injected with 15 ug 19- or 139-G4m-mCD3 plasmid or 15 ug CMV-*Gaussia*, and luminescence levels monitored. Infected hepatocytes appeared to be cleared in the bispecific treated groups, as judged by drops in luminescence. (12B) The Day 4 luminescence levels among the different groups was compared to assess any initial cytotoxicity against infected cells. (n=4, unpaired t-test, *=p<0.05). (12C) HBsAg serum levels were also assessed at Day 4 post injection, with the bispecific constructs yielding over 1.5 log reduction in serum HBsAg. (n=4, unpaired t-test, *=p<0.05, =p<0.001) (12D**) The ability of bispecific antibodies to trigger adaptive immunity was tracked measuring the serum levels of anti-HBsAg antibodies, with differences starting at day 12 (n=4, unpaired t-test, *=p<0.05)
Figure 14:
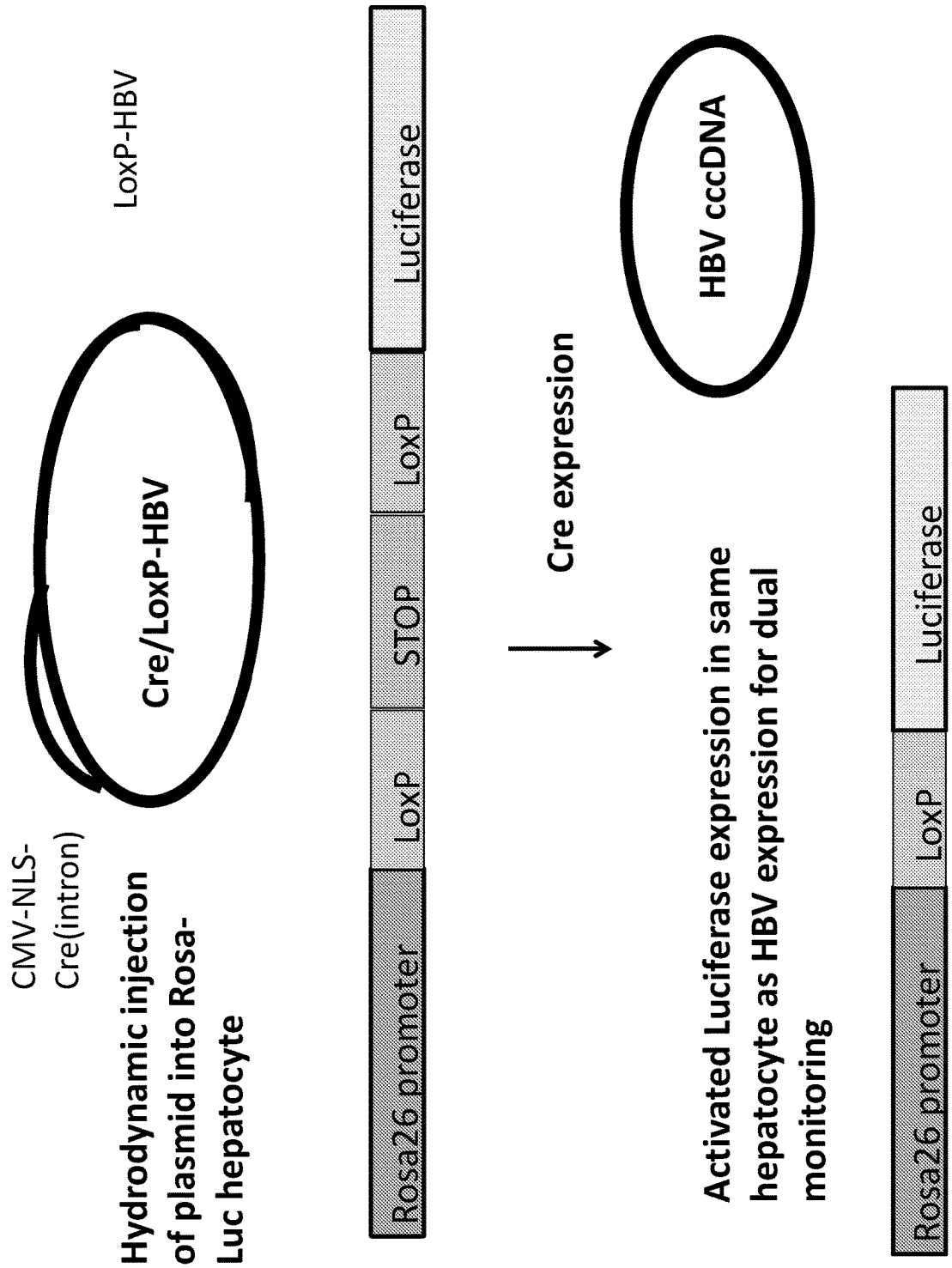
FIG. 14. Dual monitoring system for infected hepatocytes using bioluminescence and cccDNA generation. Cre/LoxP-HBV plasmid contains a CMV-NLS-Cre(intron) cassette and a LoxP-HBV flanked genome, with the LoxP inserted between amino acid 83 and 84 of the HBV X protein. Plasmid was hydrodynamically injected into Rosa-Luc mice, which contain driven by the Rosa26 promoter a LoxP-STOP-LoxP-firefly luciferase cassette. Upon introduction, CMV driven Cre recombinase expression will both excise and form a recombinant cccDNA molecule, and activate luciferase expression in the same cell. Thus, every cell that has HBV cccDNA will also have luciferase expression, affording dual monitoring and readouts.

The ability of bispecific antibody therapy to induce cccDNA clearance in vivo, representing a more authentic model for the human infection, was investigated. To this purpose, the inventors utilized a tool comprising a flox'd HBV genome with a NLS-Cre (containing an internal intron) cassette driven by CMV promoter in cis on the same plasmid (FIG. 14). When this plasmid is introduced into Rosa-Luc mice, the Cre recombinase activates luciferase expression in the host cell chromosomes and episomal cccDNA formation (FIG. 14). If HBV kills infected cells, then the luciferase signal should completely disappear with therapy. If on the other hand, the bispecific antibody activates T cells to remove cccDNA from mouse hepatocytes non-cytopathically, the luciferase signal should remain at high levels, while HBV cccDNA is cleared from the mouse. The inventors co-injected 15 ug of 19-G4m-mCD3, control 139-G4m-mCD3, or Gaussia along with 5 ug Cre/LoxP-HBV (CLX) plasmid. Over time the two treated groups showed a loss in luminescence over time, but that high levels of luminescence remained, indicating the original infected cells were not entirely eliminated (FIG. 12A). Notably, the Gaussia treated group showed a much slower decline over the same time course, suggesting some tolerance to HBV antigens. Because it was established that the first days are when bispecific antibodies primarily function, in at least some embodiments, it was desired to assess the cytotoxicity at the first time point. The 19-G4m-mCD3 group had 75% less luminescence than the Gaussia control, which was statistically significant (FIG. 12B). At the same time point, the 19-G4m-mCD3 group already had a 1.65 log drop in HBsAg levels, indicating that noncytopathic effects predominated, with cytotoxicity driven by 19-G4m-mCD3 playing a minor role (FIG. 12C). While bispecific antibodies appear to only act briefly post injection, it was desired to see their potential to modulate the adaptive immune response and act as an in situ vaccine. The development of anti-HBsAg antibodies in mice was measured, and the 19-G4m-mCD3 group developed high titer antibodies at much faster and higher levels as compared to the 139-G4m-mCD3, which lacked antigen binding, and the Gaussia group, which developed almost no antibodies during this period to HBsAg (FIG. 12D). This result suggests that that combination of antigen recognition and T cell activation, humoral and cell mediated arms, has significant advantages over activation of T cells (139-G4m-mCD3 group) alone.

Figure 15:
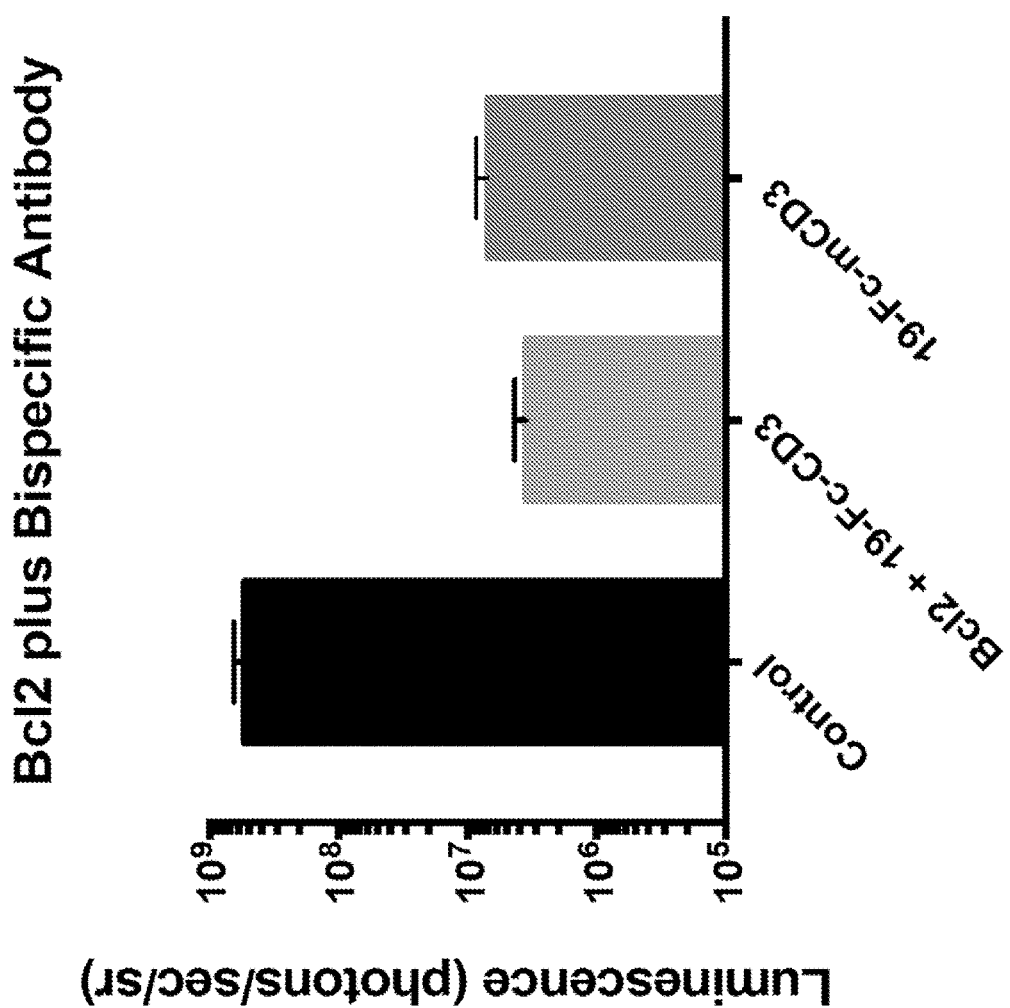
FIG. 15. Testing if therapeutic efficacy of delivering immune stimulating molecules against HBV would be maintained when cells also expressed an apoptotic inhibitor to prevent cell death. Mice (n=4+ were all hydrodynamically injected with 5 ug HBV-Luc plasmid, along with 5 ug CAG-Bcl2 or Control plasmid, plus 15 ug 19-Fc-mCD3 plasmid. Expressing an anti-apoptotic protein inside cells does not inhibit bispecific antibody efficacy as judged by equivalent bioluminescence decrease to control condition.

Given the importance of maintaining hepatocyte integrity and health during therapy, it was considered if one could co-deliver additional proteins or molecules that could help protect hepatocytes from destruction in addition to the therapy. Bcl2 was previously shown to prevent Fas antibody induced fulminant hepatic failure in mice (Lacronique, et al. 1996). The concurrent question was if this might interrupt the ability of the bispecific antibody to mediate HBV suppression. Mice (n=4+ were all hydrodynamically injected with 5 ug HBV-Luc plasmid, along with 5 ug CAG-Bcl2 or Control plasmid, plus 15 ug 19-Fc-mCD3 plasmid. Expressing an anti-apoptotic protein, Bcl2, inside cells does not inhibit bispecific antibody efficacy as judged by equivalent luminesce decrease to control condition, confirming non-cytopathic efficacy of antibody action, along with a novel potential safety feature to further prevent hepatocyte death (FIG. 15).

Example 3

In-Situ Liver Expression of HBsAg/CD3-Bispecific Antibodies for HBV Immunotherapy Hepatitis B virus (HBV) is a partially double stranded DNA virus with tropism to the liver, infecting over 300 million people chronically worldwide, causing cirrhosis and liver cancer in a significant number of these patients (El-Serag, et al., 2012). Once infected, very few HBV patients develop antibodies against and clear hepatitis B surface antigen (HBsAg), which serves a clinical biomarker for functional cure (Liu, et al., 2010). There is no effective treatment for chronic HBV patients; a five year treatment course with entecavir, a reverse transcriptase inhibitor, results in HBsAg seroconversion in only 1.4% of patients (Chang, et al., 2010). These antiviral inhibitors suppress serum HBV DNA levels, but have no effect on covalently closed circular DNA (cccDNA), the episomal transcriptional template of HBV. This molecule is very stable once formed in the hepatocyte, and cccDNA has been shown to persist for years (Werle-Lapostolle, et al., 2004). Pegylated interferon (IFN)-α is also approved for HBV therapy, but has shown efficacy only in a minority of patients, while also being not well tolerated (Perrillo, et al., 2009).

In patients who clear HBV during the acute infection, the CD8-positive T-cell response is crucial (Thimme, et al., 2003). This immune response is, in part, noncytopathic, relying primarily on secreted cytokines, IFN-γ and tumor necrosis factor (TNF)-α, to mediate cccDNA degradation (Xia, et al., 2016). However, the frequency of HBV-specific T cells is low in chronically infected HBV patients (Boni, et al., 2007), and their functionality is impaired (Park, et al., 2016). Given the paucity of antiviral T cells in the host, T cells have been redirected to attack HBV-infected hepatocytes using chimeric antigen receptors (CAR) specific for HBsAg (Bohne, et al., 2008). Redirected T cells were shown to reduce cccDNA from infected primary hepatocytes in vitro (Bohne, et al., 2008), and mediate transient viral reduction in an HBV transgenic mouse model (Krebs, et al., 2013). While CAR-T cells represent a potential therapy against HBV, T-cell products currently have to be produced for each patient individually, limiting their potential utility as a readily available therapeutic. To develop an "off-the-shelf product" to redirect T cells to HBsAg-positive hepatocytes, the inventors investigated here the use of bispecific antibodies that recognize HBsAg and CD3, which is expressed on almost all T cells.

Bispecific antibodies (Abs) targeting CD3 to direct T cells to cell surface antigens were originally reported over 30 years ago (Staerz, et al., 1985; Staerz, et al., 1986)), and have shown promising antitumor activity in numerous preclinical models. However, only blinatumomab, a bispecific Ab that targets CD3 and CD19, expressed on B-cell malignancies, has received FDA approval so far (Przepiorka, et al., 2015). Current bispecific Ab approaches are challenged by a complicated manufacturing process, short half lives requiring continuous infusions, and side effects secondary to systemic T-cell activation (Mau-Sorensen, et al., 2015). These hurdles could be overcome through in situ expression of bispecific Abs from DNA or RNA templates in patient tissues, but there have been few reports on such strategies (Compte, et al., 2013; Pang, et al., 2017; Stadler, et al., 2017). The liver absorbs major fractions of gene therapy vectors, nanoparticles or liposomes allowing gene constructs to be delivered more readily than in any other organ. Expression of bispecific Abs in the liver should have several advantages compared to the passive infusion of recombinant proteins for treating HBV. Local expression should result in increased Ab concentrations in the liver, before being diluted in the circulation. Moreover, soluble HBsAg in the serum of HBV patients can reduce efficacy by neutralizing a substantial fraction of infused Abs (Galun, et al., 2002), and the formed HBsAg/Ab immune complexes carry the risk of immune-complex disorders in HBV patients (van Nunen, et al., 2001).

To overcome these limitations, the inventors have developed an approach to express in situ a bispecific Ab to redirect T cells to HBsAg. The results in transfection-based murine models of HBV indicate a rapid reduction of the virus in a predominately noncytopathic manner.

Examples of Results

Figure 16:
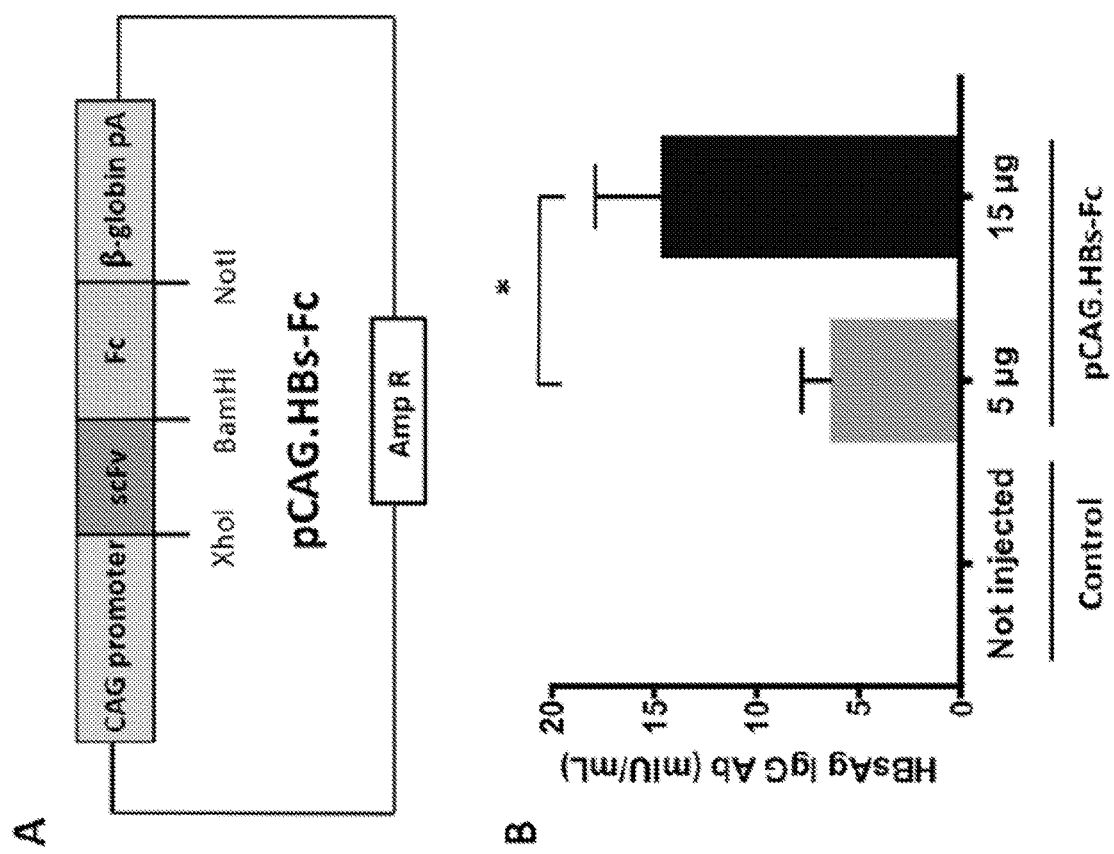
FIGS. 16A-16B. Brodynamic tail vein injection of pCAG.HBs-Fc results in HBs-Fc antibody expression in vivo. (16A). Scheme of pCAG.HBs-Fc. (16B). Serum was collected 4 days post hydrodynamic tail vein injection of pCAG.HBs-Fc. The serum concentration of HBs-Fc was determined by HBsAg IgG Ab ELISA (n=4, * p<0.05)

Hydrodynamic tail vein injection of a plasmid expressing HBsAg-specific antibodies results in the production of functional antibody in vivo. To evaluate the feasibility of expressing functional HBsAg-specific Ab in vivo, a mini-gene was cloned encoding a HBsAg-specific Ab (HBs-Fc), consisting of the immunoglobulin heavy-chain leader peptide, a single chain variable fragment (scFv) derived from the HBsAg-specific Ab 19.79.5 (Galun, et al., 2002; Eren, et al., 1998; Eren, et al., 2000), and the Fc domain of human IgG1, into the expression plasmid pCAG (pCAG.HBs-Fc; FIG. 16A). Hydrodynamic tail vein (HTV) injection was employed to deliver plasmids into the liver, wherein a large volume bolus (10% fluid-body volume) is injected with plasmid DNA (Liu, et al., 1999), resulting in specific delivery into hepatocytes by punching holes into cell membranes (Zhang, et al., 2004). Five or 15 µg of pCAG.HBs-Fc was injected via HTV injection into immune competent mice, and the plasma concentration of HBs-Fc was measured 4 days post injection by ELISA. Mean HBs-Fc concentrations were 6.4 mIU/mL for 5 µg and 14.7 mIU/mL for 15 µg injected plasmid (FIG. 16B). Thus, HTV injection of pCAG.HBs-Fc results in significant, dose-dependent production of HBsAg-specific Abs in vivo.

Figure 17:
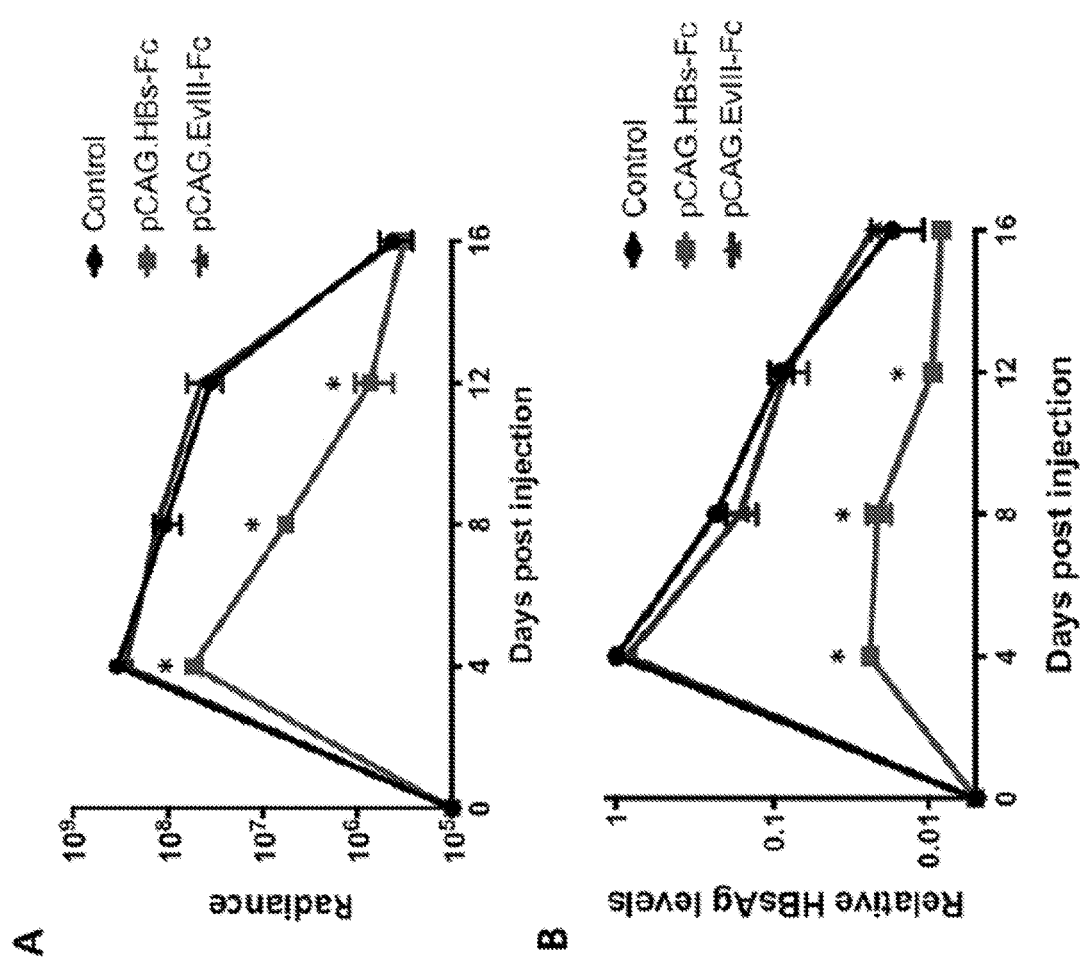
FIGS. 17A-17B. HBs-Fc gene delivery into hepatocytes has anti-HBV in vivo. (17A) Immunocompetent mice were co-injected by hydrodynamic tail vein injection with 5 μg pHBVffLuc and 15 μg pCAG.HBs-Fc, pCAG.EvIII-Fc, or control plasmid. Quantitative bioluminescence imaging data (radiance±photons/sec/cm2/sr) for all mice are shown (mean±s.e.m, n=3, * p<0.05). (17B) HBsAg levels were determined by ELISA. Data was normalized to the day 4 HBsAg level of the pHBV-ffLuc/control plasmid group (mean±s.e.m., n=3, * p<0.05)
Figure 21:
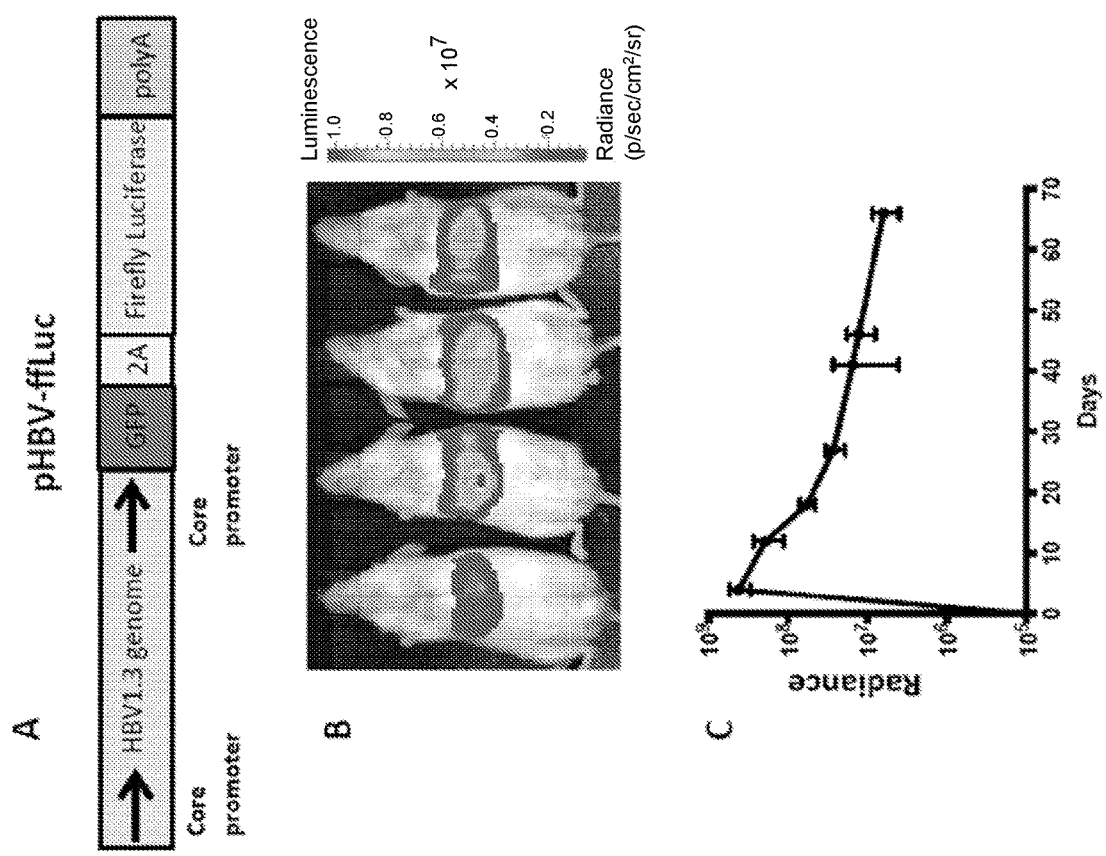
FIGS. 21A-21C. Murine model that allows for measuring the clearance of HBV using non-invasive bioluminescence imaging. (21A) Scheme of plasmid encoding the overlength (1.3-mer) HBV genome and a core protein fused GFP-2A-ffLuc cassette, both under the transcriptional control of identical HBV core promoters. (21B, 21C) NSG mice were injected with 5 µg of pHBV-ffLuc by hydrodynamic tail vein injection, and ffLuc expression was monitored by bioluminescence imaging. (21B) Bioluminescence images of mice on day 4 post injection. (21C) Quantitative bioluminescence imaging data (radiance=photons/sec/cm2/sr) is shown over time (mean and standard error mean, n=4)

HBs-Fc gene delivery has antiviral activity in vivo. To evaluate if in vivo expression of HBs-Fc has antiviral activity a murine model was adapted that allows for measuring the clearance of HBV using non-invasive bioluminescence imaging, which correlated with serum HBsAg and HBV DNA levels (Liang, et al., 2013). Bioluminescence of a reporter gene had previously been shown to be a sensitive readout for CD8 T cell responses in the liver against a co-delivered antigen gene (Stabenow, et al., 2010; Rai, et al., 2012). Briefly, a plasmid was generated encoding the HBV genome and a green fluorescent protein (GFP)-2A-firefly luciferase (GFP-2A-ffLuc) expression cassette, both under the transcriptional control of identical HBV core promoters (pHBV-ffLuc; FIG. 21A). HTV injection of pHBV-ffLuc into NSG mice resulted in luciferase expression in the liver as judged by bioluminescence imaging, confirming the functionality of pHBV-ffLuc (FIGS. 21B, 21C). The introduction of HBV plasmid DNA by HTV injection into immunocompetent mice results in immune clearance over two weeks, in a process resembling acute HBV infection (Yang, et al., 2002). To evaluate if expression of HBs-Fc induces clearance of HBV, pHBV-ffLuc was co-injected with pCAG.HBs-Fc, a pCAG plasmid encoding an Ab specific for an irrelevant antigen (Morgan, et al., 2012) (EGFRvIII; pCAG.EvIII-Fc), or a control plasmid. Keeping the total amount of DNA injected consistent, co-injection of 5 µg pHBV-ffLuc with 15 µg pCAG.HBs-Fc resulted in a significantly lower luciferase signal in comparison to co-injection with 15 µg pCAG.EvIII-Fc or control plasmid (FIG. 17A). In addition, pHBV-ffLuc/pCAG.HBs-Fc co-injected mice had significantly lower levels of serum HBsAg levels (FIG. 17B) in comparison to the other treatment groups, indicating that HBs-Fc has antiviral activity in vivo.

Figure 18:
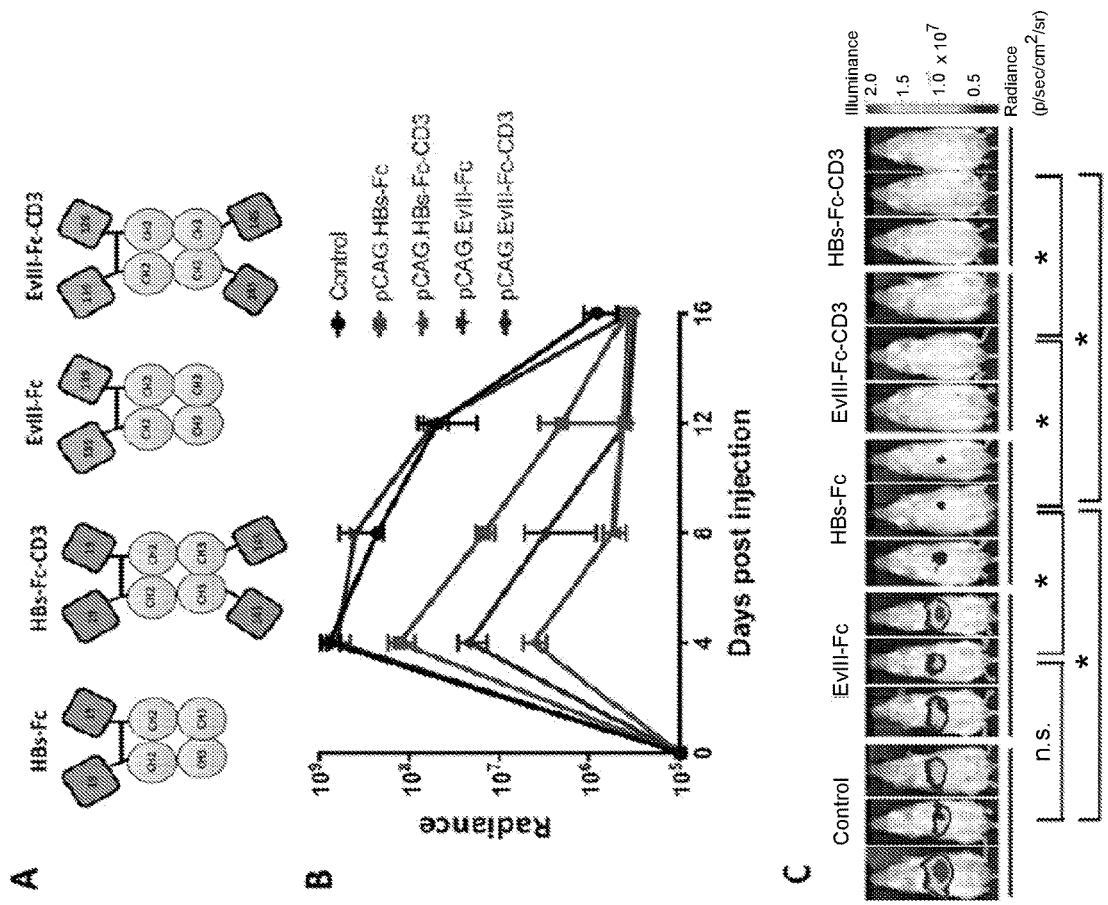
FIGS. 18A-18C. Addition of CD3 binding domain enhances anti-HBV activity of HBs-Fc. (18A) Scheme of antibody constructs (green: HBsAg-specific scFv derived from mAb 19.79.5 (19), purple: EvIII-specific scFv derived from mAb 139 (139), gray: IgG1-Fc (CH2, CH3), blue: murine CD3-specific scFv derived from mAb 145-2C11 (145). (18B) Immunocompetent mice were co-injected by hydrodynamic tail vein injection with 15 µg pCAG.HBs-Fc-CD3, pCAG.EvIIIFc-CD3, pCAG.HBs-Fc, pCAG-EvIII-Fc or control plasmid and 5 µg pHBV-ffLuc. Quantitative bioluminescence imaging data (radiance=photons/sec/cm2/sr) for all mice are shown (mean±s.e.m, n=3). (18C) Mouse images for different constructs are shown for day 4 post injection (n=3, * p<0.05) using the identical exposure time.

Including an anti-CD3 domain in HBs-Fc enhances the antiviral activity in vivo. Having established that pCAG.HBs-Fc has anti-HBV activity in vivo, it was next determined if inclusion of a scFv specific for murine CD3, which activates T cells, further enhances its antiviral activity. pCAG expression plasmids were generated encoding HBs-Fc/CD3 or EvIII-Fc/CD3 bispecific Abs by inserting the murine CD3-specific scFv from mAb 145-2C11 (Leo, et al., 1987; Jost, et al., 1996) at the c-terminus of HBs-Fc or EvIII-Fc respectively (pCAG.HBs-Fc-CD3; pCAG.EvIII-Fc-CD3; FIG. 18A).

Figure 22:
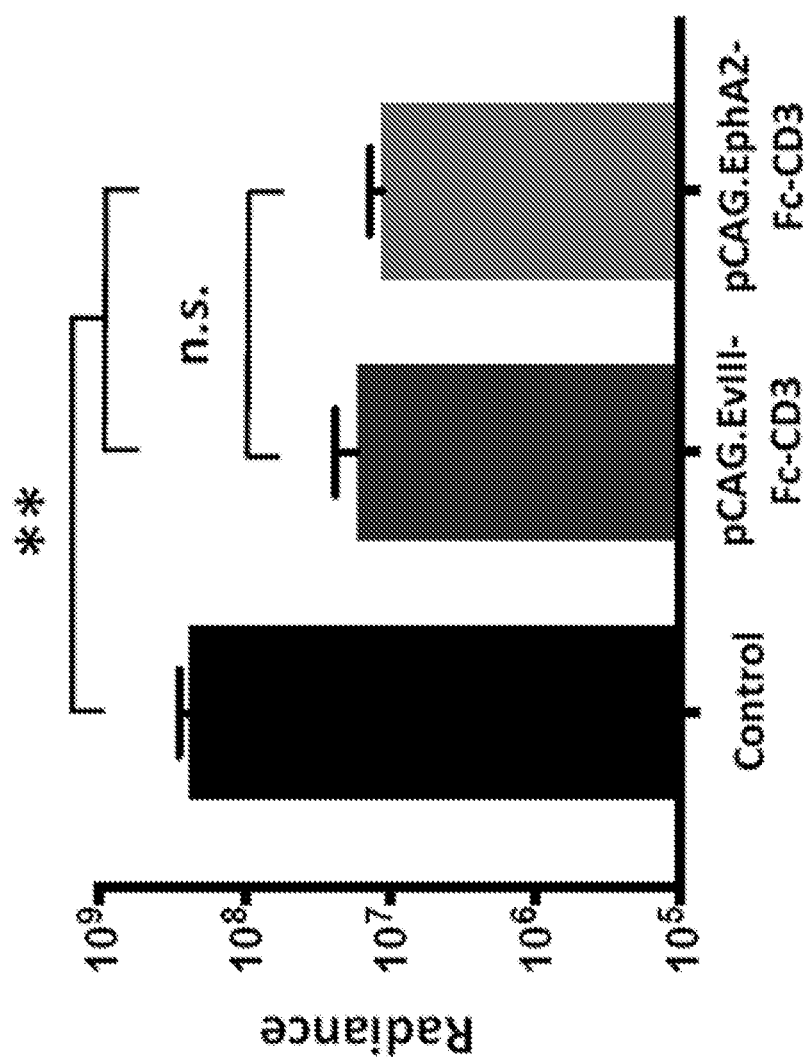
FIG. 22. In vivo expression of EphA2-Fc-CD3 had anti-HBV activity. To confirm the antigen-independent activity of EvIII-Fc-CD3, the inventors replaced the EvIII-specific scFv is pCAG.EvIII-Fc-CD3 with a scFv derived from the EphA2-specific mAb 4H5 pCAG.EphA2-Fc-CD3). Immunocompetent mice were co-injected by hydrodynamic tail vein injection with 5 µg pHBV-ffLuc and 15 µg pCA-G.EvIII-Fc-CD3, pCAG.Epha2-Fc-CD3, or control plasmid. Quantitative bioluminescence imaging data (radiance=photons/sec/cm2/sr) for all mice are shown for day 4 post injection (mean±s.e.m,), n=4, n.s.=not significant, ** p<0.005)

Keeping the total amount of DNA injected consistent, 5 µg pHBV-ffLuc was injected by HTV injection in combination with 15 µg control plasmid or plasmids encoding the respective Ab. In this study, pCAG.HBs-Fc, pCAG.HBs-Fc-CD3, EvIII-Fc, and pCAG.EvIII-Fc-CD3 were compared. Inclusion of a CD3-specific scFv enhanced the antiviral activity of pCAG.HBs-Fc 30-fold ($p<0.05$) as judged by bioluminescence imaging (FIG. 18B). Representative bioluminescence images of mice at day 4 post-injection are shown, and at this time point there was a significant difference between pCAG.EvIII-Fc and pCAG.EvIII-Fc-CD3 ($p<0.05$), indicating that bispecific Abs induce unspecific T-cell activation (FIG. 18C). Unspecific T-cell activation was confirmed with a pCAG plasmid encoding an Ab specific for the irrelevant antigen EphA2 and CD3 (pCAG.EphA2-Fc-CD3; (FIG. 22) (Iwahori, et al., 2015).

Figure 19:
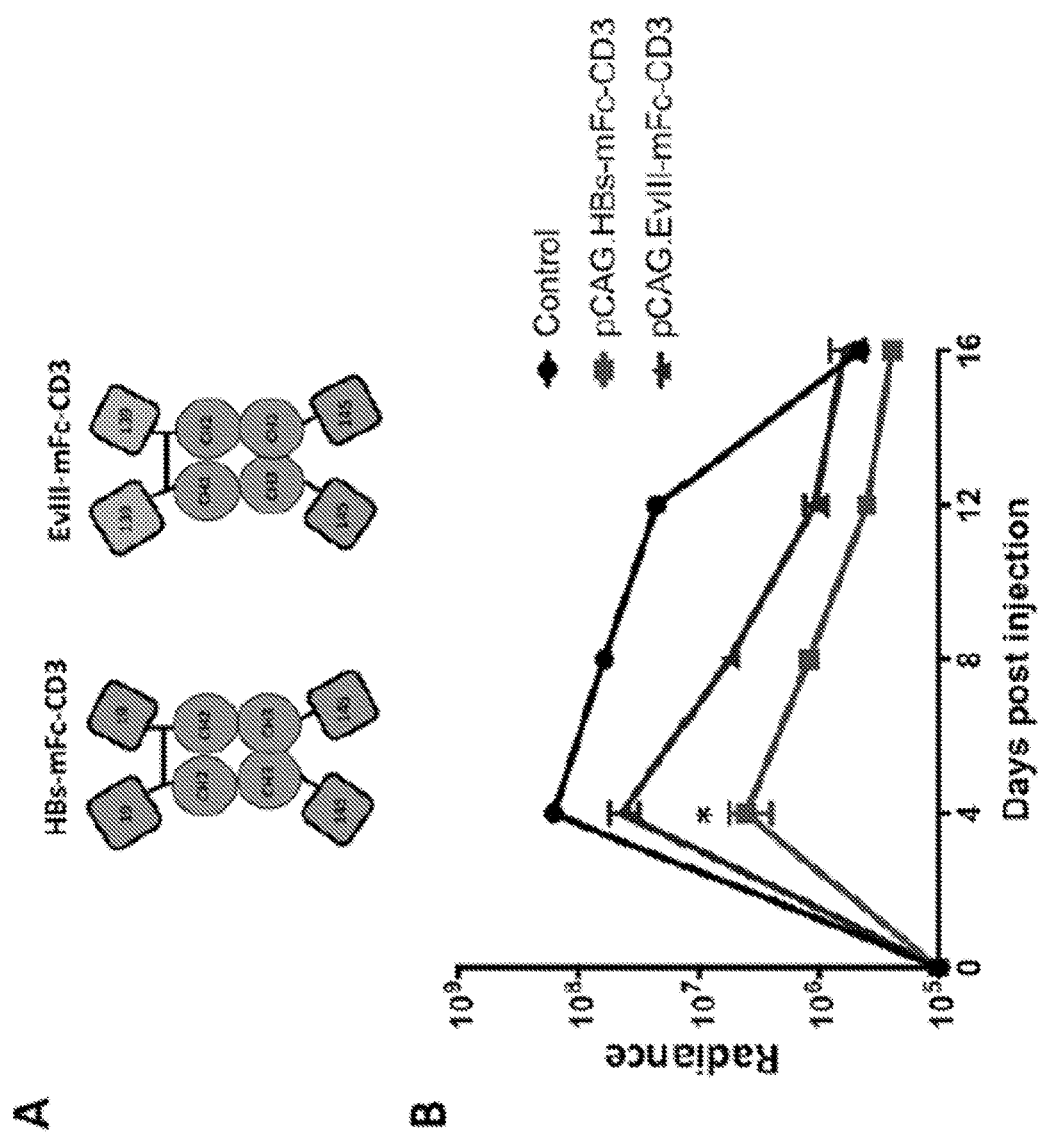
FIGS. 19A-19B. Fc receptor binding does not contribute to the anti-HBV activity of HBs-Fc-CD3. (19A) Scheme of antibody constructs (green: HBsAg-specific scFv derived from mAb 19.79.5 (19), purple: EvIII-specific scFv derived from mAb 139 (139), brown: IgG4-Fc with mutated Fc receptor binding sites (CH2, CH3), blue: murine CD3-specific scFv derived from mAb 145-2C11 (145). (19B) Immunocompetent mice were co-injected by hydrodynamic tail vein injection with 15 µg of pCAG.HBs-mFc-CD3, pCAG.EvIII-mFc-CD3, or control plasmid with 5 µg pHBV-ffLuc. Quantitative bioluminescence imaging data (radiance=photons/sec/cm2/sr) for all mice are shown (mean±s.e.m, n=3). pCAG.HBs-mFc-CD3 had significantly greater anti-HBV activity than p.CAG-EvIII-mFc-CD3 (* p<0.05)
Figure 23:
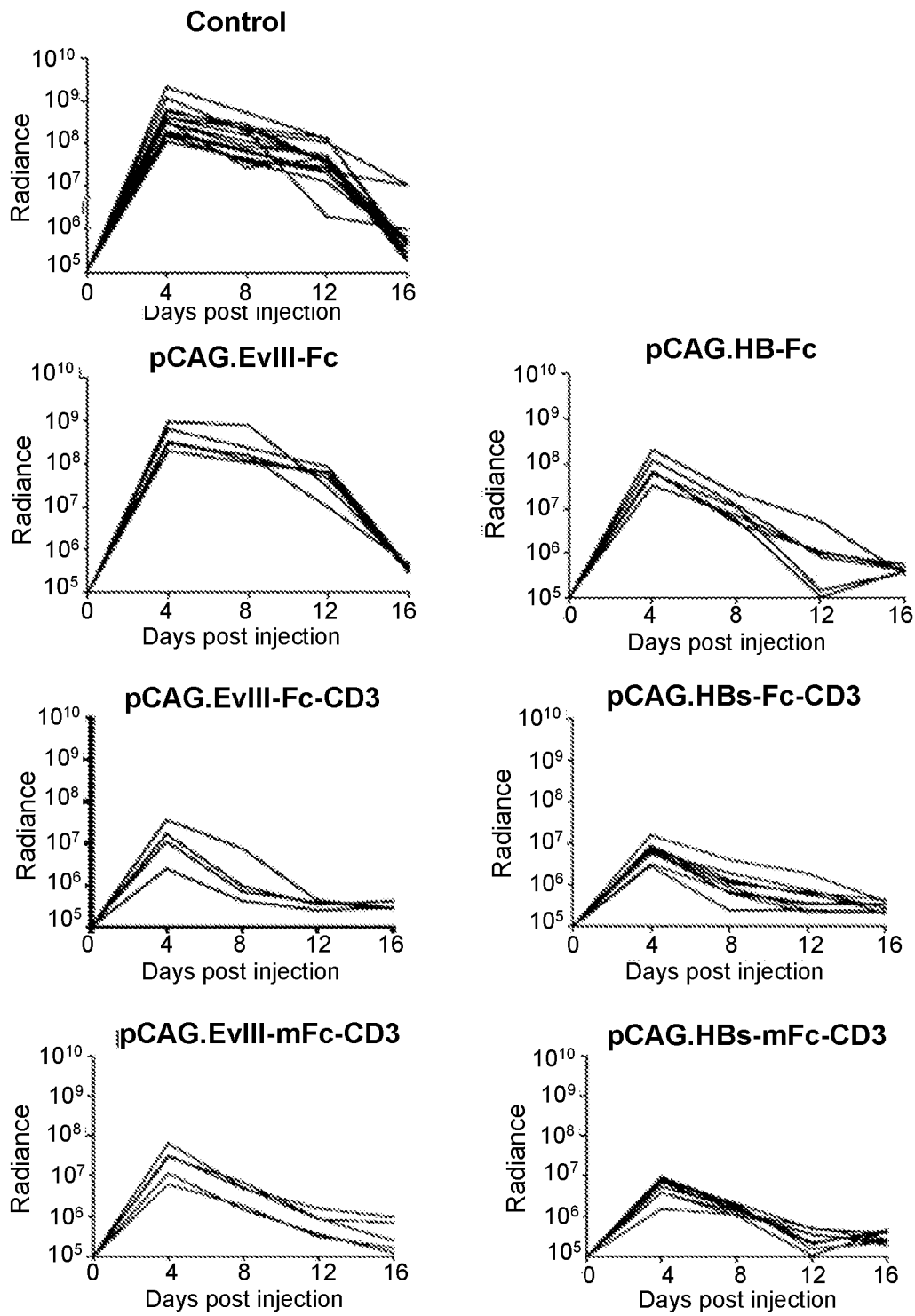
FIG. 23. The antiviral effects of in vivo expression of bispecific antibodies are consistent across multiple experiments. Collated bioluminescence data (radiance=photons/sec/cm2/sr) of replicates across the different experiments for each construct are depicted demonstrating consistent effects. Control, n=16; pCAG.EvIII-Fc, n=6; pCAG.EvIII-Fc-CD3, n=4; pCAG.EvIII-mFc-CD3, n=5; pCAG.HBs-Fc, n=6; pCAG.HBs-Fc-CD3, n=10; pCAG.HBsmFc-CD3, n=9.

To evaluate the contribution of Fc receptor-mediated phagocytosis or cell killing to the observed antiviral activity of the bispecific Abs, the inventors replaced the wildtype human IgG1 Fc domain in HBs-Fc-CD3 and EvIII-Fc-CD3 with a mutated human IgG4 Fc (mFc) domain that does not bind to Fc receptors (Hudecek, et al., 2015) (HBs-mFc-CD3; EvIII-mFc-CD3) (FIG. 19A). The antiviral activity was compared of pCAG.HBs-mFc-CD3 to pCAG.EvIII-mFc-CD3 in the model. Both bispecific Abs had antiviral activity as judged by bioluminescence imaging (FIG. 19B). HBs-mFc-CD3 had significantly greater antiviral activity at day 4 (10-fold) than EvIII-mFc-CD3 (FIG. 19B), while as shown previously using the non-mutated Fc (FIG. 18B), the HBs-Fc-CD3 had only 5-fold greater activity than the corresponding EvIII-Fc-CD3 at the same time point. This observation was confirmed with additional replicates (FIG. 23), and therefore, HBs-mFc-CD3 and EvIII-mFc-CD3 were selected as a control for subsequent studies.

Figure 24:
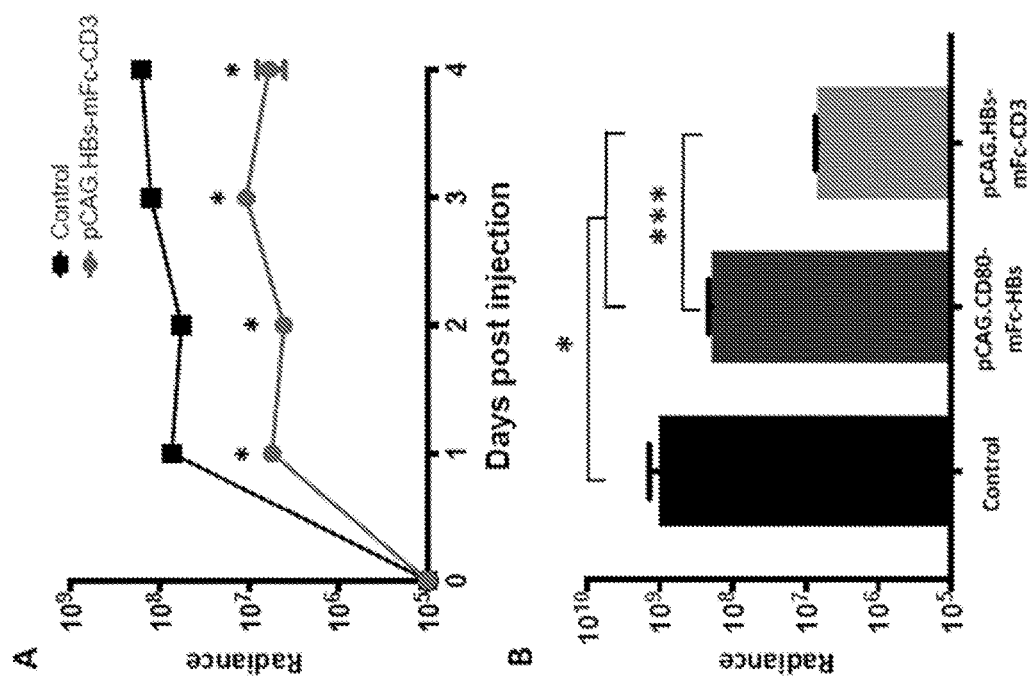
FIGS. 24A-24B. Bispecific antibodies act early after injection and through CD3 engagement to mediate antiviral activity. (24A) Bioluminescence was followed after co-injection 15 µg pCAG.HBs-mFc-CD3 or Control and 5 µg pHBV-ffLuc over the first 4 days postinjection in mice (n=3). (24B) In a similar experiment, 15 µg pCAG.HBs-mFc-CD3, 15 µg pCAG.CD80-mFc-HBs, or Control and 5 µg pHBV-ffLuc were injected into mice and measured at day 4 post-injection (n=4). Quantitative bioluminescence imaging data (radiance=photons/sec/cm2/sr) for all mice are shown (mean±s.e.m,) and significant differences denoted (*p<0.05, *** p<0.0001)

Bispecific antibodies act early after injection and in a CD3-dependent manner in the HBV model. The inventors sought to explore the kinetics of HBs-mFc-CD3 action over the course of acute clearance. The inventors co-injected 5 µg pHBV.ffLuc and 15 µg pCAG.HBs-mFc-CD3 or Control, measuring bioluminescence each day for the first 4 days. There was a 13-fold difference between control and HBs-mFc-CD3 treatment already occurs at day 1 post injection (FIG. 24A), with a similar difference maintained subsequently. This matches the published kinetics of gene expression HTV injection, which peaks at 8 hours post injection (Liu, et al., 1999), and suggests ongoing bispecific antibody production and/or antiviral T cell activation after day 1 is minimal.

The requirements were investigated for T cell signaling by substituting a different moiety for T cell stimulation, replacing the CD3 targeting portion. For this purpose, the inventors utilized the extracellular domain of the mouse CD80 protein, which can interact with CD28 expressed on T cells. This portion was cloned at the N-terminus in order to most closely resemble its natural orientation. The injected pCAG.CD80-mFc-HBs plasmid had significantly higher bioluminescence (28-fold higher) compared to pCAG.HBsmFc-CD3 plasmid (FIG. 24B), indicating that CD3 activation of T cells is critical for the observed antiviral activity.

Figure 25:
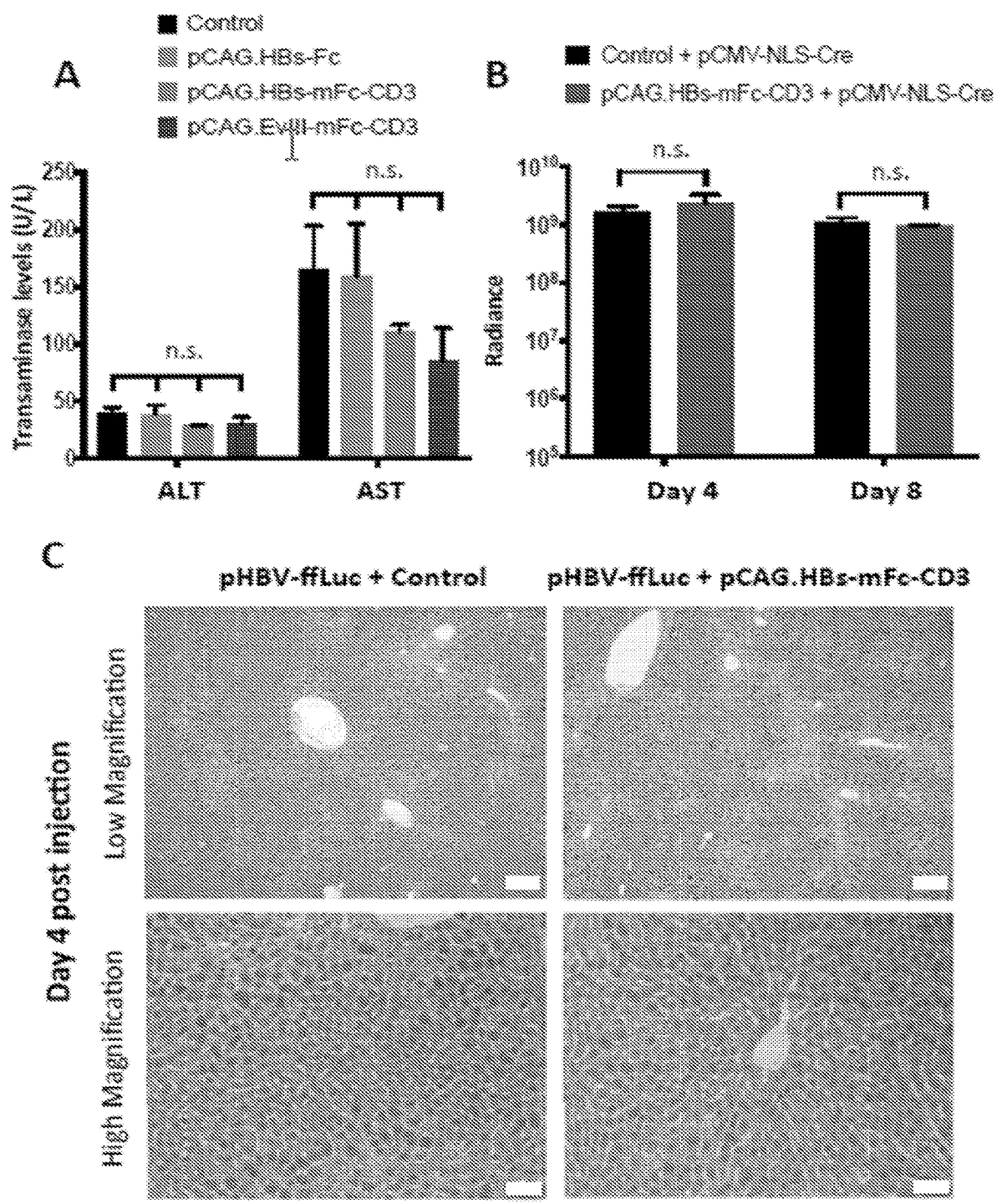
FIGS. 25A-25C. In vivo expression of HBs-mFc-CD3 in hepatocytes is nontoxic. (25A) Transaminase levels (AST and ALT) were measured at day 4 post-injection of 5 µg pHBVffLuc and 15 µg pCAG.HBs-Fc, pCAG.HBs-mFc-CD3, control plasmid (n=3), or pCAG.EvIIImFc-CD3 (n=4). (mean±s.e.m.). There was no significant (n.s.) difference between any of the groups in either ALT or AST measurements. (25B) Toxicity of HBs-mFc-CD3 expression was assessed by co-injecting pCMV-NLS-Cre with pCAG.HBs-mFc-CD3 or control plasmid into Rosa-Luc mice containing a reporter LoxP-STOP-LoxP-ffluc cassette inducing ffLuc expression in transduced, Cre recombinase-expressing hepatocytes. Quantitative bioluminescence imaging data (radiance=photons/sec/cm2/sr) for all mice are shown (mean±s.e.m., n=3). There was no significant (n.s.) difference between pCAG.HBs-mFc-CD3 and control plasmid injected groups. (25C) Liver tissue of mice was harvested at day 4 post injection in mice co-injected with 5 µg pHBV-ffLuc and 15 µg pCAG.HBs-mFc-CD3 or control plasmid, fixed in paraformaldehyde, and tissue stained with hematoxylin and eosin. No difference in tissue morphology was observed between mice (Low magnification scale bar=100 µm, High magnification scale bar=50 µm)
Figure 26:
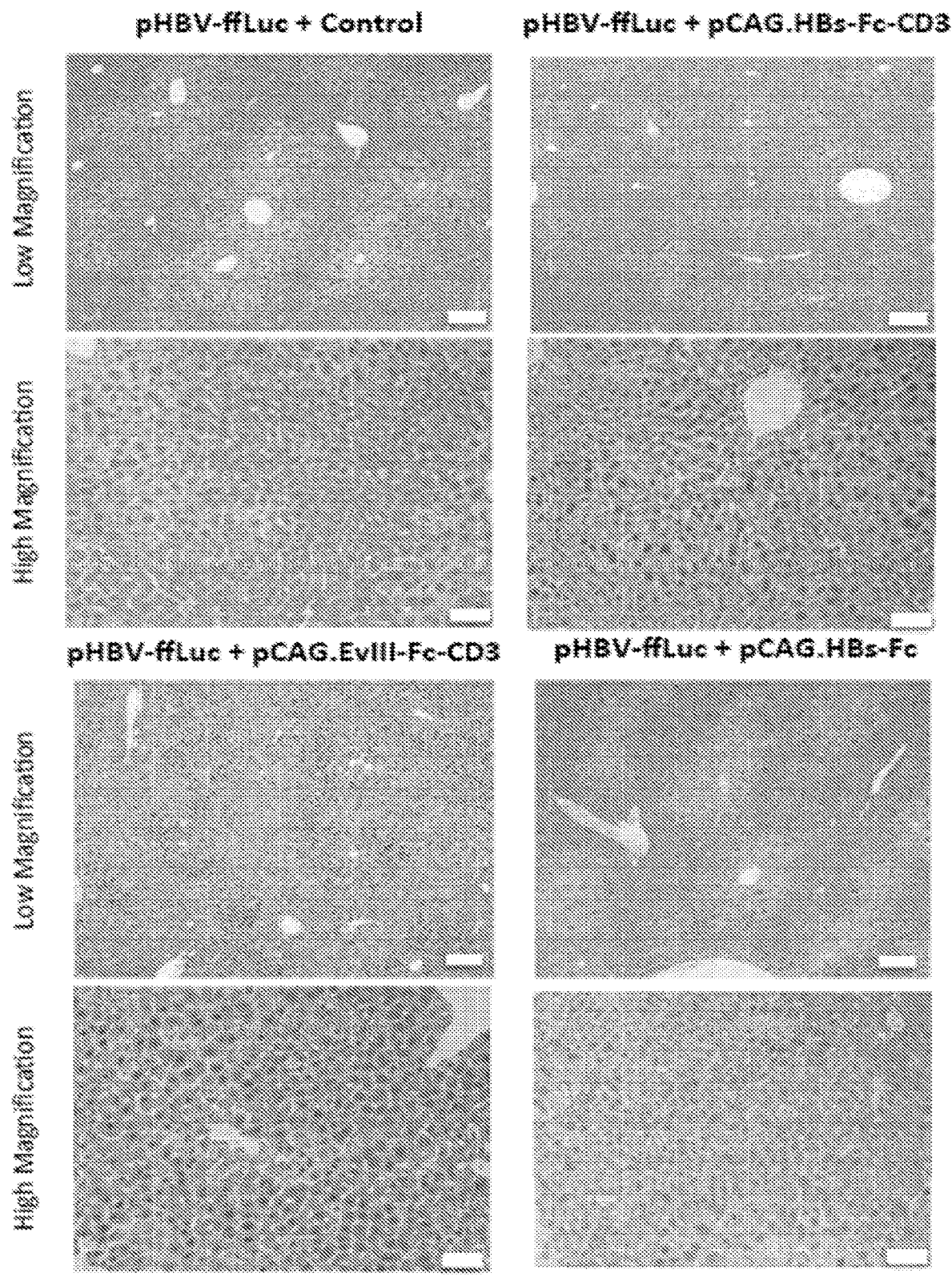
FIG. 26. In vivo expression of HBs-Fc, HBs-Fc-CD3, or EvIII-Fc-CD3 in hepatocytes is nontoxic. Liver tissue was harvested at day 4 post hydrodynamic tail vein injection of mice co-injected with 5 µg pHBV-Luc and 15 µg pCAG.HBs-Fc-CD3, pCAG.HBs-Fc, pCAG.EvIII-Fc-CD3, or control plasmid. Tissues were fixed in paraformaldehyde, and sections were stained with hematoxylin and eosin (Low magnification scale bar=100 µm, High magnification scale bar=50 µm)

In vivo expression of HBs-mFc-CD3 does not result in hepatocyte toxicity. Having demonstrated that unspecific T-cell activation contributes to the antiviral activity of HBs-mFc-CD3, unspecific hepatotoxicity triggered by HBs-mFc-CD3 expression was explored. The inventors first evaluated liver transaminase elevation that might result from bispecific antibody expression, knowing the HTV procedure itself results in transient hepatocyte injury and serum alanine aminotransferase (ALT) and aspartate aminotransferase (AST) increases (Bonamassa, et al., 2011). Measured at day 4, no difference between the conditions were observed, with levels in AST still mildly elevated at this time point post-injection (FIG. 25A). Since it is difficult to separate bulk damage from the HTV procedure versus direct transgene toxicity by examining transaminases alone, the inventors sought to more precisely study toxicity in individual transgene-modified hepatocytes. Toward this goal, a new hepatotoxicity assay was developed based on bioluminescence imaging to evaluate whether transfected hepatocytes persisted. Transgenic Rosa-Luc mice were injected by HTV injection with pCMV-NLS-Cre and pCAG.HBs-mFc-CD3 or control plasmids. The injection results in co-delivery of plasmids to the same hepatocytes; expressed Cre recombinase in transfected cells of Rosa-Luc mice induces fflLuc expression, and the resulting bioluminescence signal correlates with the number of viable, transfected hepatocytes in vivo (details in methods). HBs-mFc-CD3 expression did not reduce the bioluminescence signal on day 4 or 8 post injection versus control mice (FIG. 25B), indicating that HBs-mFc-CD3 is non-toxic in hepatocytes. These findings were confirmed using standard histological examination (H&E staining) of liver sections from mice co-injected with pHBV-fflLuc and control or pCAG.HBs-mFc-CD3 on day 4 post injection (FIG. 25C). Likewise, no histomorphological changes indicating toxicity were noted when transfecting previously used Ab constructs (FIG. 26). These histological stains also did not demonstrate notable increase in lymphocyte levels among the different test constructs at day 4, indicating that additional T cells were not recruiting into the liver, but rather tissue-resident T cells in the liver were likely activated (FIG. 26).

Figure 27:
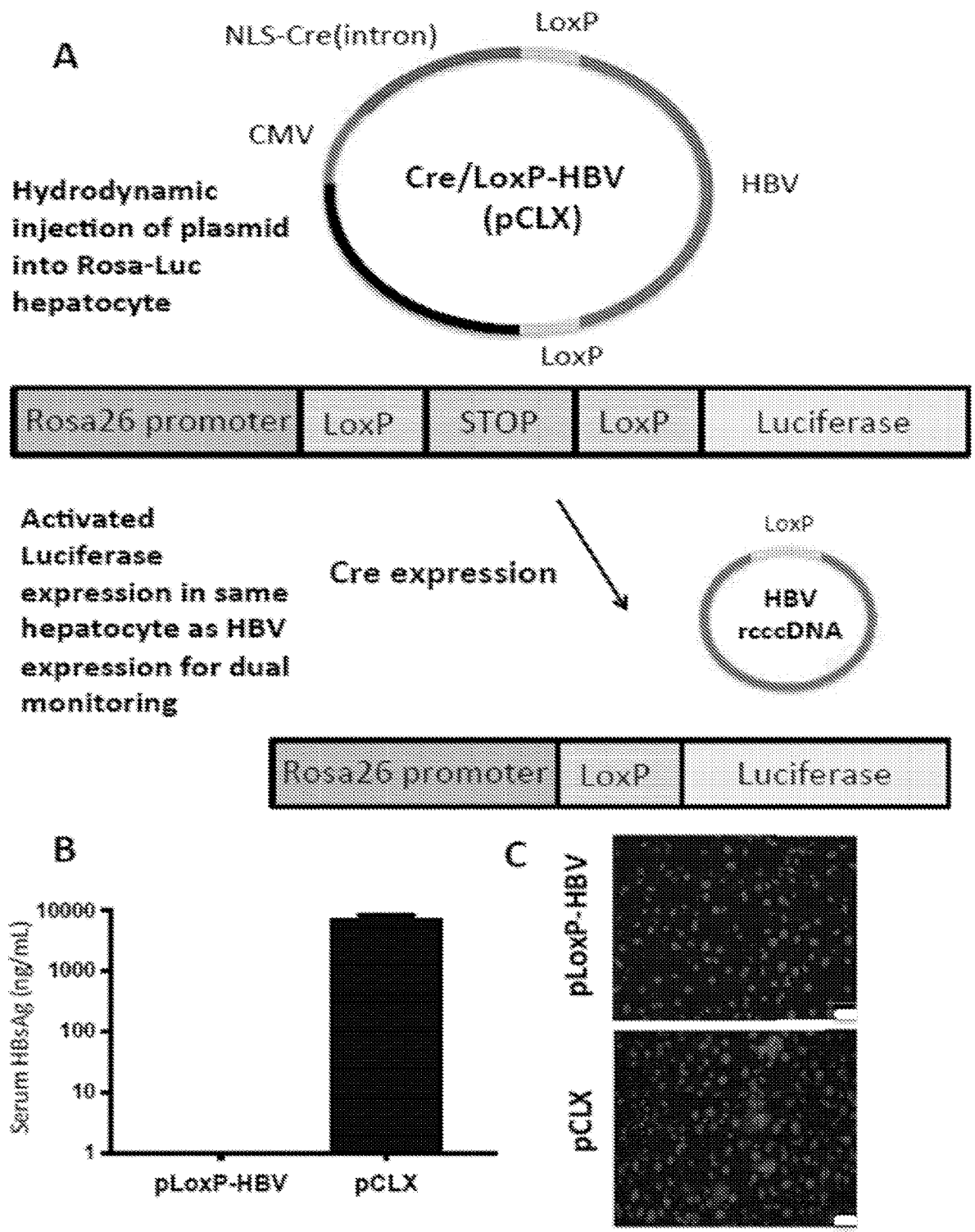
FIG. 27. Recombinant cccDNA HBV mouse model to monitor antiviral activity and hepatoxicity of antiviral agents. (A) Scheme of pCLX, which contains a CMVNLS-Cre (intron) cassette and a LoxP-HBV flanked genome (derived from pLoxP-HBV), with the LoxP site inserted between amino acid 83 and 84 of the HBV X protein. When pCLX is injected by hydrodynamic tail vein injection into Rosa-Luc mice, which contain a LoxP-STOPLoxP-ffLuc cassette driven by the Rosa26 promoter, Cre recombinase expression will i) excise and form a recombinant (r)cccDNA molecule, and ii) induce ffLuc expression in the same cell. Thus, every cell that contains HBV rcccDNA will also express ffLuc enabling toxicity monitoring of antiviral agents by non-invasive bioluminescence imaging. (B) 20 μg pCLX or pLoxP-HBV was injected by hydrodynamic tail vein injection into NSG mice. Serum was collected one week post injection and HBsAg levels were measured by ELISA (mean±s.e.m., n=4). (C) 5 μg pCLX or pLoxP-HBV were injected by hydrodynamic tail vein injection into mice and 4 days post injection liver sections were stained for HBV core (red=HBV core, blue=DAPI, scale bar=20 μm)

In vivo expression of HBs-mFc-CD3 has antiviral activity in a recombinant cccDNA HBV mouse model. Finally, the inventors wanted to explore the ability of HBs-mFc-CD3 to induce cccDNA clearance in vivo, which more closely mimics HBV transcriptional templates in human cells than plasmids carrying the HBV genome. The inventors adapted previously reported HBV murine models that utilize recombinases to generate a recombinant cccDNA-like (rcccDNA) molecule lacking bacterial DNA (Qi, et al., 2014; Guo, et al., 2016). In the system, a floxed HBV genome was constructed with an NLS-Cre recombinase (containing an internal intron) cassette driven by a CMV promoter in cis on the same plasmid (pCLX; FIG. 27A; Kruse R L, et al, manuscript in preparation). In the foxed, unexcised state with Cre recombinase, there is no detection of HBV antigens, since viral transcripts and/or proteins are interrupted by the LoxP sequences preventing expression (FIGS. 27B, 27C). After HTV injection of pCLX, Cre expression and resultant rcccDNA formation yields high level of HBsAg production and HBV core expression one week post injection, demonstrating the functionality of the model (FIGS. 27B, 27C). When pCLX is introduced into Rosa-Luc mice, the Cre recombinase also induces fflLuc expression. Thus, bioluminescence imaging serves as a non-invasive means to monitor viable transfected cells and, as in previous Rosa-Luc experiments, can be used to monitor hepatotoxicity of the bispecific Ab therapy.

Figure 20:
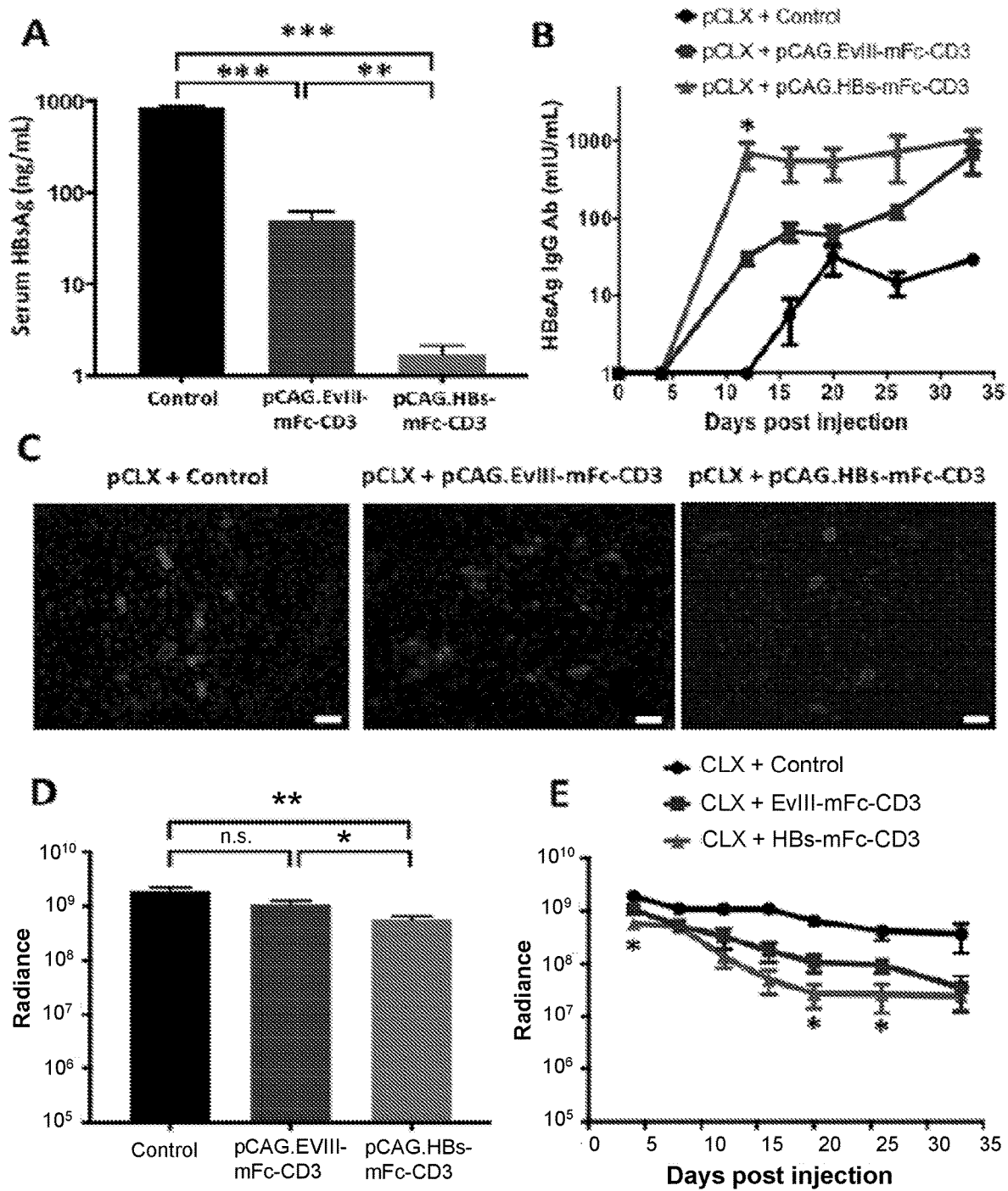
FIGS. 20A-20E. In vivo expression of HBs-mFc-CD3 in a recombinant cccDNA model of HBV has antiviral effects and induces endogenous HBsAg antibodies. Rosa-Luc mice were co-injected by hydrodynamic tail vein injection with 5 µg pCLX and 15 µg pCAG.HBs-mFc-CD3, pCAG.EvIII-mFc-CD3, or 15 µg control plasmid (n=4). (20A) HBsAg serum levels were determined by ELISA at day 4 post injection (mean±s.e.m is shown, n=4,  p<0.005, * p<0.0001). (20B) The development of host HBsAg IgG Abs was determined by ELISA at the indicated time points (mean±s.e.m is shown, n=4, * p<0.05). (20C) Tissue was harvested from mice at day 4 post injection, and HBV core protein (red) expression was assessed by immunofluorescence (blue=DAPI, scale bar=50 µm). (20D, 20E) Quantitative bioluminescence imaging data (radiance=photons/sec/cm2/sr) for all mice is shown on (20D) day 4 post injection, and (20E) during long-term follow up (mean±s.e.m, * p<0.05)

To determine the antiviral activity and safety of HBs-mFc-CD3 in the rcccDNA model, the inventors co-injected pCLX with pCAG.HBs-mFc-CD3, pCAG.EvIII-mFc-CD3 or control plasmid. On day 4 post injection 495-fold and 30-fold lower HBsAg levels were measured in pCAG.HBs-mFc-CD3 injected mice compared to mice receiving control plasmid or pCAG.EvIII-mFc-CD3 respectively (FIG. 20A). pCAG.HBs-mFc-CD3 therapy not only reduced HBsAg levels, but also induced HBsAg Abs earlier and at higher levels than p.CAG.EvIII-mFc-CD3 and controls (FIG. 20B). The antiviral activity of pCAG.HBs-mFc-CD3 therapy was also confirmed by immunofluorescence in a subset of animals on day 4 post injection, showing less HBV core expression within individual hepatocytes compared to pCA-G.EvIII-mFc-CD3 and control groups (FIG. 20C). Bioluminescence imaging was used to determine the safety of pCAG.HBs-mFc-CD3 therapy. On day 4 post injection there was 3.3-fold reduction in bioluminescence signal in pCAG.HBs-mFc-CD3 injected mice in comparison to mice receiving control plasmid (FIG. 20D), and long-term follow up revealed a further decline of bioluminescence signal of pCAG.HBs-mFc-CD3-injected mice. At day 4, 20, and 26 post injection, there were significant differences between pCAG.HBs-mFc-CD3- and pCAG.EvIII-mFc-CD3-injected mice ($p<0.05$, FIG. 20E).

Significance of Certain Embodiments

Provided herein is a novel therapeutic strategy using bispecific Abs for HBV immunotherapy. Described herein is the production of bispecific Abs in the liver leading to local T-cell activation, modulating the immune response in the organ. This differs from recombinant protein strategies, which do not specifically accumulate at tissue sites unless additional targeting moieties are included, or from using cell-based carriers for delivery (Iwahori, et al., 2015). The strategy utilizes the recruitment of naïve T cells against HBV, as opposed to relying on exhausted, dysfunctional HBV-specific T cells (Boni, et al., 2007; Park, et al., 2016) to mediate antiviral effects.

As shown herein, Abs can be expressed in hepatocytes and retain their functionality. As expected, the HBs-Fc Ab was specific and effectively mediated an antiviral effect, similar to the parent monoclonal Ab (Galum, et al., 2002; Eren, et al., 2000), while the addition of CD3-specific scFv led to an even more potent antiviral response. This antiviral effect peaked at day 1 post-injection, and the inventors were unable to detect significant levels of bispecific antibodies in the serum at day 4 likely due to activation and/or engagement with mouse T cells preventing high-level accumulation. Delivering co-stimulation through CD80 ectodomain instead of CD3-specific scFv did not elicit high-level antiviral responses. Interestingly, the bispecific Ab targeting CD3 and an unrelated antigen had significant anti-HBV activity in vivo, indicating that T-cell activation occurs independent of HBsAg binding. Fc receptor cross-linking did not play a role in enhancing antiviral effects or in facilitating T-cell activation (Rinnooy, et al., 1986), since the construct with mutated Fc receptor binding sites, HBs-mFc-CD3, had similar anti-HBV activity to HBs-Fc-CD3. Antigen-independent secretion of IFN-γ has been observed previously in vitro with the bispecific Ab format used in this study (Kuo, et al., 2012). In addition, antigen-independent T-cell activation by bispecific Abs secreted from cell lines has also been reported (Compte, et al., 2014). In specific embodiments, while not being bound by theory, the mechanism of antigen-independent T-cell activation by bispecific Abs occurs through self-aggregation, resulting in crosslinking of CD3.

In this disclosure, a novel procedure was utilized for dual monitoring of hepatocyte viability and HBV markers, adapting recombination methods to generate cccDNA-like molecules similar to previous reports (Qi, et al., 2014; Guo, et al., 2016), while also leveraging recombination of host cell reporter genes. The study was able to replicate other reports that initial T-cell effects against HBV in the liver are noncytopathic (Xia, et al., 2016), since the HBsAg levels were reduced to a much larger extent in the bispecific Ab treated groups compared to radiance, reflecting hepatocyte viability. Beyond activating T cells, HBs-mFc-CD3 may also have reduced serum HBsAg levels in the rcccDNA model via the ability of Abs to block HBsAg secretion from hepatocytes through their engagement with neonatal Fc receptor (Neumann, et al., 2010). A later decrease in radiance in groups treated with bispecific Abs was observed, similar to the pattern of final clearance of infected cells in chimpanzees (Thimme, et al., 2003). In conjunction with the higher levels of HBsAg IgG Ab production, this indicates bispecific Abs increased the host adaptive immune response versus control group.

The study differs from previous gene therapy studies demonstrating that expressing an individual cytokine, IFN-γ, in the liver has antiviral activity (Dumortier, et al., 2005; Shin, et al., 2005). When tested in a surrogate woodchuck model, adenoviral delivery of IFN-γ and TNF-α did not result in immediate reduction in the woodchuck hepatitis virus (WHV), but rather the later adaptive response against adenovirus by T cells decreased WHV viral loads, suggesting that expressing individual cytokines alone may not be sufficient (Zhu, et al., 2004). Thus activating T cells through CD3, which results in the production of not only IFN-γ, but also other proinflammatory cytokines such as TNF-α and GM-CSF (Sen, et al., 2001), might be more effective. The targeted approach to HBV is also distinct from the infusion of a recombinant TCR-like Ab to deliver IFN-α to HBV-infected hepatocytes (Ji, et al., 2012), and gene therapy with a Apo-A1/IFN-α fusion protein (Berraondo, et al., 2015). In addition, the strategy targeting HBsAg and CD3 format differs from previous protein-based bispecific antibody strategies targeting two different epitopes on HBsAg (Park, et al., 2000; Tan, et al., 2013), as well as a strategy targeting HBx and CD3 for hepatocellular carcinoma (Liao, et al., 1996).

In some embodiments, one can employ clinical translatable liver gene delivery systems, such as AAV (Nathwani, et al., 2011) or mRNA-nanoparticles (Thess, et al., 2015; DeRosa, et al., 2016). In a recent study, mRNA-nanoparticles effectively targeted liver in mice and systemically secreted bispecific antibodies to engage claudin-6 and CD3 triggering T-cell cytotoxicity against subcutaneously injected tumors (Stadler et al., 2017). This strategy is applicable to methods herein to treat in situ liver disease, in specific embodiments. Another limitation is that HTV injection results in an acute model of HBV, rather than a chronic HBV mouse model, which can be established in immuno-competent mice with AAV (Dion, et al., 2013) or low-dose adenoviral (Huang, et al., 2012) delivery of HBV genomes.

In conclusion, a novel therapeutic approach to target HBV infection by expressing bispecific Abs in hepatocytes, leading to a local and predominantly noncytopathic immune response against HBV, is provided herein. The approach is of value not only for treating HBV but also other viral liver diseases.

Examples of Materials and Methods

Plasmid constructs. Generation of Ab constructs: A codon-optimized minigene was synthesized by IDTDNA (Coralville, Iowa) containing the immunoglobulin heavy-chain leader peptide (MDWIWRILFLVGAATGAHS; SEQ ID NO.), the HBs-specific mAb 19.79.5 (Eren, et al., 1998) heavy-chain, a glycine (G) serine (S) linker [(G4S)3], and the 19.79.5 light-chain flanked by 5' XhoI and 3' BamHI sites. The human IgG1 Fc domain was PCR amplified from a plasmid encoding a CAR containing a IgG1 Fc hinge with the PCR primers containing 5' BamHI and NotI 3'. The minigene and PCR product was cloned into pCAG by three-way ligation to create pCAG-HBs-Fc. To create the EvIII-Fc control plasmid, the 139 scFv specific for EGFRvIII was PCR cloned from pSFG.139-CD3-I-mOrange with PCR primers containing 5' XhoI and 3' BamHI sites. Three-way ligation reaction was performed to create pCAG-EvIII-Fc. Cloning was confirmed by sequencing (Lone Star Labs, Houston, Tex.).

Generation of bispecific Ab constructs: The 145-2C11 (Leo, et al., 1987) scFv specific for murine CD3 was PCR amplified from pRV2011.145-2C11-1D3-I-Thy1.1 with 5' EcoRV and 3' NotI sites. Four-way ligations was performed with 5' XhoI-leader-HBs or EvIII scFv-3' BamHI, 5' BamHI-Fc-3' EcoRV, 5' EcoRV-145-2C11 scFv-3' NotI, and pCAG digested with XhoI and NotI to generate pCAG.HBs-Fc-CD3 and pCAG.EvIII-Fc-CD3. pCAG.HBs-mFc-CD3 and pCAG.EvIII-mFc-CD3 were generated in a similar fashion except a codon optimized minigene (IDTDNA, Coralville, Iowa) encoding the human IgG4 Fc with mutated Fc binding sites (Hudecek, et al., 2015) and flanking 5' BamHI and 3' EcoRV sites was used instead of 5' BamHI-Fc-3' EcoRV. pCAG.CD80-mFc-HBs was generated by synthesizing the extracellular domain including leader sequence of murine CD80 (B7.1) protein between 5'-XhoI and 3' BamHI sites. Separately, PCR amplification of HBs scFv added 5' EcoRV and 3' NotI sites. Four-way ligation reaction with 5'-XhoI-CD80-3' BamHI, 5' BamHI-mFc-3' EcoRV, and 5' EcoRV-HBs-3' NotI, and pCAG digested with XhoI and NotI was performed to generate pCAG.CD80-mFc-HBs. Cloning was confirmed by sequencing (Lone Star Labs, Houston, Tex.).

Generation of pCAG: The pCAG vector was constructed from the pCIG vector (containing the hybrid promoter CMV enhancer chicken beta actin (CAG) promoter, rabbit beta globin 3'UTR, polyadenylation sequence, IRES-NLS-GFP, and SV40 origin of replication) by removing IRES-NLS-GFP leaving XhoI and NotI sites for inserting transgenes (FIG. 21A).

Generation of pHBV-ffLuc: pHBV-ffLuc was generated by inserting a GFP-2A-ffLuc expression cassette by PCR cloning (provided by Dr. Inder Verma, Salk Institute, San Diego, Calif.) into the SmaI and SacI sites of pSP65ayw1.3 (provided by Dr. Stefan Wieland, University of Basel, Switzerland). pSP65ayw1.3 encodes an over-length HBV genome from genotype D, subtype ayw, GenBank V01460. The SmaI site is located at the 3'-end of the over-length HBV genome and the PCR primers for GFP-2A-ffLuc subcloning were designed so that GFP-2A-ffLuc translation is in frame with core protein translation at the 3' end of the HBV genome (see FIG. 28 for more sequence information). Cloning was confirmed by sequencing (Lone Star Labs, Houston, Tex.).

Bioluminescence imaging. The IVIS® system (Xenogen Corp., Alameda, Calif.) was used for bioluminescence imaging. Mice were anesthetized with isofluorane and injected intraperitoneal with 200 µL of 7.5 mg/mL luciferin solution (GoldBio, Olivette, Mo.). Luciferin was allowed to circulate for 10 minutes post-injection, and mice were placed ventral side up and imaged promptly thereafter. Luminescence signals were quantified using Living Image 4.2 software (Caliper Life Sciences, Hopkinton, Mass.) with a region of interest (ROI) circling the area over the liver.

HBsAg ELISA. HBsAg levels were determined as previously described (Billioud, et al., 2016). Briefly, serum HBsAg levels were evaluated with commercially sold ELISA kits according to manufacturer's instructions (International Immuno Diagnostics, Foster City, Calif.). Quantification of serum HBsAg was made by comparing serial dilutions of known standards (Alpha Diagnostic International, San Antonio, Tex.). HBsAg levels were reported as ng/mL, consistent with the standards utilized. The conversion ratio to IU/mL is not provided by the manufacturer, but many kits have conversions of 1 or 10 ng/mL to 1 IU/mL HBsAg as approximate guidelines (Locarnini, et al., 2012).

HBsAg IgG antibody ELISA. Serum HBsAg IgG Ab levels were quantified by ELISA according to manufacturer's instructions (Alpha Diagnostic International, San Antonio, Tex.). HBsAg IgG Ab levels were reported as mIU/mL. The ELISA assay can detect both human and mouse immunoglobulin.

Transaminase analysis. Serum alanine aminotransferase (ALT) and aspartate aminotransferase (AST) were measured by the Comparative Pathology Laboratory (Baylor College of Medicine, Houston, Tex.) using COBAS INTEGRA 400 plus analyzer (Roche Diagnostics, Indianapolis, Ind.).

Animal Experiments. All animal experiments followed a protocol approved by the Baylor College of Medicine Institutional Animal Care and Use Committee. For all experiments using immunocompetent mice, the Rosa-Luc strain from Jackson Labs (FVB.129S6(B6)-Gt(ROSA)26Sortm1(Luc)Kael/J) was utilized in which the expression of the firefly luciferase (Luc) gene is blocked by a loxP-flanked STOP fragment placed between the Luc sequence and the Gt(ROSA)26Sor promoter. Even though most experiments did not utilize the endogenous luciferase reporter, using Rosa-Luc mice for all experiments reduced the risk of inter-strain variability. Rosa-Luc mice, aged 6-10 weeks, were selected for hydrodynamic tail vein injection. As a filler or control plasmid so that equal amount of DNA was injected in each group of mice, pCMV-*Gaussia* luciferase (ThermoFisher, Waltham, Mass.) was used. Plasmid DNA was diluted into 0.9% normal saline solution to a total volume equaling 10% of murine body weight. Mice were placed under a heat lamp for 5-10 minutes to dilate the lateral tail veins, and injection performed over 4-6 seconds (Kovacsics, et al., 2014). Mice were bled retro-orbitally, and serum collected after centrifugation for 30 minutes at 2.3 G. Serum was stored at −80° C. until further use for HBsAg ELISA and HBsAg IgG ELISA quantification.

Histology. Frozen tissue slides from livers were fixed with 4% PFA for 10 minutes, and stained for HBV core overnight at 4° C. in PBS-T buffer (PBS 1× containing 0.5% BSA and 0.2% of triton-100) using the primary antibody: rabbit anti-hepatitis B virus core antigen (Dako/Agilent, Santa Clara, Calif.). Primary antibody was washed with PBS 1×, and slides were incubated with Alexa-Fluor secondary antibodies (Molecular Probes, Eugune, Oreg.) in PBS-T buffer. Vectashield plus DAPI (Vector Labs, Burlingame, Calif.) was used for slides mounting. In other experiments, liver tissue was fixed in 4% paraformaldehyde overnight, and serial sections of paraffin-embedded liver stained with hematoxylin & eosin.

Statistical analysis. Statistical analysis was performed using GraphPad Prism 7 software (GraphPad Software, Inc., La Jolla, Calif.). Data measurements are presented as mean+/−standard error of mean (s.e.m.). Mean differences were tested using appropriate tests including unpaired, parametric, one-tailed t-tests. Significance level used was $p<0.05$, unless otherwise specified.

REFERENCES

All patents and publications mentioned in the specification are indicative of the level of those skilled in the art to which the disclosure pertains. All patents and publications are herein incorporated by reference to the same extent as if each individual publication was specifically and individually indicated to be incorporated by reference.

PATENTS AND PATENT APPLICATIONS

US 2002/0151509
US 2011/0184049

PUBLICATIONS

Aliño, S. F., Crespo, A. & Dasi, F. Long-term therapeutic levels of human alpha-1 antitrypsin in plasma after hydrodynamic injection of nonviral DNA. Gene Therapy 10, 1672-1679 (2003).

Billioud, G. et al. In vivo reduction of hepatitis B virus antigenemia and viremia by antisense oligonucleotides. Journal of Hepatology 64, 781-789 (2016).

Bohne, F. et al. T Cells Redirected Against Hepatitis B Virus Surface Proteins Eliminate Infected Hepatocytes. Gastroenterology 134, 239-247 (2008).

Boni, C. et al. Characterization of hepatitis B virus (HBV)-specific T-cell dysfunction in chronic HBV infection. Journal of Virology 81, 4215-4225 (2007).

Brischwein, K. et al. Strictly target cell-dependent activation of T cells by bispecific single-chain antibody constructs of the BiTE class. Journal of immunotherapy (Hagerstown, Md.: 1997) 30, 798-807 (2007).

Cassidy, A., Mossman, S., Olivieri, A., De Ridder, M. & Leroux-Roels, G. Hepatitis B vaccine effectiveness in the face of global HBV genotype diversity. Expert Review of Vaccines 10, 1709-1715 (2011).

Chen, S.-H., Wu, H.-L., Kao, J.-H. & Hwang, L.-H. Persistent Hepatitis B Viral Replication in a FVB/N Mouse Model: Impact of Host and Viral Factors. PLoS ONE 7, e36984-12 (2012).

Compte, M. et al. Functional comparison of single-chain and two-chain anti-CD3-based bispecific antibodies in gene immunotherapy applications. OncoImmunology 3, e28810 (2014).

Compte, M., Nuñez-Prado, N., Sanz, L. & Alvarez-Vallina, L. In vivo Secretion of Bispecific Antibodies Recruiting Lymphocytic Effector Cells. Antibodies 2, 415-425 (2013).

Dong, C. et al. Targeting hepatitis B virus cccDNA by CRISPR/Cas9 nuclease efficiently inhibits viral replication. Antiviral Research 118, 110-117 (2015).

Durantel, D. & Zoulim, F. New antiviral targets for innovative treatment concepts for hepatitis B virus and hepatitis delta virus. Journal of Hepatology 64, S117-S131 (2016).

Eren, R. et al. Human monoclonal antibodies specific to hepatitis B virus generated in a human/mouse radiation chimera: the Trimera system. Immunology 93, 154-161 (1998).

Eren, R. et al. Preclinical Evaluation of Two Human Anti-Hepatitis B Virus (HBV) Monoclonal Antibodies in the HBV-Trimera Mouse Model and in HBV Chronic Carrier Chimpanzees. Hepatology 32, 588-596 (2000).

Falk, I., Potocnik, A. J., Barthlott, T., Levelt, C. N. & Eichmann, K. Immature T cells in peripheral lymphoid organs of recombinase-activating gene-1/-2-deficient mice. Thymus dependence and responsiveness to anti-CD3 epsilon antibody. J. Immunol. 156, 1362-1368 (1996).

Galun, E. Clinical evaluation (phase I) of a combination of two human monoclonal antibodies to HBV: Safety and antiviral properties. Hepatology 35, 673-679 (2002).

Guidotti, L. G. et al. Immunosurveillance of the liver by intravascular effector CD8(+) T cells. Cell 161, 486-500 (2015).

Haile, S. T., Dalal, S. P., Clements, V., Tamada, K. & Ostrand-Rosenberg, S. Soluble CD80 restores T cell activation and overcomes tumor cell programmed death ligand 1-mediated immune suppression. J. Immunol. 191, 2829-2836 (2013).

Hösel, M. et al. Hepatitis B virus infection enhances susceptibility toward adeno-associated viral vector transduction in vitro and in vivo. Hepatology 59, 2110-2120 (2014).

Hudecek, M. et al. The nonsignaling extracellular spacer domain of chimeric antigen receptors is decisive for in vivo antitumor activity. Cancer Immunol Res 3, 125-135 (2015).

Iwahori, K. et al. Engager T cells: a new class of antigen-specific T cells that redirect bystander T cells. Mol Ther 23, 171-178 (2015).

Jost, C. R., Titus, J. A., Kurucz, I. & Segal, D. M. A single-chain bispecific Fv2 molecule produced in mammalian cells redirects lysis by activated CTL. Molecular Immunology 33, 211-219 (1996).

Karimova, M. et al. CRISPR/Cas9 nickase-mediated disruption of hepatitis B virus open reading frame S and X. Nature Publishing Group 5, 13734 (2015).

Kay, M. A. et al. Expression of human alpha 1-antitrypsin in dogs after autologous transplantation of retroviral transduced hepatocytes. Proc Natl Acad Sci USA 89, 89-93 (1992).

Krebs, K. et al. T Cells Expressing a Chimeric Antigen Receptor That Binds Hepatitis B  Virus Envelope Proteins Control Virus Replication in Mice. Gastroenterology 1-10 (2013). doi:10.1053/j.gastro.2013.04.047

Kuo, S. R., Wong, L. & Liu, J. S. Engineering a CD123× CD3 bispecific scFv immunofusion for the treatment of leukemia and elimination of leukemia stem cells. Protein Engineering Design and Selection 25, 561-570 (2012).

Leo, O., Foo, M., Sachs, D. H., Samelson, L. E. & Bluestone, J. A. Identification of a monoclonal antibody specific for a murine T3 polypeptide. Proc Natl Acad Sci USA 84, 1374-1378 (1987).

Liang, S.-Q. et al. A Mouse Model for Studying the Clearance of Hepatitis B Virus In vivo Using a Luciferase Reporter. PLoS ONE 8, e60005-9 (2013).

Liu, F., Song, Y. & Liu, D. Hydrodynamics-based transfection in animals by systemic administration of plasmid DNA. Gene Therapy 6, 1258-1266 (1999).

Liu, S. et al. Human hepatitis B virus surface and e antigens inhibit major vault protein signaling in interferon induction pathways. Journal of Hepatology 62, 1015-1023 (2015).

Lucifora, J. et al. Specific and Nonhepatotoxic Degradation of Nuclear Hepatitis B Virus cccDNA. Science 343, 1221-1228 (2014).

Mau-Sorensen, M. et al. A phase I trial of intravenous catumaxomab: a bispecific monoclonal antibody targeting EpCAM and the T cell coreceptor CD3. Cancer Chemother. Pharmacol. 75, 1065-1073 (2015).

McMahon, B. J. et al. Antibody levels and protection after hepatitis B vaccine: results of a 22-year follow-up study and response to a booster dose. J. Infect. Dis. 200, 1390-1396 (2009).

Morgan, R. A. et al. Recognition of glioma stem cells by genetically modified T cells targeting EGFRvIII and development of adoptive cell therapy for glioma. Human Gene Therapy 23, 1043-1053 (2012).

Nathwani, A. C. et al. Adenovirus-associated virus vector-mediated gene transfer in hemophilia B. N. Engl. J. Med. 365, 2357-2365 (2011).

Neumann, A. U. et al. Novel mechanism of antibodies to hepatitis B virus in blocking viral particle release from cells. Hepatology 52, 875-885 (2010).

Nguyen, A. T., Dow, A. C., Kupiec-Weglinski, J., Busuttil, R. W. & Lipshutz, G. S. Evaluation of gene promoters for liver expression by hydrodynamic gene transfer. The Journal of surgical research 148, 60-66 (2008).

Park, J.-J. et al. Hepatitis B Virus—Specific and Global T-Cell Dysfunction in Chronic Hepatitis B. Gastroenterology 150, 684-695.e5 (2016).

Paul, A. J., Schwab, K. & Hesse, F. Direct analysis of mAb aggregates in mammalian cell culture supernatant. BMC Biotechnol. 14, 99 (2014).

Przepiorka, D. et al. FDA Approval: Blinatumomab. Clin Cancer Res 21, 4035-4039 (2015).

Rai, U. et al. A New Method to Determine Antigen-Specific CD8+ T Cell Activity in vivo by Hydrodynamic Injection. Biomolecules 2, 23-33 (2012).

Ramanan, V. et al. CRISPR/Cas9 cleavage of viral DNA efficiently suppresses hepatitis B virus. Nature Publishing Group 5, 10833 (2015).

Ribera, J.-M., Ferrer, A., Ribera, J. & Genescá, E. Profile of blinatumomab and its potential in the treatment of relapsed/refractory acute lymphoblastic leukemia. Onco Targets Ther 8, 1567-1574 (2015).

Schilling, R. et al. Endocytosis of hepatitis B immune globulin into hepatocytes inhibits the secretion of hepatitis B virus surface antigen and virions. Journal of Virology 77, 8882-8892 (2003).

Schlereth, B. et al. Potent inhibition of local and disseminated tumor growth in immunocompetent mouse models by a bispecific antibody construct specific for Murine CD3. Cancer Immunol. Immunother. 55, 785-796 (2006).

Seeger, C. & Sohn, J. A. Targeting Hepatitis B Virus With CRISPR/Cas9. Mol Ther Nucleic Acids 3, e216 (2014).

Smith, J. A., Tso, J. Y., Clark, M. R., Cole, M. S. & Bluestone, J. A. Nonmitogenic anti-CD3 monoclonal antibodies deliver a partial T cell receptor signal and induce clonal anergy. J Exp Med 185, 1413-1422 (1997).

Spiess, C., Zhai, Q. & Carter, P. J. Alternative molecular formats and therapeutic applications for bispecific antibodies. Molecular Immunology 1-12 (2015). doi:10.1016/j.molimm.2015.01.003

Staerz, U. D. & Bevan, M. J. Hybrid hybridoma producing a bispecific monoclonal antibody that can focus effector T-cell activity. Proc Natl Acad Sci USA 83, 1453-1457 (1986).

Staerz, U. D., Kanagawa, 0. & Bevan, M. J. Hybrid antibodies can target sites for attack by T cells. Nature 314, 628-631 (1985).

Tan, W. et al. A bispecific antibody against two different epitopes on hepatitis B surface antigen has potent hepatitis B virus neutralizing activity. MAbs 5, 946-955 (2013).

Thess, A. et al. Sequence-engineered mRNA Without Chemical Nucleoside Modifications Enables an Effective Protein Therapy in Large Animals. Mol Ther 23, 1-9 (2015).

Thimme, R. et al. CD8(+) T cells mediate viral clearance and disease pathogenesis during acute hepatitis B virus infection. Journal of Virology 77, 68-76 (2003).

van Nunen, A. B. et al. Efficacy and safety of an intravenous monoclonal anti-HBs in chronic hepatitis B patients. Liver 21, 207-212 (2001).

Viecelli, H. M. et al. Treatment of phenylketonuria using minicircle-based naked-DNA gene transfer to murine liver. Hepatology 60, 1035-1043 (2014).

Weidle, U. H., Tiefenthaler, G., Weiss, E. H., Georges, G. & Brinkmann, U. The intriguing options of multispecific antibody formats for treatment of cancer. Cancer Genomics Proteomics 10, 1-18 (2013).

Wooddell, C. I. et al. Hepatocyte-targeted RNAi therapeutics for the treatment of chronic hepatitis B virus infection. Mol Ther 21, 973-985 (2013).

Xia, Y. et al. Interferon-γ and Tumor Necrosis Factor-α Produced by T Cells Reduce the HBV Persistence Form, cccDNA, Without Cytolysis. Gastroenterology 150, 194-205 (2016).

Xu, Y. et al. HBsAg inhibits TLR9-mediated activation and IFN-alpha production in plasmacytoid dendritic cells. Molecular Immunology 46, 2640-2646 (2009).

Yang, P. L., Althage, A., Chung, J. & Chisari, F. V. Hydrodynamic injection of viral DNA: a mouse model of acute hepatitis B virus infection. Proc Natl Acad Sci USA 99, 13825-13830 (2002).

Ying, T., Chen, W., Gong, R., Feng, Y. & Dimitrov, D. S. Soluble Monomeric IgG1 Fc. J. Biol. Chem. 287, 19399-19408 (2012).

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A composition comprising a polynucleotide encoding a secretable polypeptide that comprises at least one Hepatitis B surface antigen-binding antibody and at least one immunostimulatory antibody, wherein the composition comprises the same or a different polynucleotide that encodes a cytoprotective agent, wherein the cytoprotective agent is Bcl2, Bcl-XL, Mcl-1, CED-0, Bfl-1, X-linked inhibitor of apoptosis protein (XIAP), c-IAP1, C-IAP2, NAIP, Livin, Survivin, serpin proteinase inhibitor 9, or SERPINB4.

2. The composition of claim 1, wherein the cytoprotective agent is a nucleic acid or a polypeptide.

3. The composition of claim 2, wherein the cytoprotective agent is an mRNA that comprises untranslated sequences that are targetable by an miRNA molecule of an individual.

4. A polypeptide having an amino acid sequence selected from SEQ ID NOs: 15-21, 38, 40, 41 and 43.

5. A composition comprising a polynucleotide encoding a secretable polypeptide that comprises at least one Hepatitis B surface antigen-targeting binding antibody and at least one immunostimulatory antibody, wherein said polynucleotide comprises a liver-specific promoter selected from a thyroxine binding globulin (TBG) promoter, an apoE promoter, and an alpha1-antitrypsin promoter, such that it is capable of producing said secretable polypeptide inside liver cells of a mammalian subject without toxicity as compared to an untreated mammalian subject.

* * * * *

SEQUENCE LISTING

```
<160> NUMBER OF SEQ ID NOS: 45

<210> SEQ ID NO 1
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Pro Arg Ala
            20                  25                  30

Ser Ser Met Val Ser Lys Gly Glu Glu Leu Phe Thr Gly Val Val Pro
        35                  40                  45

Ile Leu Val Glu Leu Asp Gly Asp Val Asn Gly His Lys Phe Ser Val
    50                  55                  60

<210> SEQ ID NO 2
<211> LENGTH: 297
<212> TYPE: DNA
<213> ORGANISM: Artificial Sequence
<220> FEATURE:
<223> OTHER INFORMATION: Synthetic Primer

<400> SEQUENCE: 2
attggtctgc gcaccagcac catgcaactt tttcacctct gcctaatcat ctcttgttca        60
tgtcctactg ttcaagcctc caagctgtgc cttgggtggc tttggggcat ggacatcgac       120
```

```
ccttataaag aatttggagc tactgtggag ttactctcgt ttttgccttc tgacttcttt    180
ccttcagtac gagatccccg ggcgagctcg atggtgagca agggcgagga gctgttcacc    240
ggggtggtgc ccatcctggt cgagctggac ggcgacgtaa acggccacaa gttcagc       297
```

<210> SEQ ID NO 3
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 3

Gln Val Gln Leu Val Glu Ser Gly Gly Gly Val Gln Pro Gly Gly
1               5                   10                  15

Ser Leu Arg Leu Ser Cys Ala Pro Ser Gly Phe Val Phe Arg Ser Tyr
            20                  25                  30

Gly Met His Trp Val Arg Gln Thr Pro Gly Lys Gly Leu Glu Trp Val
        35                  40                  45

Ser Leu Ile Trp His Asp Gly Ser Asn Arg Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Ala Arg Glu Arg Leu Ile Ala Ala Pro Ala Ala Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Ser Tyr Val Leu Thr Gln Pro Pro
    130                 135                 140

Ser Val Ser Val Ala Pro Gly Lys Thr Ala Arg Ile Ser Cys Gly Gly
145                 150                 155                 160

Asn Asn Ile Gly Thr Lys Asn Val His Trp Tyr Gln Gln Lys Pro Gly
                165                 170                 175

Gln Ala Pro Val Leu Val Val Tyr Ala Asp Ser Asp Arg Pro Ser Gly
            180                 185                 190

Ile Pro Glu Arg Phe Ser Gly Ser Asn Ser Gly Asn Thr Ala Thr Leu
        195                 200                 205

Thr Ile Ser Arg Val Glu Val Gly Asp Glu Ala Asp Tyr Tyr Cys Gln
    210                 215                 220

Val Trp Asp Ser Val Ser Tyr His Val Val Phe Gly Gly Gly Thr Thr
225                 230                 235                 240

Leu Thr Val Leu Gly
                245

<210> SEQ ID NO 4
<211> LENGTH: 257
<212> TYPE: PRT
<213> ORGANISM: Artificial Sequence
<220> FEATURE:
<223> OTHER INFORMATION: Synthetic Peptide

<400> SEQUENCE: 4

Gln Val Gln Leu Val Glu Ser Gly Gly Gly Val Val Arg Pro Gly Arg
1               5                   10                  15

Ser Leu Arg Leu Ser Cys Ala Ala Ser Gly Phe Ala Phe Ser Asp Tyr
            20                  25                  30

```
Ser Ile Asn Trp Val Arg Gln Ala Pro Gly Lys Gly Leu Glu Trp Val
            35                  40                  45

Ala Ile Ile Ser Tyr Asp Gly Arg Ile Thr Tyr Tyr Arg Asp Ser Val
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Thr Glu Asp Thr Ala Val Tyr Tyr Cys
            85                  90                  95

Ala Arg Gln Tyr Tyr Asp Phe Trp Ser Gly Ser Val Gly Arg Asn
            100                 105                 110

Tyr Asp Gly Met Asp Val Trp Gly Leu Gly Thr Thr Val Thr Val Ser
            115                 120                 125

Ser Gly Gly Gly Ser Gly Gly Gly Ser Gly Gly Gly Ser
            130                 135                 140

Asp Ile Val Met Thr Gln Ser Pro Leu Ser Leu Ser Val Thr Pro Gly
145                 150                 155                 160

Glu Pro Ala Ser Ile Ser Cys Arg Ser Ser Gln Ser Leu Leu His Arg
            165                 170                 175

Ser Gly Asn Asn Tyr Leu Asp Trp Tyr Leu Gln Lys Pro Gly His Ser
            180                 185                 190

Pro Gln Leu Leu Ile Tyr Val Gly Ser Asn Arg Ala Ser Gly Val Pro
            195                 200                 205

Asp Arg Phe Ser Gly Ser Gly Ser Gly Thr Glu Tyr Thr Leu Arg Ile
            210                 215                 220

Ser Thr Val Glu Ala Glu Asp Val Gly Val Tyr Tyr Cys Met Gln Ala
225                 230                 235                 240

Leu Gln Thr Pro Arg Thr Phe Gly Gln Gly Thr Lys Leu Glu Ile Lys
            245                 250                 255

Arg

<210> SEQ ID NO 5
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Trp Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met His Ser Leu Arg Ala Ala Asp Thr Gly Val Tyr Tyr Cys
            85                  90                  95

Ala Lys Asp Gln Leu Tyr Phe Gly Ser Gln Ser Pro Gly His Tyr Trp
            100                 105                 110

Val Gln Gly Thr Leu Val Thr Val Ser Ser Gly Gly Gly Gly Ser Gly
            115                 120                 125
```

```
Gly Gly Gly Ser Gly Gly Gly Ser Gln Ser Gln Leu Thr Gln Pro
            130                 135                 140
Pro Ser Val Ser Val Ala Pro Gly Gln Thr Ala Arg Ile Thr Cys Gly
145                 150                 155                 160
Gly Asp Asn Ile Gly Ser Lys Ser Val Asn Trp Phe Gln Gln Lys Pro
                165                 170                 175
Gly Gln Ala Pro Val Leu Val Val Tyr Asp Asp Asn Glu Arg Pro Ser
            180                 185                 190
Gly Ile Ser Glu Arg Phe Ser Gly Ser Asn Ser Gly Asn Thr Ala Thr
        195                 200                 205
Leu Thr Ile Ser Arg Val Glu Ala Gly Asp Glu Ala Asp Tyr Tyr Cys
    210                 215                 220
Gln Val Trp Asp Ser Ser Ser Asp His Val Val Phe Gly Gly Gly Thr
225                 230                 235                 240
Lys Leu Thr Val Leu
                245
```

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

```
Ser Gly Ser Gly Leu Lys Lys Lys Trp Ser Thr
1               5                   10
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

```
Cys Glu Thr Gly Ala Lys Pro His Cys
1               5
```

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

```
Lys His Met His Trp His Pro Pro Ala Leu Asn Thr
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

```
Ser Gly Ser Gly Trp Thr Asn Trp Trp Ser Thr
1               5                   10
```

<210> SEQ ID NO 10
<211> LENGTH: 12

```
<212> TYPE: PRT
<213> ORGANISM: Artificial Sequence
<220> FEATURE:
<223> OTHER INFORMATION: Synthetic Peptide

<400> SEQUENCE: 10

Asn Asn Trp Trp Tyr Trp Trp Asp Thr Leu Val Asn
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 11

Gly Leu Trp Arg Phe Trp Phe Gly Asp Phe Leu Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 12

Trp Thr Asp Met Phe Thr Ala Trp Trp Ser Thr Pro
1               5                   10

<210> SEQ ID NO 13
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 13

Leu Arg Asn Ile Arg Leu Arg Asn Ile Arg Leu Arg Asn Ile Arg Leu
1               5                   10                  15

Arg Asn Ile Arg
            20

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Cys Ser Arg Leu Leu Tyr Gly Trp Cys
1               5

<210> SEQ ID NO 15
<211> LENGTH: 740
<212> TYPE: PRT
<213> ORGANISM: Homo sapiens

<400> SEQUENCE: 15

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
                20                  25                  30
```

```
Pro Gly Gly Ser Leu Arg Leu Ser Cys Ala Pro Ser Gly Phe Val Phe
             35                  40                  45

Arg Ser Tyr Gly Met His Trp Val Arg Gln Thr Pro Gly Lys Gly Leu
 50                  55                  60

Glu Trp Val Ser Leu Ile Trp His Asp Gly Ser Asn Arg Phe Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Met
                100                 105                 110

Tyr Phe Cys Ala Arg Glu Arg Leu Ile Ala Ala Pro Ala Ala Phe Asp
            115                 120                 125

Leu Trp Gly Gln Gly Thr Leu Val Thr Val Ser Ser Gly Gly Gly Gly
130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Ser Gly Gly Gly Gly Ser Asp Lys
            260                 265                 270

Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445
```

```
Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Ser Ser Asp Ile Lys Leu Gln Gln Ser Gly Ala Glu Leu Ala Arg
                500                 505                 510

Pro Gly Ala Ser Val Lys Met Ser Cys Lys Thr Ser Gly Tyr Thr Phe
            515                 520                 525

Thr Arg Tyr Thr Met His Trp Val Lys Gln Arg Pro Gly Gln Gly Leu
            530                 535                 540

Glu Trp Ile Gly Tyr Ile Asn Pro Ser Arg Gly Tyr Thr Asn Tyr Asn
545                 550                 555                 560

Gln Lys Phe Lys Asp Lys Ala Thr Leu Thr Thr Asp Lys Ser Ser Ser
                565                 570                 575

Thr Ala Tyr Met Gln Leu Ser Ser Leu Thr Ser Glu Asp Ser Ala Val
                580                 585                 590

Tyr Tyr Cys Ala Arg Tyr Tyr Asp Asp His Tyr Cys Leu Asp Tyr Trp
            595                 600                 605

Gly Gln Gly Thr Thr Leu Thr Val Ser Ser Gly Gly Gly Gly Ser Gly
            610                 615                 620

Gly Gly Gly Ser Gly Gly Gly Gly Ser Asp Ile Gln Leu Thr Gln Ser
625                 630                 635                 640

Pro Ala Ile Met Ser Ala Ser Pro Gly Glu Lys Val Thr Met Thr Cys
                645                 650                 655

Arg Ala Ser Ser Ser Val Ser Tyr Met Asn Trp Tyr Gln Gln Lys Ser
                660                 665                 670

Gly Thr Ser Pro Lys Arg Trp Ile Tyr Asp Thr Ser Lys Val Ala Ser
            675                 680                 685

Gly Val Pro Tyr Arg Phe Ser Gly Ser Gly Ser Gly Thr Ser Tyr Ser
            690                 695                 700

Leu Thr Ile Ser Ser Met Glu Ala Glu Asp Ala Ala Thr Tyr Tyr Cys
705                 710                 715                 720

Gln Gln Trp Ser Ser Asn Pro Leu Thr Phe Gly Ala Gly Thr Lys Leu
                725                 730                 735

Glu Leu Lys Ser
            740

<210> SEQ ID NO 16
<211> LENGTH: 735
<212> TYPE: PRT
<213> ORGANISM: Homo sapiens

<400> SEQUENCE: 16

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
    50                  55                  60
```

```
Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Met
        100                 105                 110

Tyr Phe Cys Ala Arg Glu Arg Leu Ile Ala Ala Pro Ala Ala Phe Asp
            115                 120                 125

Leu Trp Gly Gln Gly Thr Leu Val Thr Val Ser Ser Gly Gly Gly Gly
        130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
            245                 250                 255

Gly Thr Thr Leu Thr Val Leu Gly Ser Gly Gly Gly Ser Gly Ala
            260                 265                 270

Pro Pro Val Ala Gly Pro Ser Val Phe Leu Phe Pro Pro Lys Pro Lys
        275                 280                 285

Asp Thr Leu Met Ile Ser Arg Thr Pro Glu Val Thr Cys Val Val Val
        290                 295                 300

Gly Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Gln Ser Thr Tyr Arg Val Val Ser Val Leu Thr Val Leu His Gln Asp
        340                 345                 350

Trp Leu Asn Gly Lys Glu Tyr Lys Cys Ala Val Ser Asn Lys Gln Leu
        355                 360                 365

Pro Ser Ser Ile Glu Lys Thr Ile Ser Lys Ala Lys Gly Gln Pro Arg
        370                 375                 380

Glu Pro Gln Val Tyr Thr Lys Pro Pro Ser Arg Asp Glu Leu Thr Lys
385                 390                 395                 400

Asn Gln Val Ser Leu Ser Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Val Pro Val Leu Asp Ser Asp Gly Ser Phe Arg Leu Ala Ser
        435                 440                 445

Tyr Leu Thr Val Asp Lys Ser Arg Trp Gln Gln Gly Asn Val Phe Ser
        450                 455                 460

Cys Ser Val Met His Glu Ala Leu His Asn His Tyr Thr Gln Lys Ser
465                 470                 475                 480
```

```
Leu Ser Leu Ser Pro Gly Lys Gly Ser Gly Gly Gly Ser Asp Ile
            485                 490                 495

Lys Leu Gln Gln Ser Gly Ala Glu Leu Ala Arg Pro Gly Ala Ser Val
        500                 505                 510

Lys Met Ser Cys Lys Thr Ser Gly Tyr Thr Phe Thr Arg Tyr Thr Met
        515                 520                 525

His Trp Val Lys Gln Arg Pro Gly Gln Gly Leu Glu Trp Ile Gly Tyr
        530                 535                 540

Ile Asn Pro Ser Arg Gly Tyr Thr Asn Tyr Asn Gln Lys Phe Lys Asp
545                 550                 555                 560

Lys Ala Thr Leu Thr Thr Asp Lys Ser Ser Thr Ala Tyr Met Gln
                565                 570                 575

Leu Ser Ser Leu Thr Ser Glu Asp Ser Ala Val Tyr Tyr Cys Ala Arg
                580                 585                 590

Tyr Tyr Asp His Tyr Cys Leu Asp Tyr Trp Gly Gln Gly Thr Thr
                595                 600                 605

Leu Thr Val Ser Ser Gly Gly Gly Ser Gly Gly Gly Ser Gly
        610                 615                 620

Gly Gly Ser Asp Ile Gln Leu Thr Gln Ser Pro Ala Ile Met Ser
625                 630                 635                 640

Ala Ser Pro Gly Glu Lys Val Thr Met Thr Cys Arg Ala Ser Ser Ser
                645                 650                 655

Val Ser Tyr Met Asn Trp Tyr Gln Gln Lys Ser Gly Thr Ser Pro Lys
                660                 665                 670

Arg Trp Ile Tyr Asp Thr Ser Lys Val Ala Ser Gly Val Pro Tyr Arg
                675                 680                 685

Phe Ser Gly Ser Gly Ser Gly Thr Ser Tyr Ser Leu Thr Ile Ser Ser
        690                 695                 700

Met Glu Ala Glu Asp Ala Ala Thr Tyr Tyr Cys Gln Gln Trp Ser Ser
705                 710                 715                 720

Asn Pro Leu Thr Phe Gly Ala Gly Thr Lys Leu Glu Leu Lys Ser
                725                 730                 735

<210> SEQ ID NO 17
<211> LENGTH: 588
<212> TYPE: PRT
<213> ORGANISM: Homo sapiens

<400> SEQUENCE: 17

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
                20                  25                  30

Pro Gly Gly Ser Leu Arg Leu Ser Cys Ala Pro Ser Gly Phe Val Phe
            35                  40                  45

Arg Ser Tyr Gly Met His Trp Val Arg Gln Thr Pro Gly Lys Gly Leu
        50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
                100                 105                 110

Tyr Phe Cys Ala Arg Glu Arg Leu Ile Ala Ala Pro Ala Ala Phe Asp
            115                 120                 125
```

-continued

Leu Trp Gly Gln Gly Thr Leu Val Thr Val Ser Ser Gly Gly Gly
    130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Ser Gly Gly Gly Ser Glu Ser
            260                 265                 270

Lys Tyr Gly Pro Pro Cys Pro Ser Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Gln Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Gly Leu Pro Ser Ser Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Arg Leu Thr Val Asp
    450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Gly Ser Gly Gly Gly Ser Asp Ile Lys Leu Gln Gln Ser
            500                 505                 510

Gly Ala Glu Leu Ala Arg Pro Gly Ala Ser Val Lys Met Ser Cys Lys
        515                 520                 525

Thr Ser Gly Tyr Thr Phe Thr Arg Tyr Thr Met His Trp Val Lys Gln
    530                 535                 540

```
Arg Pro Gly Gln Gly Leu Glu Trp Ile Gly Tyr Ile Asn Pro Ser Arg
545                 550                 555                 560

Gly Tyr Thr Asn Tyr Asn Gln Lys Phe Lys Asp Lys Ala Thr Leu Thr
            565                 570                 575

Thr Asp Lys Ser Ser Ser Thr Ala Tyr Met Gln Leu
        580                 585

<210> SEQ ID NO 18
<211> LENGTH: 511
<212> TYPE: PRT
<213> ORGANISM: Homo sapiens

<400> SEQUENCE: 18

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Gly Gly Gly Gly Gly
130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Ser Gly Gly Gly Gly Ser Asp Ile
            260                 265                 270

Lys Leu Gln Gln Ser Gly Ala Glu Leu Ala Arg Pro Gly Ala Ser Val
        275                 280                 285

Lys Met Ser Cys Lys Thr Ser Gly Tyr Thr Phe Thr Arg Tyr Thr Met
290                 295                 300

His Trp Val Lys Gln Arg Pro Gly Gln Gly Leu Glu Trp Ile Gly Tyr
305                 310                 315                 320

Ile Asn Pro Ser Arg Gly Tyr Thr Asn Tyr Asn Gln Lys Phe Lys Asp
                325                 330                 335
```

```
Lys Ala Thr Leu Thr Thr Asp Lys Ser Ser Thr Ala Tyr Met Gln
            340                 345                 350

Leu Ser Ser Leu Thr Ser Glu Asp Ser Ala Val Tyr Tyr Cys Ala Arg
            355                 360                 365

Tyr Tyr Asp Asp His Tyr Cys Leu Asp Tyr Trp Gly Gln Gly Thr Thr
            370                 375                 380

Leu Thr Val Ser Ser Gly Gly Gly Gly Ser Gly Gly Gly Gly Ser Gly
385                 390                 395                 400

Gly Gly Gly Ser Asp Ile Gln Leu Thr Gln Ser Pro Ala Ile Met Ser
                405                 410                 415

Ala Ser Pro Gly Glu Lys Val Thr Met Thr Cys Arg Ala Ser Ser Ser
            420                 425                 430

Val Ser Tyr Met Asn Trp Tyr Gln Gln Lys Ser Gly Thr Ser Pro Lys
            435                 440                 445

Arg Trp Ile Tyr Asp Thr Ser Lys Val Ala Ser Gly Val Pro Tyr Arg
            450                 455                 460

Phe Ser Gly Ser Gly Ser Gly Thr Ser Tyr Ser Leu Thr Ile Ser Ser
465                 470                 475                 480

Met Glu Ala Glu Asp Ala Ala Thr Tyr Tyr Cys Gln Gln Trp Ser Ser
                485                 490                 495

Asn Pro Leu Thr Phe Gly Ala Gly Thr Lys Leu Glu Leu Lys Ser
            500                 505                 510

<210> SEQ ID NO 19
<211> LENGTH: 742
<212> TYPE: PRT
<213> ORGANISM: Homo sapiens

<400> SEQUENCE: 19

Met Asp Trp Ile Trp Arg Ile Leu Phe Leu Val Gly Ala Ala Thr Gly
1               5                   10                  15

Ala His Ser Asp Ile Lys Leu Gln Gln Ser Gly Ala Glu Leu Ala Arg
                20                  25                  30

Pro Gly Ala Ser Val Lys Met Ser Cys Lys Thr Ser Gly Tyr Thr Phe
            35                  40                  45

Thr Arg Tyr Thr Met His Trp Val Lys Gln Arg Pro Gly Gln Gly Leu
        50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Ser Asp Ile Gln Leu Thr Gln Ser
145                 150                 155                 160

Pro Ala Ile Met Ser Ala Ser Pro Gly Glu Lys Val Thr Met Thr Cys
                165                 170                 175

Arg Ala Ser Ser Ser Val Ser Tyr Met Asn Trp Tyr Gln Gln Lys Ser
            180                 185                 190
```

```
Gly Thr Ser Pro Lys Arg Trp Ile Tyr Asp Thr Ser Lys Val Ala Ser
            195                 200                 205

Gly Val Pro Tyr Arg Phe Ser Gly Ser Gly Ser Gly Thr Ser Tyr Ser
    210                 215                 220

Leu Thr Ile Ser Ser Met Glu Ala Glu Asp Ala Ala Thr Tyr Tyr Cys
225                 230                 235                 240

Gln Gln Trp Ser Ser Asn Pro Leu Thr Phe Gly Ala Gly Thr Lys Leu
                245                 250                 255

Glu Leu Lys Ser Ser Gly Gly Gly Ser Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
        340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Ser Ser Asp
                485                 490                 495

Ile Gln Val Gln Leu Val Glu Ser Gly Gly Val Val Gln Pro Gly
            500                 505                 510

Gly Ser Leu Arg Leu Ser Cys Ala Pro Ser Gly Phe Val Phe Arg Ser
        515                 520                 525

Tyr Gly Met His Trp Val Arg Gln Thr Pro Gly Lys Gly Leu Glu Trp
    530                 535                 540

Val Ser Leu Ile Trp His Asp Gly Ser Asn Arg Phe Tyr Ala Asp Ser
545                 550                 555                 560

Val Lys Gly Arg Phe Thr Ile Ser Arg Asp Asn Ser Lys Asn Thr Leu
                565                 570                 575

Tyr Leu Gln Met Asn Ser Leu Arg Ala Glu Asp Thr Ala Met Tyr Phe
            580                 585                 590

Cys Ala Arg Glu Arg Leu Ile Ala Ala Pro Ala Phe Asp Leu Trp
        595                 600                 605
```

```
Gly Gln Gly Thr Leu Val Thr Val Ser Ser Gly Gly Gly Ser Gly
    610                 615                 620
Gly Gly Gly Ser Gly Gly Gly Ser Ser Tyr Val Leu Thr Gln Pro
625                 630                 635                 640
Pro Ser Val Ser Val Ala Pro Gly Lys Thr Ala Arg Ile Ser Cys Gly
                645                 650                 655
Gly Asn Asn Ile Gly Thr Lys Asn Val His Trp Tyr Gln Gln Lys Pro
                660                 665                 670
Gly Gln Ala Pro Val Leu Val Val Tyr Ala Asp Ser Asp Arg Pro Ser
                675                 680                 685
Gly Ile Pro Glu Arg Phe Ser Gly Ser Asn Ser Gly Asn Thr Ala Thr
    690                 695                 700
Leu Thr Ile Ser Arg Val Glu Val Gly Asp Glu Ala Asp Tyr Tyr Cys
705                 710                 715                 720
Gln Val Trp Asp Ser Val Ser Tyr His Val Val Phe Gly Gly Gly Thr
                725                 730                 735
Thr Leu Thr Val Leu Gly
            740

<210> SEQ ID NO 20
<211> LENGTH: 731
<212> TYPE: PRT
<213> ORGANISM: Homo sapiens

<400> SEQUENCE: 20

Met Asp Trp Ile Trp Arg Ile Leu Phe Leu Val Gly Ala Ala Thr Gly
1               5                   10                  15
Ala His Ser Asp Ile Lys Leu Gln Gln Ser Gly Ala Glu Leu Ala Arg
                20                  25                  30
Pro Gly Ala Ser Val Lys Met Ser Cys Lys Thr Ser Gly Tyr Thr Phe
            35                  40                  45
Thr Arg Tyr Thr Met His Trp Val Lys Gln Arg Pro Gly Gln Gly Leu
    50                  55                  60
Glu Trp Ile Gly Tyr Ile Asn Pro Ser Arg Gly Tyr Thr Asn Tyr Asn
65                  70                  75                  80
Gln Lys Phe Lys Asp Lys Ala Thr Leu Thr Thr Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Tyr Tyr Asp Asp His Tyr Cys Leu Asp Tyr Trp
        115                 120                 125
Gly Gln Gly Thr Thr Leu Thr Val Ser Ser Gly Gly Gly Gly Ser Gly
    130                 135                 140
Gly Gly Gly Ser Gly Gly Gly Gly Ser Asp Ile Gln Leu Thr Gln Ser
145                 150                 155                 160
Pro Ala Ile Met Ser Ala Ser Pro Gly Glu Lys Val Thr Met Thr Cys
                165                 170                 175
Arg Ala Ser Ser Ser Val Ser Tyr Met Asn Trp Tyr Gln Gln Lys Ser
            180                 185                 190
Gly Thr Ser Pro Lys Arg Trp Ile Tyr Asp Thr Ser Lys Val Ala Ser
        195                 200                 205
Gly Val Pro Tyr Arg Phe Ser Gly Ser Gly Ser Gly Thr Ser Tyr Ser
    210                 215                 220
Leu Thr Ile Ser Ser Met Glu Ala Glu Asp Ala Ala Thr Tyr Tyr Cys
225                 230                 235                 240
```

```
Gln Gln Trp Ser Ser Asn Pro Leu Thr Phe Gly Ala Gly Thr Lys Leu
            245                 250                 255

Glu Leu Lys Ser Ser Gly Gly Gly Ser Pro Tyr Leu Asn Phe Phe
            260                 265                 270

Gln Leu Leu Val Leu Ala Gly Leu Ser His Phe Cys Ser Gly Val Ile
            275                 280                 285

His Val Thr Lys Glu Val Lys Glu Val Ala Thr Leu Ser Cys Gly His
            290                 295                 300

Asn Val Ser Val Glu Glu Leu Ala Gln Thr Arg Ile Tyr Trp Gln Lys
305                 310                 315                 320

Glu Lys Lys Met Val Leu Thr Met Met Ser Gly Asp Met Asn Ile Trp
            325                 330                 335

Pro Glu Tyr Lys Asn Arg Thr Ile Phe Asp Ile Thr Asn Asn Leu Ser
            340                 345                 350

Ile Val Ile Leu Ala Leu Arg Pro Ser Asp Glu Gly Thr Tyr Glu Cys
            355                 360                 365

Val Val Leu Lys Tyr Glu Lys Asp Ala Phe Lys Arg Glu His Leu Ala
            370                 375                 380

Glu Val Thr Leu Ser Val Lys Ala Asp Phe Pro Thr Pro Ser Ile Ser
385                 390                 395                 400

Asp Phe Glu Ile Pro Thr Ser Asn Ile Arg Arg Ile Ile Cys Ser Thr
            405                 410                 415

Ser Gly Gly Phe Pro Glu Pro His Leu Ser Trp Leu Glu Asn Gly Glu
            420                 425                 430

Glu Leu Asn Ala Ile Asn Thr Thr Val Ser Gln Asp Pro Glu Thr Glu
            435                 440                 445

Leu Tyr Ala Val Ser Ser Lys Leu Asp Phe Asn Met Thr Thr Asn His
            450                 455                 460

Ser Phe Met Cys Leu Ile Lys Tyr Gly His Leu Arg Val Asn Gln Thr
465                 470                 475                 480

Phe Asn Ser Ser Asp Ile Gln Val Gln Leu Val Glu Ser Gly Gly Gly
            485                 490                 495

Val Val Gln Pro Gly Gly Ser Leu Arg Leu Ser Cys Ala Pro Ser Gly
            500                 505                 510

Phe Val Phe Arg Ser Tyr Gly Met His Trp Val Arg Gln Thr Pro Gly
            515                 520                 525

Lys Gly Leu Glu Trp Val Ser Leu Ile Trp His Asp Gly Ser Asn Arg
            530                 535                 540

Phe Tyr Ala Asp Ser Val Lys Gly Arg Phe Thr Ile Ser Arg Asp Asn
545                 550                 555                 560

Ser Lys Asn Thr Leu Tyr Leu Gln Met Asn Ser Leu Arg Ala Glu Asp
            565                 570                 575

Thr Ala Met Tyr Phe Cys Ala Arg Glu Arg Leu Ile Ala Ala Pro Ala
            580                 585                 590

Ala Phe Asp Leu Trp Gly Gln Gly Thr Leu Val Thr Val Ser Ser Gly
            595                 600                 605

Gly Gly Gly Ser Gly Gly Gly Gly Ser Gly Gly Gly Gly Ser Ser Tyr
            610                 615                 620

Val Leu Thr Gln Pro Pro Ser Val Ser Val Ala Pro Gly Lys Thr Ala
625                 630                 635                 640

Arg Ile Ser Cys Gly Gly Asn Asn Ile Gly Thr Lys Asn Val His Trp
            645                 650                 655
```

-continued

Tyr Gln Gln Lys Pro Gly Gln Ala Pro Val Leu Val Tyr Ala Asp
                660                 665                 670

Ser Asp Arg Pro Ser Gly Ile Pro Glu Arg Phe Ser Gly Ser Asn Ser
            675                 680                 685

Gly Asn Thr Ala Thr Leu Thr Ile Ser Arg Val Glu Val Gly Asp Glu
        690                 695                 700

Ala Asp Tyr Tyr Cys Gln Val Trp Asp Ser Val Ser Tyr His Val Val
705                 710                 715                 720

Phe Gly Gly Gly Thr Thr Leu Thr Val Leu Gly
                725                 730

<210> SEQ ID NO 21
<211> LENGTH: 964
<212> TYPE: PRT
<213> ORGANISM: Homo sapiens

<400> SEQUENCE: 21

Met Asp Trp Ile Trp Arg Ile Leu Phe Leu Val Gly Ala Ala Thr Gly
1               5                   10                  15

Ala His Ser Asp Ile Lys Leu Gln Gln Ser Gly Ala Glu Leu Ala Arg
            20                  25                  30

Pro Gly Ala Ser Val Lys Met Ser Cys Lys Thr Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Ser Asp Ile Gln Leu Thr Gln Ser
145                 150                 155                 160

Pro Ala Ile Met Ser Ala Ser Pro Gly Glu Lys Val Thr Met Thr Cys
                165                 170                 175

Arg Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Val Ala Ser
        195                 200                 205

Gly Val Pro Tyr Arg Phe Ser Gly Ser Gly Ser Tyr Ser
    210                 215                 220

Leu Thr Ile Ser Ser Met Glu Ala Glu Asp Ala Ala Thr Tyr Tyr Cys
225                 230                 235                 240

Gln Gln Trp Ser Ser Asn Pro Leu Thr Phe Gly Ala Gly Thr Lys Leu
                245                 250                 255

Glu Leu Lys Ser Ser Gly Gly Gly Ser Pro Tyr Leu Asn Phe Phe
            260                 265                 270

Gln Leu Leu Val Leu Ala Gly Leu Ser His Phe Cys Ser Gly Val Ile
        275                 280                 285

His Val Thr Lys Glu Val Lys Glu Val Ala Thr Leu Ser Cys Gly His
    290                 295                 300

```
Asn Val Ser Val Glu Glu Leu Ala Gln Thr Arg Ile Tyr Trp Gln Lys
305                 310                 315                 320

Glu Lys Lys Met Val Leu Thr Met Met Ser Gly Asp Met Asn Ile Trp
            325                 330                 335

Pro Glu Tyr Lys Asn Arg Thr Ile Phe Asp Ile Thr Asn Asn Leu Ser
        340                 345                 350

Ile Val Ile Leu Ala Leu Arg Pro Ser Asp Glu Gly Thr Tyr Glu Cys
            355                 360                 365

Val Val Leu Lys Tyr Glu Lys Asp Ala Phe Lys Arg Glu His Leu Ala
        370                 375                 380

Glu Val Thr Leu Ser Val Lys Ala Asp Phe Pro Thr Pro Ser Ile Ser
385                 390                 395                 400

Asp Phe Glu Ile Pro Thr Ser Asn Ile Arg Arg Ile Ile Cys Ser Thr
                405                 410                 415

Ser Gly Gly Phe Pro Glu Pro His Leu Ser Trp Leu Glu Asn Gly Glu
            420                 425                 430

Glu Leu Asn Ala Ile Asn Thr Thr Val Ser Gln Asp Pro Glu Thr Glu
        435                 440                 445

Leu Tyr Ala Val Ser Ser Lys Leu Asp Phe Asn Met Thr Thr Asn His
    450                 455                 460

Ser Phe Met Cys Leu Ile Lys Tyr Gly His Leu Arg Val Asn Gln Thr
465                 470                 475                 480

Phe Asn Ser Gly Gly Gly Ser Glu Ser Lys Tyr Gly Pro Pro Cys Pro
                485                 490                 495

Ser Cys Pro Ala Pro Val Ala Gly Pro Ser Val Phe Leu Phe Pro
            500                 505                 510

Pro Lys Pro Lys Asp Thr Leu Met Ile Ser Arg Thr Pro Glu Val Thr
        515                 520                 525

Cys Val Val Asp Val Ser Gln Glu Asp Pro Glu Val Gln Phe Asn
    530                 535                 540

Trp Tyr Val Asp Gly Val Glu Val His Asn Ala Lys Thr Lys Pro Arg
545                 550                 555                 560

Glu Glu Gln Phe Gln Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Gly Leu Pro Ser Ser Ile Glu Lys Thr Ile Ser Lys Ala Lys
        595                 600                 605

Gly Gln Pro Arg Glu Pro Gln Val Tyr Thr Leu Pro Pro Ser Gln Glu
    610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Arg Leu Thr Val Asp Lys Ser Arg Trp Gln Glu Gly
        675                 680                 685

Asn Val Phe Ser Cys Ser Val Met His Glu Ala Leu His Asn His Tyr
    690                 695                 700

Thr Gln Lys Ser Leu Ser Leu Ser Pro Gly Lys Ser Ser Asp Ile Gln
705                 710                 715                 720
```

```
Val Gln Leu Val Glu Ser Gly Gly Val Gln Pro Gly Gly Ser
            725                 730             735

Leu Arg Leu Ser Cys Ala Pro Ser Gly Phe Val Phe Ser Tyr Gly
            740                 745             750

Met His Trp Val Arg Gln Thr Pro Gly Lys Gly Leu Glu Trp Val Ser
            755                 760             765

Leu Ile Trp His Asp Gly Ser Asn Arg Phe Tyr Ala Asp Ser Val Lys
            770                 775             780

Gly Arg Phe Thr Ile Ser Arg Asp Asn Ser Lys Asn Thr Leu Tyr Leu
785                 790                 795             800

Gln Met Asn Ser Leu Arg Ala Glu Asp Thr Ala Met Tyr Phe Cys Ala
            805                 810             815

Arg Glu Arg Leu Ile Ala Ala Pro Ala Ala Phe Asp Leu Trp Gly Gln
            820                 825             830

Gly Thr Leu Val Thr Val Ser Ser Gly Gly Gly Gly Ser Gly Gly Gly
            835                 840             845

Gly Ser Gly Gly Gly Gly Ser Ser Tyr Val Leu Thr Gln Pro Pro Ser
850                 855                 860

Val Ser Val Ala Pro Gly Lys Thr Ala Arg Ile Ser Cys Gly Gly Asn
865                 870                 875             880

Asn Ile Gly Thr Lys Asn Val His Trp Tyr Gln Gln Lys Pro Gly Gln
            885                 890             895

Ala Pro Val Leu Val Val Tyr Ala Asp Ser Asp Arg Pro Ser Gly Ile
            900                 905             910

Pro Glu Arg Phe Ser Gly Ser Asn Ser Gly Asn Thr Ala Thr Leu Thr
            915                 920             925

Ile Ser Arg Val Glu Val Gly Asp Glu Ala Asp Tyr Tyr Cys Gln Val
            930                 935             940

Trp Asp Ser Val Ser Tyr His Val Val Phe Gly Gly Gly Thr Thr Leu
945                 950                 955             960

Thr Val Leu Gly

<210> SEQ ID NO 22
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 22

Met Asp Trp Ile Trp Arg Ile Leu Phe Leu Val Gly Ala Ala Thr Gly
1               5                   10                  15

Ala His Ser

<210> SEQ ID NO 23
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 23

Met Ala Leu Pro Val Thr Ala Leu Leu Leu Pro Leu Ala Leu Leu Leu
1               5                   10                  15

His Ala Ala Arg Pro
                20
```

<210> SEQ ID NO 24
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 24

```
Met Glu Phe Gly Leu Ser Trp Leu Phe Leu Val Ala Ile Leu Lys Gly
1               5                   10                  15

Val Gln Cys Ser Arg
            20
```

<210> SEQ ID NO 25
<211> LENGTH: 247
<212> TYPE: PRT
<213> ORGANISM: Artificial Sequence
<220> FEATURE:
<223> OTHER INFORMATION: Synthetic Peptide

<400> SEQUENCE: 25

```
Asp Ile Gln Met Thr Gln Ser Pro Ser Ser Leu Ser Ala Ser Val Gly
1               5                   10                  15

Asp Arg Val Thr Met Thr Cys Arg Ala Ser Ser Asp Ser Val Ser Tyr
            20                  25                  30

Met His Trp Tyr Gln Gln Thr Pro Gly Lys Ala Pro Lys Pro Trp Ile
        35                  40                  45

Tyr Ala Thr Ser Asn Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Trp Ser Ser Asn Pro Pro
                85                  90                  95

Thr Phe Gly Gln Gly Thr Lys Leu Gln Ile Thr Arg Gly Gly Gly Gly
            100                 105                 110

Ser Gly Gly Gly Gly Ser Gly Gly Gly Ser Gln Val Gln Leu Val
        115                 120                 125

Gln Ser Gly Gly Gly Val Val Gln Pro Gly Arg Ser Leu Arg Leu Ser
    130                 135                 140

Cys Lys Ala Ser Gly Tyr Thr Phe Thr Ser Tyr Ala Met Tyr Trp Val
145                 150                 155                 160

Arg Gln Ala Pro Gly Lys Gly Leu Glu Trp Val Ala Ile Ile Asn Pro
                165                 170                 175

Ser Ser Gly Tyr Thr Lys Asn Gln Lys Phe Asp Arg Phe Thr Ile Ser
            180                 185                 190

Ala Asp Lys Ser Lys Ser Thr Ala Phe Leu Gln Met Asp Ser Leu Arg
        195                 200                 205

Pro Glu Asp Thr Gly Val Tyr Phe Cys Ala Arg Asp Gly Asp Tyr Asp
    210                 215                 220

Val Tyr Phe Ser Ala Ser Cys Phe Gly Pro Asp Tyr Trp Gly Gln Gly
225                 230                 235                 240

Thr Pro Val Thr Val Ser Ser
            245
```

<210> SEQ ID NO 26
<211> LENGTH: 247
<212> TYPE: PRT
<213> ORGANISM: Artificial Sequence
<220> FEATURE:

<223> OTHER INFORMATION: Synthetic Peptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Ser Glu Val Gly Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Tyr Ser Phe Thr Gly Tyr Thr Met Asn
145                 150                 155                 160

Trp Val Arg Gln Ala Pro Gly Lys Gly Leu Glu Trp Val Ala Leu Ile
                165                 170                 175

Asn Pro Tyr Lys Gly Val Thr Thr Tyr Ala Asp Ser Val Lys Gly Arg
            180                 185                 190

Phe Thr Ile Ser Val Asp Lys Ser Lys Asn Thr Ala Tyr Leu Gln Met
        195                 200                 205

Asn Ser Leu Arg Ala Glu Asp Thr Ala Val Tyr Tyr Cys Ala Arg Ser
210                 215                 220

Gly Tyr Tyr Gly Asp Ser Asp Trp Tyr Phe Asp Val Trp Gly Gln Gly
225                 230                 235                 240

Thr Leu Val Thr Val Ser Ser
                245

<210> SEQ ID NO 27
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ser Ala Tyr Tyr Asp Tyr Asp Gly Phe Ala Tyr Trp Gly Gln
            100                 105                 110

Gly Thr Leu Val Thr Val Ser Gly Gly Gly Gly Ser Gly Gly Gly
            115                 120                 125

Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
        210                 215                 220

Trp Ser Ser Asn Pro Pro Thr Phe Gly Gly Gly Thr Lys Val Glu Ile
225                 230                 235                 240

Lys
```

<210> SEQ ID NO 28
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 28

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
            195                 200                 205
```

```
Ser Ser Leu Gln Pro Glu Asp Ile Ala Thr Tyr Tyr Cys Gln Gln Trp
    210                 215                 220

Ser Ser Asn Pro Phe Thr Phe Gly Gln Gly Thr Lys Leu Gln Ile Thr
225                 230                 235                 240

Arg

<210> SEQ ID NO 29
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 29

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
    210                 215                 220

Ser Ser Asn Pro Phe Thr Phe Gly Gln Gly Thr Lys Leu Gln Ile Thr
225                 230                 235                 240

Arg

<210> SEQ ID NO 30
<211> LENGTH: 242
<212> TYPE: PRT
<213> ORGANISM: Artificial Sequence
<220> FEATURE:
<223> OTHER INFORMATION: Synthetic Peptide

<400> SEQUENCE: 30

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Gly Gly Gly Ser Gly Gly Gly
            115                 120                 125

Gly Ser Gly Gly Gly Ser Asp Ile Gln Met Thr Gln Ser Pro Ser
130                 135                 140

Ser Leu Ser Ala Ser Val Gly Asp Arg Val Thr Ile Thr Cys His Ala
145                 150                 155                 160

Ser Gln Asn Ile Tyr Val Trp Leu Asn Trp Tyr Gln Gln Lys Pro Gly
                165                 170                 175

Lys Ala Pro Lys Leu Leu Ile Tyr Lys Ala Ser Asn Leu His Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Gly Gln Thr Tyr Pro Tyr Thr Phe Gly Gly Gly Thr Lys Val Glu
225                 230                 235                 240

Ile Lys

<210> SEQ ID NO 31
<211> LENGTH: 232
<212> TYPE: PRT
<213> ORGANISM: Artificial Sequence
<220> FEATURE:
<223> OTHER INFORMATION: Synthetic Peptide

<400> SEQUENCE: 31

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 32
<211> LENGTH: 228
<212> TYPE: PRT
<213> ORGANISM: Artificial Sequence
<220> FEATURE:
<223> OTHER INFORMATION: Synthetic Peptide

<400> SEQUENCE: 32

Glu Arg Lys Cys Cys Val Glu Cys Pro Pro Cys Pro Ala Pro Pro Ala
1               5                   10                  15

Ala Ala Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 33
<211> LENGTH: 228
```

```
<212> TYPE: PRT
<213> ORGANISM: Artificial Sequence
<220> FEATURE:
<223> OTHER INFORMATION: Synthetic Peptide

<400> SEQUENCE: 33
```

Glu Ser Lys Tyr Gly Pro Pro Cys Pro Ser Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

```
<210> SEQ ID NO 34
<211> LENGTH: 130
<212> TYPE: PRT
<213> ORGANISM: Artificial Sequence
<220> FEATURE:
<223> OTHER INFORMATION: Synthetic Peptide

<400> SEQUENCE: 34
```

Glu Pro Lys Ser Ser Asp Lys Thr His Thr Ser Pro Pro Ser Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
        115                 120                 125

Arg Glu
    130

<210> SEQ ID NO 35
<211> LENGTH: 126
<212> TYPE: PRT
<213> ORGANISM: Artificial Sequence
<220> FEATURE:
<223> OTHER INFORMATION: Synthetic Peptide

<400> SEQUENCE: 35

Glu Arg Lys Cys Cys Val Glu Cys Pro Pro Cys Pro Ala Pro Pro Ala
1               5                   10                  15

Ala Ala Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu
        115                 120                 125

<210> SEQ ID NO 36
<211> LENGTH: 232
<212> TYPE: PRT
<213> ORGANISM: Artificial Sequence
<220> FEATURE:
<223> OTHER INFORMATION: Synthetic Peptide

<400> SEQUENCE: 36

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 37
<211> LENGTH: 229
<212> TYPE: PRT
<213> ORGANISM: Artificial Sequence
<220> FEATURE:
<223> OTHER INFORMATION: Synthetic Peptide

<400> SEQUENCE: 37

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 38
```

```
<211> LENGTH: 742
<212> TYPE: PRT
<213> ORGANISM: Artificial Sequence
<220> FEATURE:
<223> OTHER INFORMATION: Synthetic Peptide

<400> SEQUENCE: 38

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
    50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Ser Gly Gly Gly Gly
130                 135                 140

Ser Gly Gly Gly Gly Ser Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Glu Pro Lys Ser Cys Asp Lys Thr
            260                 265                 270

His Thr Cys Pro Pro Cys Pro Ala Pro Glu Ala Ala Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Gln Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380
```

```
Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
    435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Ser Gly Ser Gly Ser Gln Val Gln Leu Val Gln Ser Gly Gly Gly Val
            500                 505                 510

Val Gln Pro Gly Arg Ser Leu Arg Leu Ser Cys Lys Ala Ser Gly Tyr
        515                 520                 525

Thr Phe Thr Arg Tyr Thr Met His Trp Val Arg Gln Ala Pro Gly Lys
    530                 535                 540

Gly Leu Glu Trp Ile Gly Tyr Ile Asn Pro Ser Arg Gly Tyr Thr Asn
545                 550                 555                 560

Tyr Asn Gln Lys Val Lys Asp Arg Phe Thr Ile Ser Arg Asp Asn Ser
                565                 570                 575

Lys Asn Thr Ala Phe Leu Gln Met Asp Ser Leu Arg Pro Glu Asp Thr
            580                 585                 590

Gly Val Tyr Phe Cys Ala Arg Tyr Tyr Asp Asp His Tyr Cys Leu Asp
        595                 600                 605

Tyr Trp Gly Gln Gly Thr Pro Val Thr Val Ser Ser Gly Gly Gly Gly
    610                 615                 620

Ser Gly Gly Gly Gly Ser Gly Gly Gly Gly Ser Asp Ile Gln Met Thr
625                 630                 635                 640

Gln Ser Pro Ser Ser Leu Ser Ala Ser Val Gly Asp Arg Val Thr Ile
                645                 650                 655

Thr Cys Ser Ala Ser Ser Ser Val Ser Tyr Met Asn Trp Tyr Gln Gln
            660                 665                 670

Thr Pro Gly Lys Ala Pro Lys Arg Trp Ile Tyr Asp Thr Ser Lys Leu
        675                 680                 685

Ala Ser Gly Val Pro Ser Arg Phe Ser Gly Ser Gly Ser Gly Thr Asp
    690                 695                 700

Tyr Thr Phe Thr Ile Ser Ser Leu Gln Pro Glu Asp Ile Ala Thr Tyr
705                 710                 715                 720

Tyr Cys Gln Gln Trp Ser Ser Asn Pro Phe Thr Phe Gly Gln Gly Thr
                725                 730                 735

Lys Leu Gln Ile Thr Arg
            740

<210> SEQ ID NO 39
<211> LENGTH: 496
<212> TYPE: PRT
<213> ORGANISM: Artificial Sequence
<220> FEATURE:
<223> OTHER INFORMATION: Synthetic Peptide

<400> SEQUENCE: 39
```

```
Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
    50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Ser Gly Gly Gly Gly
    130                 135                 140

Ser Gly Gly Gly Gly Ser Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Glu Pro Lys Ser Cys Asp Lys Thr
            260                 265                 270

His Thr Cys Pro Pro Cys Pro Ala Pro Glu Ala Ala Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Gln Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415
```

```
Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 40
<211> LENGTH: 510
<212> TYPE: PRT
<213> ORGANISM: Artificial Sequence
<220> FEATURE:
<223> OTHER INFORMATION: Synthetic Peptide

<400> SEQUENCE: 40

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
    50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Ser Gly Gly Gly Gly
    130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
            165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
            245                 250                 255

Gly Thr Thr Leu Thr Val Leu Gly Gly Gly Gly Ser Val Gln
            260                 265                 270

Leu Val Gln Ser Gly Gly Val Val Gln Pro Gly Arg Ser Leu Arg
        275                 280                 285
```

```
Leu Ser Cys Lys Ala Ser Gly Tyr Thr Phe Thr Arg Tyr Thr Met His
    290                 295                 300

Trp Val Arg Gln Ala Pro Gly Lys Gly Leu Glu Trp Ile Gly Tyr Ile
305                 310                 315                 320

Asn Pro Ser Arg Gly Tyr Thr Asn Tyr Asn Gln Lys Val Lys Asp Arg
                325                 330                 335

Phe Thr Ile Ser Arg Asp Asn Ser Lys Asn Thr Ala Phe Leu Gln Met
            340                 345                 350

Asp Ser Leu Arg Pro Glu Asp Thr Gly Val Tyr Phe Cys Ala Arg Tyr
        355                 360                 365

Tyr Asp Asp His Tyr Cys Leu Asp Tyr Trp Gly Gln Gly Thr Pro Val
    370                 375                 380

Thr Val Ser Ser Gly Gly Gly Ser Gly Gly Gly Ser Gly Gly
385                 390                 395                 400

Gly Gly Ser Asp Ile Gln Met Thr Gln Ser Pro Ser Ser Leu Ser Ala
                405                 410                 415

Ser Val Gly Asp Arg Val Thr Ile Thr Cys Ser Ala Ser Ser Ser Val
                420                 425                 430

Ser Tyr Met Asn Trp Tyr Gln Gln Thr Pro Gly Lys Ala Pro Lys Arg
            435                 440                 445

Trp Ile Tyr Asp Thr Ser Lys Leu Ala Ser Gly Val Pro Ser Arg Phe
450                 455                 460

Ser Gly Ser Gly Ser Gly Thr Asp Tyr Thr Phe Thr Ile Ser Ser Leu
465                 470                 475                 480

Gln Pro Glu Asp Ile Ala Thr Tyr Tyr Cys Gln Gln Trp Ser Ser Asn
                485                 490                 495

Pro Phe Thr Phe Gly Gln Gly Thr Lys Leu Gln Ile Thr Arg
            500                 505                 510

<210> SEQ ID NO 41
<211> LENGTH: 754
<212> TYPE: PRT
<213> ORGANISM: Artificial Sequence
<220> FEATURE:
<223> OTHER INFORMATION: Synthetic Peptide

<400> SEQUENCE: 41

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Arg
                20                  25                  30

Pro Gly Arg Ser Leu Arg Leu Ser Cys Ala Ala Ser Gly Phe Ala Phe
            35                  40                  45

Ser Asp Tyr Ser Ile Asn Trp Val Arg Gln Ala Pro Gly Lys Gly Leu
        50                  55                  60

Glu Trp Val Ala Ile Ile Ser Tyr Asp Gly Arg Ile Thr Tyr Tyr Arg
65                  70                  75                  80

Asp Ser Val Lys Gly Arg Phe Thr Ile Ser Arg Asp Asp Ser Lys Asn
                85                  90                  95

Thr Leu Tyr Leu Gln Met Asn Ser Leu Arg Thr Glu Asp Thr Ala Val
            100                 105                 110

Tyr Tyr Cys Ala Arg Gln Tyr Tyr Asp Phe Trp Ser Gly Ser Ser Val
        115                 120                 125

Gly Arg Asn Tyr Asp Gly Met Asp Val Trp Gly Leu Gly Thr Thr Val
    130                 135                 140
```

-continued

```
Thr Val Ser Ser Gly Gly Gly Gly Ser Gly Gly Gly Ser Gly Gly
145                 150                 155                 160

Gly Gly Ser Asp Ile Val Met Thr Gln Ser Pro Leu Ser Leu Ser Val
            165                 170                 175

Thr Pro Gly Glu Pro Ala Ser Ile Ser Cys Arg Ser Ser Gln Ser Leu
            180                 185                 190

Leu His Arg Ser Gly Asn Asn Tyr Leu Asp Trp Tyr Leu Gln Lys Pro
        195                 200                 205

Gly His Ser Pro Gln Leu Leu Ile Tyr Val Gly Ser Asn Arg Ala Ser
        210                 215                 220

Gly Val Pro Asp Arg Phe Ser Gly Ser Gly Ser Gly Thr Glu Tyr Thr
225                 230                 235                 240

Leu Arg Ile Ser Thr Val Glu Ala Glu Asp Val Gly Val Tyr Tyr Cys
            245                 250                 255

Met Gln Ala Leu Gln Thr Pro Arg Thr Phe Gly Gln Gly Thr Lys Leu
            260                 265                 270

Glu Ile Lys Arg Glu Pro Lys Ser Cys Asp Lys Thr His Thr Cys Pro
        275                 280                 285

Pro Cys Pro Ala Pro Glu Ala Ala Gly Gly Pro Ser Val Phe Leu Phe
290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
            325                 330                 335

Asn Trp Tyr Val Asp Gly Val Glu Val His Asn Ala Lys Thr Lys Pro
            340                 345                 350

Arg Glu Glu Gln Tyr Gln Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
            405                 410                 415

Asp Glu Leu Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
            485                 490                 495

Tyr Thr Gln Lys Ser Leu Ser Leu Ser Pro Gly Lys Ser Gly Ser Gly
            500                 505                 510

Ser Gln Val Gln Leu Val Gln Ser Gly Gly Val Val Gln Pro Gly
        515                 520                 525

Arg Ser Leu Arg Leu Ser Cys Lys Ala Ser Gly Tyr Thr Phe Thr Arg
530                 535                 540

Tyr Thr Met His Trp Val Arg Gln Ala Pro Gly Lys Gly Leu Glu Trp
545                 550                 555                 560
```

```
Ile Gly Tyr Ile Asn Pro Ser Arg Gly Tyr Thr Asn Tyr Asn Gln Lys
                565                 570                 575

Val Lys Asp Arg Phe Thr Ile Ser Arg Asp Asn Ser Lys Asn Thr Ala
            580                 585                 590

Phe Leu Gln Met Asp Ser Leu Arg Pro Glu Asp Thr Gly Val Tyr Phe
        595                 600                 605

Cys Ala Arg Tyr Tyr Asp Asp His Tyr Cys Leu Asp Tyr Trp Gly Gln
610                 615                 620

Gly Thr Pro Val Thr Val Ser Ser Gly Gly Gly Ser Gly Gly Gly
625                 630                 635                 640

Gly Ser Gly Gly Gly Ser Asp Ile Gln Met Thr Gln Ser Pro Ser
                645                 650                 655

Ser Leu Ser Ala Ser Val Gly Asp Arg Val Thr Ile Thr Cys Ser Ala
            660                 665                 670

Ser Ser Ser Val Ser Tyr Met Asn Trp Tyr Gln Gln Thr Pro Gly Lys
        675                 680                 685

Ala Pro Lys Arg Trp Ile Tyr Asp Thr Ser Lys Leu Ala Ser Gly Val
    690                 695                 700

Pro Ser Arg Phe Ser Gly Ser Gly Ser Gly Thr Asp Tyr Thr Phe Thr
705                 710                 715                 720

Ile Ser Ser Leu Gln Pro Glu Asp Ile Ala Thr Tyr Tyr Cys Gln Gln
                725                 730                 735

Trp Ser Ser Asn Pro Phe Thr Phe Gly Gln Gly Thr Lys Leu Gln Ile
            740                 745                 750

Thr Arg

<210> SEQ ID NO 42
<211> LENGTH: 508
<212> TYPE: PRT
<213> ORGANISM: Artificial Sequence
<220> FEATURE:
<223> OTHER INFORMATION: Synthetic Peptide

<400> SEQUENCE: 42

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Arg
            20                  25                  30

Pro Gly Arg Ser Leu Arg Leu Ser Cys Ala Ala Ser Gly Phe Ala Phe
        35                  40                  45

Ser Asp Tyr Ser Ile Asn Trp Val Arg Gln Ala Pro Gly Lys Gly Leu
    50                  55                  60

Glu Trp Val Ala Ile Ile Ser Tyr Asp Gly Arg Ile Thr Tyr Tyr Arg
65                  70                  75                  80

Asp Ser Val Lys Gly Arg Phe Thr Ile Ser Arg Asp Asp Ser Lys Asn
                85                  90                  95

Thr Leu Tyr Leu Gln Met Asn Ser Leu Arg Thr Glu Asp Thr Ala Val
            100                 105                 110

Tyr Tyr Cys Ala Arg Gln Tyr Tyr Asp Phe Trp Ser Gly Ser Ser Val
        115                 120                 125

Gly Arg Asn Tyr Asp Gly Met Asp Val Trp Gly Leu Gly Thr Thr Val
    130                 135                 140

Thr Val Ser Ser Gly Gly Gly Gly Ser Gly Gly Gly Gly Ser Gly Gly
145                 150                 155                 160
```

```
Gly Gly Ser Asp Ile Val Met Thr Gln Ser Pro Leu Ser Leu Ser Val
                165                 170                 175
Thr Pro Gly Glu Pro Ala Ser Ile Ser Cys Arg Ser Ser Gln Ser Leu
            180                 185                 190
Leu His Arg Ser Gly Asn Asn Tyr Leu Asp Trp Tyr Leu Gln Lys Pro
        195                 200                 205
Gly His Ser Pro Gln Leu Leu Ile Tyr Val Gly Ser Asn Arg Ala Ser
    210                 215                 220
Gly Val Pro Asp Arg Phe Ser Gly Ser Gly Ser Gly Thr Glu Tyr Thr
225                 230                 235                 240
Leu Arg Ile Ser Thr Val Glu Ala Glu Asp Val Gly Val Tyr Tyr Cys
                245                 250                 255
Met Gln Ala Leu Gln Thr Pro Arg Thr Phe Gly Gln Gly Thr Lys Leu
            260                 265                 270
Glu Ile Lys Arg Glu Pro Lys Ser Cys Asp Lys Thr His Thr Cys Pro
        275                 280                 285
Pro Cys Pro Ala Pro Glu Ala Ala Gly Gly Pro Ser Val Phe Leu Phe
    290                 295                 300
Pro Pro Lys Pro Lys Asp Thr Leu Met Ile Ser Arg Thr Pro Glu Val
305                 310                 315                 320
Thr Cys Val Val Val Asp Val Ser His Glu Asp Pro Glu Val Lys Phe
                325                 330                 335
Asn Trp Tyr Val Asp Gly Val Glu Val His Asn Ala Lys Thr Lys Pro
            340                 345                 350
Arg Glu Glu Gln Tyr Gln Ser Thr Tyr Arg Val Val Ser Val Leu Thr
        355                 360                 365
Val Leu His Gln Asp Trp Leu Asn Gly Lys Glu Tyr Lys Cys Lys Val
    370                 375                 380
Ser Asn Lys Ala Leu Pro Ala Pro Ile Glu Lys Thr Ile Ser Lys Ala
385                 390                 395                 400
Lys Gly Gln Pro Arg Glu Pro Gln Val Tyr Thr Leu Pro Pro Ser Arg
                405                 410                 415
Asp Glu Leu Thr Lys Asn Gln Val Ser Leu Thr Cys Leu Val Lys Gly
            420                 425                 430
Phe Tyr Pro Ser Asp Ile Ala Val Glu Trp Glu Ser Asn Gly Gln Pro
        435                 440                 445
Glu Asn Asn Tyr Lys Thr Thr Pro Pro Val Leu Asp Ser Asp Gly Ser
    450                 455                 460
Phe Phe Leu Tyr Ser Lys Leu Thr Val Asp Lys Ser Arg Trp Gln Gln
465                 470                 475                 480
Gly Asn Val Phe Ser Cys Ser Val Met His Glu Ala Leu His Asn His
                485                 490                 495
Tyr Thr Gln Lys Ser Leu Ser Leu Ser Pro Gly Lys
            500                 505
```

<210> SEQ ID NO 43
<211> LENGTH: 523
<212> TYPE: PRT
<213> ORGANISM: Artificial Sequence
<220> FEATURE:
<223> OTHER INFORMATION: Synthetic Peptide

<400> SEQUENCE: 43

```
Met Asp Trp Ile Trp Arg Ile Leu Phe Leu Val Gly Ala Ala Thr Gly
1               5                   10                  15
```

```
Ala His Ser Gln Val Gln Leu Val Glu Ser Gly Gly Val Val Arg
            20                  25                  30
Pro Gly Arg Ser Leu Arg Leu Ser Cys Ala Ala Ser Gly Phe Ala Phe
            35                  40                  45
Ser Asp Tyr Ser Ile Asn Trp Val Arg Gln Ala Pro Gly Lys Gly Leu
        50                  55                  60
Glu Trp Val Ala Ile Ile Ser Tyr Asp Gly Arg Ile Thr Tyr Tyr Arg
 65                 70                  75                  80
Asp Ser Val Lys Gly Arg Phe Thr Ile Ser Arg Asp Asp Ser Lys Asn
                85                  90                  95
Thr Leu Tyr Leu Gln Met Asn Ser Leu Arg Thr Glu Asp Thr Ala Val
            100                 105                 110
Tyr Tyr Cys Ala Arg Gln Tyr Tyr Asp Phe Trp Ser Gly Ser Ser Val
            115                 120                 125
Gly Arg Asn Tyr Asp Gly Met Asp Val Trp Gly Leu Gly Thr Thr Val
            130                 135                 140
Thr Val Ser Ser Gly Gly Gly Gly Ser Gly Gly Gly Gly Ser Gly Gly
145                 150                 155                 160
Gly Gly Ser Asp Ile Val Met Thr Gln Ser Pro Leu Ser Leu Ser Val
                165                 170                 175
Thr Pro Gly Glu Pro Ala Ser Ile Ser Cys Arg Ser Ser Gln Ser Leu
            180                 185                 190
Leu His Arg Ser Gly Asn Asn Tyr Leu Asp Trp Tyr Leu Gln Lys Pro
            195                 200                 205
Gly His Ser Pro Gln Leu Leu Ile Tyr Val Gly Ser Asn Arg Ala Ser
        210                 215                 220
Gly Val Pro Asp Arg Phe Ser Gly Ser Gly Ser Gly Thr Glu Tyr Thr
225                 230                 235                 240
Leu Arg Ile Ser Thr Val Glu Ala Glu Asp Val Gly Val Tyr Tyr Cys
                245                 250                 255
Met Gln Ala Leu Gln Thr Pro Arg Thr Phe Gly Gln Gly Thr Lys Leu
            260                 265                 270
Glu Ile Lys Arg Ser Gly Gly Gly Gly Ser Gln Val Gln Leu Val Gln
            275                 280                 285
Ser Gly Gly Gly Val Val Gln Pro Gly Arg Ser Leu Arg Leu Ser Cys
290                 295                 300
Lys Ala Ser Gly Tyr Thr Phe Thr Arg Tyr Thr Met His Trp Val Arg
305                 310                 315                 320
Gln Ala Pro Gly Lys Gly Leu Glu Trp Ile Gly Tyr Ile Asn Pro Ser
                325                 330                 335
Arg Gly Tyr Thr Asn Tyr Asn Gln Lys Val Lys Asp Arg Phe Thr Ile
            340                 345                 350
Ser Arg Asp Asn Ser Lys Asn Thr Ala Phe Leu Gln Met Asp Ser Leu
            355                 360                 365
Arg Pro Glu Asp Thr Gly Val Tyr Phe Cys Ala Arg Tyr Tyr Asp Asp
        370                 375                 380
His Tyr Cys Leu Asp Tyr Trp Gly Gln Gly Thr Pro Val Thr Val Ser
385                 390                 395                 400
Ser Gly Gly Gly Gly Ser Gly Gly Gly Gly Ser Gly Gly Gly Gly Ser
                405                 410                 415
Asp Ile Gln Met Thr Gln Ser Pro Ser Ser Leu Ser Ala Ser Val Gly
            420                 425                 430
```

```
Asp Arg Val Thr Ile Thr Cys Ser Ala Ser Ser Val Ser Tyr Met
            435                 440                 445

Asn Trp Tyr Gln Gln Thr Pro Gly Lys Ala Pro Lys Arg Trp Ile Tyr
450                 455                 460

Asp Thr Ser Lys Leu Ala Ser Gly Val Pro Ser Arg Phe Ser Gly Ser
465                 470                 475                 480

Gly Ser Gly Thr Asp Tyr Thr Phe Thr Ile Ser Ser Leu Gln Pro Glu
                485                 490                 495

Asp Ile Ala Thr Tyr Tyr Cys Gln Gln Trp Ser Ser Asn Pro Phe Thr
                500                 505                 510

Phe Gly Gln Gly Thr Lys Leu Gln Ile Thr Arg
            515                 520

<210> SEQ ID NO 44
<211> LENGTH: 492
<212> TYPE: PRT
<213> ORGANISM: Artificial Sequence
<220> FEATURE:
<223> OTHER INFORMATION: Synthetic Peptide

<400> SEQUENCE: 44

Met Asp Trp Ile Trp Arg Ile Leu Phe Leu Val Gly Ala Ala Thr Gly
1               5                   10                  15

Ala His Ser Gln Val Gln Leu Val Gln Ser Gly Gly Gly Val Val Gln
                20                  25                  30

Pro Gly Arg Ser Leu Arg Leu Ser Cys Lys Ala Ser Gly Tyr Thr Phe
            35                  40                  45

Thr Arg Tyr Thr Met His Trp Val Arg Gln Ala Pro Gly Lys Gly Leu
50                  55                  60

Glu Trp Ile Gly Tyr Ile Asn Pro Ser Arg Gly Tyr Thr Asn Tyr Asn
65                  70                  75                  80

Gln Lys Val Lys Asp Arg Phe Thr Ile Ser Arg Asp Asn Ser Lys Asn
                85                  90                  95

Thr Ala Phe Leu Gln Met Asp Ser Leu Arg Pro Glu Asp Thr Gly Val
            100                 105                 110

Tyr Phe Cys Ala Arg Tyr Tyr Asp Asp His Tyr Cys Leu Asp Tyr Trp
        115                 120                 125

Gly Gln Gly Thr Pro Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Ser Ala Ser Ser Ser Val Ser Tyr Met Asn Trp Tyr Gln Gln Thr Pro
            180                 185                 190

Gly Lys Ala Pro Lys Arg Trp Ile Tyr Asp Thr Ser Lys Leu Ala Ser
        195                 200                 205

Gly Val Pro Ser Arg Phe Ser Gly Ser Gly Ser Gly Thr Asp Tyr Thr
    210                 215                 220

Phe Thr Ile Ser Ser Leu Gln Pro Glu Asp Ile Ala Thr Tyr Tyr Cys
225                 230                 235                 240

Gln Gln Trp Ser Ser Asn Pro Phe Thr Phe Gly Gln Gly Thr Lys Leu
                245                 250                 255

Gln Ile Thr Arg Glu Pro Lys Ser Cys Asp Lys Thr His Thr Cys Pro
            260                 265                 270
```

```
Pro Cys Pro Ala Pro Glu Ala Ala Gly Gly Pro Ser Val Phe Leu Phe
        275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Gln Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 45
<211> LENGTH: 260
<212> TYPE: PRT
<213> ORGANISM: Artificial Sequence
<220> FEATURE:
<223> OTHER INFORMATION: Synthetic Peptide

<400> SEQUENCE: 45

Met Asp Trp Ile Trp Arg Ile Leu Phe Leu Val Gly Ala Ala Thr Gly
1               5                   10                  15

Ala His Ser Gln Val Gln Leu Val Gln Ser Gly Gly Gly Val Val Gln
            20                  25                  30

Pro Gly Arg Ser Leu Arg Leu Ser Cys Lys Ala Ser Gly Tyr Thr Phe
        35                  40                  45

Thr Arg Tyr Thr Met His Trp Val Arg Gln Ala Pro Gly Lys Gly Leu
    50                  55                  60

Glu Trp Ile Gly Tyr Ile Asn Pro Ser Arg Gly Tyr Thr Asn Tyr Asn
65                  70                  75                  80

Gln Lys Val Lys Asp Arg Phe Thr Ile Ser Arg Asp Asn Ser Lys Asn
                85                  90                  95

Thr Ala Phe Leu Gln Met Asp Ser Leu Arg Pro Glu Asp Thr Gly Val
            100                 105                 110

Tyr Phe Cys Ala Arg Tyr Tyr Asp Asp His Tyr Cys Leu Asp Tyr Trp
        115                 120                 125

Gly Gln Gly Thr Pro Val Thr Val Ser Ser Gly Gly Gly Gly Ser Gly
    130                 135                 140
```

-continued

```
Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Ser Ala Ser Ser Ser Val Ser Tyr Met Asn Trp Tyr Gln Gln Thr Pro
            180                 185                 190

Gly Lys Ala Pro Lys Arg Trp Ile Tyr Asp Thr Ser Lys Leu Ala Ser
        195                 200                 205

Gly Val Pro Ser Arg Phe Ser Gly Ser Gly Ser Gly Thr Asp Tyr Thr
    210                 215                 220

Phe Thr Ile Ser Ser Leu Gln Pro Glu Asp Ile Ala Thr Tyr Tyr Cys
225                 230                 235                 240

Gln Gln Trp Ser Ser Asn Pro Phe Thr Phe Gly Gln Gly Thr Lys Leu
                245                 250                 255

Gln Ile Thr Arg
            260
```